United States Patent
Davidow et al.

(10) Patent No.: US 12,263,275 B2
(45) Date of Patent: Apr. 1, 2025

(54) FISTULA FILLER AND DEPLOYMENT SYSTEM

(71) Applicant: MIROMATRIX MEDICAL INC., Eden Prarie, MN (US)

(72) Inventors: Dominique Davidow, Minnetonka, MN (US); Aleksandr Katane, Victoria, MN (US); Ben Steiner, Bloomington, MN (US)

(73) Assignee: Miromatrix Medical Inc., Eden Prairie, MN (US)

( * ) Notice: Subject to any disclaimer, the term of this patent is extended or adjusted under 35 U.S.C. 154(b) by 831 days.

(21) Appl. No.: 17/251,573

(22) PCT Filed: Jun. 13, 2019

(86) PCT No.: PCT/US2019/036942
§ 371 (c)(1),
(2) Date: Dec. 11, 2020

(87) PCT Pub. No.: WO2019/241499
PCT Pub. Date: Dec. 19, 2019

(65) Prior Publication Data
US 2021/0236695 A1 Aug. 5, 2021

Related U.S. Application Data

(60) Provisional application No. 62/684,426, filed on Jun. 13, 2018.

(51) Int. Cl.
*A61L 27/04* (2006.01)
*A61L 27/14* (2006.01)
*A61L 27/36* (2006.01)

(52) U.S. Cl.
CPC ........... *A61L 27/3633* (2013.01); *A61L 27/04* (2013.01); *A61L 27/14* (2013.01); *A61L 27/3641* (2013.01); *A61L 27/3683* (2013.01); *A61L 2430/40* (2013.01)

(58) Field of Classification Search
CPC ...... A61L 27/3633; A61L 27/04; A61L 27/14; A61L 27/3641; A61L 27/3683; A61L 2430/40
See application file for complete search history.

(56) References Cited

U.S. PATENT DOCUMENTS

| | | |
|---|---|---|
| 3,545,221 A | 12/1970 | Koski et al. |
| 3,639,084 A | 2/1972 | Goldhaber |
| 4,083,066 A | 4/1978 | Schmitz et al. |
| 4,801,299 A | 1/1989 | Brendel et al. |
| 5,336,616 A | 8/1994 | Livesey et al. |
| 5,556,379 A | 9/1996 | Wolfinbarger |
| 5,753,506 A | 5/1998 | Johe |
| 5,820,581 A | 10/1998 | Wolfinbarger, Jr. |
| 5,976,104 A | 11/1999 | Wolfinbarger, Jr. |
| 6,376,244 B1 | 4/2002 | Atala |
| 6,379,963 B2 | 4/2002 | Haverich et al. |
| 6,416,995 B1 | 7/2002 | Wolfinbarger |
| 6,432,712 B1 | 8/2002 | Wolfinbarger, Jr. |
| 6,479,064 B1 | 11/2002 | Atala |
| 6,689,161 B2 | 2/2004 | Chen et al. |
| 6,749,064 B1 | 6/2004 | Alrey |
| 6,753,181 B2 | 6/2004 | Atala et al. |
| 6,767,738 B1 | 7/2004 | Gag et al. |
| 6,960,427 B2 | 11/2005 | Haverich et al. |
| 6,962,814 B2 | 11/2005 | Mitchell et al. |
| 7,015,037 B1 | 3/2006 | Furcht et al. |
| 7,311,904 B2 | 12/2007 | Hariri |
| 7,354,749 B2 | 4/2008 | Fisher et al. |
| 7,829,108 B2 | 11/2010 | Van et al. |
| 8,170,665 B2 | 5/2012 | Cohen et al. |
| 8,187,619 B2 | 5/2012 | Johnson |
| 8,470,520 B2 | 6/2013 | Ott et al. |
| 9,127,242 B2 | 9/2015 | Guertin et al. |
| 9,243,221 B2 | 1/2016 | Yarmush et al. |

(Continued)

FOREIGN PATENT DOCUMENTS

| | | |
|---|---|---|
| AU | 2006282783 A1 | 3/2007 |
| AU | 2006282783 B2 | 9/2013 |

(Continued)

OTHER PUBLICATIONS

Rijal et al. (Sci. Adv. 2017;3:16 pages). (Year: 2017).*
Joyce et al. (Archives of Plastic Surgery May 2015;42(3):341-345). (Year: 2015).*
"International Application Serial No. PCT/US2019/036942, International Preliminary Report on Patentability mailed Dec. 24, 2020", 8 pgs.
"International Application Serial No. PCT/US2019/036942, International Search Report mailed Sep. 5, 2019", 4 pgs.
"International Application Serial No. PCT/US2019/036942, Written Opinion mailed Sep. 5, 2019", 6 pgs.
"International Application Serial No. PCT/US2023/067672, International Search Report mailed Sep. 27, 2023", 3 pgs.

(Continued)

*Primary Examiner* — Ernst V Arnold
(74) *Attorney, Agent, or Firm* — Foley & Lardner LLP

(57) ABSTRACT

Disclosed herein are methods for retention of shape of decellularized tissue or of a portion of an organ can be accomplished through the irradiation of the decellularized tissue or the portion of the organ inside a shaping mold. The enclosure of decellularized tissue or a portion of an organ inside of a mold or other constraining material, such as stainless steel or platinum or polymers such as polytetrafluoroethylene (PTFE) or polycaprolactone (PCL), allows the tissue to take on the shape of the mold or constraint and subsequently retain that shape after it is irradiated. This can result in decellularized extracellular matrix having defined (pre-determined) shapes. The system can include a hollow device which contains the filler or plug. The system may be inserted into the fistula tract and the filler or plug may be deployed by pulling, pushing or otherwise expelling the filler or plug into the tract.

24 Claims, 1 Drawing Sheet

(56) References Cited

U.S. PATENT DOCUMENTS

| | | |
|---|---|---|
| 9,290,738 B2 | 3/2016 | Ross et al. |
| 9,334,479 B2 | 5/2016 | Herrera Sanchez et al. |
| 9,500,642 B2 | 11/2016 | Blackman et al. |
| 9,974,814 B2 | 5/2018 | Katane et al. |
| 10,004,586 B2 | 6/2018 | Derwin et al. |
| 10,213,525 B2 | 2/2019 | Ross |
| 10,220,056 B2 | 3/2019 | Ott et al. |
| 10,233,420 B2 | 3/2019 | Taylor et al. |
| 10,441,609 B2 | 10/2019 | Ott et al. |
| 10,709,813 B2 | 7/2020 | Griffiths et al. |
| 11,414,644 B2 | 8/2022 | Taylor et al. |
| 11,419,957 B2 | 8/2022 | Amoabediny et al. |
| 11,452,797 B2 | 9/2022 | Ross |
| 11,648,335 B2 | 5/2023 | Orlando et al. |
| 2001/0049138 A1 | 12/2001 | Dennis et al. |
| 2002/0081728 A1 | 6/2002 | Haverich et al. |
| 2002/0123143 A1 | 9/2002 | Toma et al. |
| 2003/0087428 A1 | 5/2003 | Wolfinbarger, Jr. et al. |
| 2003/0096407 A1 | 5/2003 | Atala et al. |
| 2003/0124099 A1 | 7/2003 | Atala et al. |
| 2003/0215945 A1 | 11/2003 | Atala |
| 2003/0228692 A1 | 12/2003 | Goldstein et al. |
| 2004/0126879 A1 | 7/2004 | Schneider et al. |
| 2004/0176855 A1 | 9/2004 | Badylak |
| 2004/0187877 A1 | 9/2004 | Badylak et al. |
| 2004/0234972 A1 | 11/2004 | Owens et al. |
| 2005/0084512 A1 | 4/2005 | Denizeau et al. |
| 2005/0130300 A1 | 6/2005 | Shimada et al. |
| 2005/0164380 A1 | 7/2005 | Trisler et al. |
| 2005/0182349 A1 | 8/2005 | Linde et al. |
| 2005/0227353 A1 | 10/2005 | Mummery |
| 2005/0249816 A1 | 11/2005 | Atala et al. |
| 2006/0034930 A1 | 2/2006 | Khosravi et al. |
| 2006/0135991 A1 | 6/2006 | Kawaura et al. |
| 2007/0020610 A1 | 1/2007 | Sherley et al. |
| 2007/0059293 A1 | 3/2007 | Atala |
| 2008/0004657 A1 | 1/2008 | Obermiller et al. |
| 2008/0058956 A1 | 3/2008 | Badylak |
| 2008/0245374 A1 | 10/2008 | Agnew |
| 2009/0074732 A1 | 3/2009 | Badylak |
| 2009/0169525 A1 | 7/2009 | Anversa et al. |
| 2009/0180965 A1 | 7/2009 | Freyman et al. |
| 2009/0202977 A1 | 8/2009 | Ott et al. |
| 2010/0093066 A1 | 4/2010 | Taylor et al. |
| 2011/0011410 A1 | 1/2011 | Desai et al. |
| 2011/0059152 A1 | 3/2011 | Atala |
| 2011/0287071 A1 | 11/2011 | Mitrani |
| 2012/0028234 A1 | 2/2012 | Guertin et al. |
| 2012/0064537 A1 | 3/2012 | Ross |
| 2012/0183944 A1 | 7/2012 | Taylor et al. |
| 2013/0109088 A1 | 5/2013 | Ott et al. |
| 2013/0156744 A1 | 6/2013 | Taylor et al. |
| 2013/0158595 A1 | 6/2013 | Mavani et al. |
| 2013/0323708 A1 | 12/2013 | Yarmush et al. |
| 2013/0337560 A1 | 12/2013 | Ross et al. |
| 2013/0344599 A1 | 12/2013 | Ott et al. |
| 2014/0017664 A1 | 1/2014 | Kravitz et al. |
| 2014/0023723 A1 | 1/2014 | Leach et al. |
| 2015/0182560 A1 | 7/2015 | Calle et al. |
| 2015/0230453 A1 | 8/2015 | Fontes et al. |
| 2015/0297798 A1 | 10/2015 | Badylak et al. |
| 2015/0342177 A1 | 12/2015 | Hassanein et al. |
| 2016/0030637 A1 | 2/2016 | Ross et al. |
| 2016/0030638 A1 | 2/2016 | Ross et al. |
| 2016/0038128 A1 | 2/2016 | Carrison |
| 2016/0058534 A1 | 3/2016 | Derwin et al. |
| 2016/0279170 A1 | 9/2016 | Katane et al. |
| 2018/0064848 A1 | 3/2018 | Ross et al. |
| 2019/0284523 A1 | 9/2019 | Taylor et al. |
| 2019/0343877 A1 | 11/2019 | Ott et al. |
| 2019/0381212 A1 | 12/2019 | Ross |
| 2020/0222456 A1 | 7/2020 | Ott et al. |
| 2021/0315200 A1 | 10/2021 | Katane |
| 2022/0062349 A1 | 3/2022 | Taylor et al. |
| 2022/0088269 A1 | 3/2022 | Steiner et al. |
| 2022/0280695 A1 | 9/2022 | Katane et al. |
| 2023/0002723 A1 | 1/2023 | Taylor et al. |
| 2023/0293770 A1 | 9/2023 | Ross |

FOREIGN PATENT DOCUMENTS

| | | |
|---|---|---|
| AU | 2013224686 B2 | 6/2015 |
| AU | 2013257459 B2 | 9/2015 |
| CA | 2751133 A1 | 8/2010 |
| CA | 2757457 | 5/2018 |
| CA | 2809990 C | 3/2021 |
| CA | 2907144 C | 10/2022 |
| CN | 1615162 A | 5/2005 |
| CN | 101066477 A | 11/2007 |
| CN | 101272815 A | 9/2008 |
| CN | 101366978 A | 2/2009 |
| CN | 102388127 A | 3/2012 |
| CN | 102477172 A | 5/2012 |
| CN | 102639073 A | 8/2012 |
| CN | 101272815 B | 9/2012 |
| CN | 102861359 A | 1/2013 |
| CN | 102861359 B | 4/2015 |
| CN | 104703634 A | 6/2015 |
| CN | 104937094 A | 9/2015 |
| CN | 105164250 A | 12/2015 |
| CN | 103458935 B | 8/2016 |
| CN | 107635592 A | 1/2018 |
| CN | 118510391 A | 8/2024 |
| CN | 118510392 A | 8/2024 |
| EP | 1246903 A1 | 1/2008 |
| EP | 2431063 A2 | 3/2012 |
| EP | 1928519 B1 | 4/2012 |
| EP | 2431063 B1 | 6/2015 |
| EP | 2965769 A1 | 1/2016 |
| EP | 2968672 A1 | 1/2016 |
| EP | 2970891 A1 | 1/2016 |
| EP | 2611472 B1 | 2/2016 |
| EP | 2593116 B1 | 6/2016 |
| EP | 2965769 B1 | 12/2018 |
| EP | 2968672 B1 | 2/2019 |
| EP | 3274007 B1 | 9/2020 |
| EP | 2970891 B1 | 10/2020 |
| EP | 3509651 B1 | 12/2022 |
| ES | 2384721 T3 | 7/2012 |
| HK | 1170662 A | 3/2013 |
| HK | 1184813 A | 1/2014 |
| HK | 1187284 B | 8/2016 |
| HK | 1218929 A1 | 3/2017 |
| HK | 1220646 A1 | 5/2017 |
| IN | 11201DELNO2014 A | 2/2015 |
| IN | 5160DLLNP2014 A | 3/2015 |
| IN | 423280 | 2/2023 |
| JP | 551601 A | 2/1980 |
| JP | S5516016 A | 2/1980 |
| JP | S5516016 B2 | 4/1980 |
| JP | 06218036 A | 8/1994 |
| JP | 06261933 A | 9/1994 |
| JP | H06261933 A | 9/1994 |
| JP | 1176400 A | 3/1999 |
| JP | H1176400 A | 3/1999 |
| JP | 2000004870 A | 1/2000 |
| JP | 2001518008 A | 10/2001 |
| JP | 2003518517 A | 6/2003 |
| JP | 2004167236 A | 6/2004 |
| JP | 2005509495 A | 4/2005 |
| JP | 2007222391 A | 9/2007 |
| JP | 2008541717 A | 11/2008 |
| JP | 2009505752 A | 2/2009 |
| JP | 2009207700 A | 9/2009 |
| JP | 2012516699 A | 7/2012 |
| JP | 2012522511 A | 9/2012 |
| JP | 2013536738 A | 6/2013 |
| JP | 5516016 B2 | 4/2014 |
| JP | 2015094591 A | 5/2015 |
| JP | 2015164549 A | 9/2015 |
| JP | 2016039903 A | 3/2016 |
| JP | 2017038948 A | 2/2017 |
| JP | 608062 B2 | 3/2017 |
| JP | 2017195900 A | 11/2017 |

(56) References Cited

FOREIGN PATENT DOCUMENTS

| | | |
|---|---|---|
| JP | 2018512172 A | 5/2018 |
| JP | 2018515129 A | 6/2018 |
| JP | 2019031120 A | 2/2019 |
| JP | 6491187 B2 | 3/2019 |
| JP | 2019072524 A | 6/2019 |
| JP | 2019088910 A | 6/2019 |
| JP | 2019134723 A | 8/2019 |
| JP | 2019141661 A | 8/2019 |
| JP | 2020099344 A | 7/2020 |
| JP | 6781352 B2 | 10/2020 |
| JP | 2021120012 A | 8/2021 |
| JP | 2022516562 A | 2/2022 |
| JP | 2022107023 A | 7/2022 |
| JP | 2022545446 A | 10/2022 |
| JP | 7286708 B2 | 5/2023 |
| JP | 2024015176 A | 2/2024 |
| KR | 20120023626 A | 3/2012 |
| KR | 20160026839 A | 3/2016 |
| KR | 10-1900116 B1 | 9/2018 |
| KR | 20210090299 A | 7/2021 |
| KR | 102417995 B1 | 7/2022 |
| KR | 102577616 B1 | 9/2023 |
| MX | 343363 B | 11/2016 |
| MX | 350338 B | 9/2017 |
| MX | 359769 B | 10/2018 |
| RU | 2463081 C2 | 10/2012 |
| RU | 2011143730 A | 5/2013 |
| RU | 2611361 C2 | 2/2017 |
| RU | 2635478 C2 | 11/2017 |
| SG | 10201906304 T4 | 8/2019 |
| SG | 10201603074Q | 11/2020 |
| WO | WO-9608213 A1 | 3/1996 |
| WO | WO-19999049015 A2 | 9/1999 |
| WO | WO-0148153 A1 | 7/2001 |
| WO | WO-0149210 A1 | 7/2001 |
| WO | WO-0224244 A2 | 3/2002 |
| WO | WO-2002024244 A2 | 3/2002 |
| WO | WO-0240630 A2 | 5/2002 |
| WO | WO-0249681 A1 | 6/2002 |
| WO | WO-2002049681 A1 | 6/2002 |
| WO | WO-02063962 A1 | 8/2002 |
| WO | WO-2002063962 A1 | 8/2002 |
| WO | WO-03039610 A1 | 5/2003 |
| WO | WO-03043674 A1 | 5/2003 |
| WO | WO-2003039610 A1 | 5/2003 |
| WO | WO-2003043674 A1 | 5/2003 |
| WO | WO-03087292 A2 | 10/2003 |
| WO | WO-03087428 A1 | 10/2003 |
| WO | WO-2004054571 A1 | 7/2004 |
| WO | WO-2004080501 A1 | 9/2004 |
| WO | WO-2004100832 A1 | 11/2004 |
| WO | WO-2005063316 A1 | 7/2005 |
| WO | WO-2005118014 A2 | 12/2005 |
| WO | WO-2006033415 A1 | 3/2006 |
| WO | WO-2006042138 A2 | 4/2006 |
| WO | WO-2006122533 A2 | 11/2006 |
| WO | WO-2006126236 A1 | 11/2006 |
| WO | WO-2007025233 A1 | 3/2007 |
| WO | WO-2010086856 A2 | 8/2010 |
| WO | WO-2010120539 | 10/2010 |
| WO | WO-2010120539 A1 | 10/2010 |
| WO | WO-2010120539 A2 | 10/2010 |
| WO | WO-2011002926 A2 | 1/2011 |
| WO | WO-2010120539 A3 | 2/2011 |
| WO | WO-2011031484 A2 | 3/2011 |
| WO | WO-2011059808 A2 | 5/2011 |
| WO | WO-2011066522 A2 | 6/2011 |
| WO | WO-2012003450 A2 | 1/2012 |
| WO | WO-2012005760 A1 | 1/2012 |
| WO | WO-2012031162 A1 | 3/2012 |
| WO | WO-2012101181 A1 | 8/2012 |
| WO | WO-2013016544 A2 | 1/2013 |
| WO | WO-2013071096 A1 | 5/2013 |
| WO | WO-2013127540 A1 | 9/2013 |
| WO | 2013158283 A1 | 10/2013 |
| WO | 2013188525 A1 | 12/2013 |
| WO | WO-2014013241 A1 | 1/2014 |
| WO | WO-2014059316 A1 | 4/2014 |
| WO | WO-2014151739 A1 | 9/2014 |
| WO | WO-2014168719 A1 | 10/2014 |
| WO | WO-2014168719 A8 | 10/2014 |
| WO | WO-2015138999 A1 | 9/2015 |
| WO | WO-2016033337 A1 | 3/2016 |
| WO | WO-2016154447 A1 | 9/2016 |
| WO | WO-2017123883 A1 | 7/2017 |
| WO | WO-2017175870 A1 | 10/2017 |
| WO | WO-2017223529 A1 * | 12/2017 ............ A61K 35/12 |
| WO | WO-2018013849 A1 | 1/2018 |
| WO | WO-2018015548 A2 | 1/2018 |
| WO | WO-2018048899 A1 | 3/2018 |
| WO | WO-2018048899 A8 | 3/2018 |
| WO | WO-2019188806 A1 | 10/2019 |
| WO | WO-2019/241499 A1 | 12/2019 |
| WO | WO-2019245640 A1 | 12/2019 |
| WO | WO-2020146391 A1 | 7/2020 |
| WO | WO-2021034911 A1 | 2/2021 |
| WO | WO-2023069930 A1 | 4/2023 |
| WO | WO-2023069939 A1 | 4/2023 |

OTHER PUBLICATIONS

"International Application Serial No. PCT/US2023/067672, Written Opinion mailed Sep. 27, 2023", 8 pgs.
"U.S. Appl. No. 13/787,625 Examiner Interview summary mailed Sep. 25, 2015", 1 pg.
"U.S. Appl. No. 11/512,009, Final Office Action mailed Jun. 3, 2009", 11 pgs.
"U.S. Appl. No. 11/512,009, Final Office Action mailed Jul. 15, 2010", 10 pgs.
"U.S. Appl. No. 11/512,009, Non Final Office Action mailed Feb. 1, 2010", 10 pgs.
"U.S. Appl. No. 11/512,009, Non Final Office Action mailed Aug. 29, 2008", 12 pgs.
"U.S. Appl. No. 11/512,009, Response filed Dec. 7, 2009 to Final Office Action mailed Jun. 3, 2009", 8 pgs.
"U.S. Appl. No. 11/512,009, Response filed Mar. 2, 2009 to Non Final Office Action mailed Aug. 29, 2008", 9 pgs.
"U.S. Appl. No. 11/512,009, Response filed May 27, 2008 to Restriction Requirement mailed Apr. 11, 2008", 1 pg.
"U.S. Appl. No. 11/512,009, Response filed May 3, 2010 to Non Final Office Action mailed Feb. 1, 2010", 7 pgs.
"U.S. Appl. No. 11/512,009, Restriction Requirement mailed Apr. 11, 2008", 7 pgs.
"U.S. Appl. No. 12/064,613 , Response filed Apr. 5, 2013 to Final Office Action mailed Feb. 7, 2013", 11 pgs.
"U.S. Appl. No. 12/064,613, Declaration of Dr. Doris Taylor filed Jan. 26, 2012", 4 pgs.
"U.S. Appl. No. 12/064,613, Declaration of Dr. Jeffrey Ross filed Mar. 4, 2013", 8 pgs.
"U.S. Appl. No. 12/064,613, Examiner Interview Summary mailed Mar. 7, 2013", 3 pgs.
"U.S. Appl. No. 12/064,613, Examiner Interview Summary mailed Apr. 5, 2013", 4 pgs.
"U.S. Appl. No. 12/064,613, Examiner Interview Summary mailed Jun. 20, 2012", 3 pgs.
"U.S. Appl. No. 12/064,613, Examiner Interview Summary mailed Jul. 13, 2012", 3 pgs.
"U.S. Appl. No. 12/064,613, Examiner Interview Summary mailed Jul. 18, 2012", 3 pgs.
"U.S. Appl. No. 12/064,613, Final Office Action mailed Feb. 7, 2013", 16 pgs.
"U.S. Appl. No. 12/064,613, Final Office Action mailed Apr. 6, 2012", 10 pgs.
"U.S. Appl. No. 12/064,613, Non Final Office Action mailed Aug. 30, 2012", 18 pgs.
"U.S. Appl. No. 12/064,613, Non Final Office Action mailed Sep. 29, 2011", 8 pgs.
"U.S. Appl. No. 12/064,613, Notice of Allowance mailed May 1, 2013", 11 pgs.

(56) References Cited

OTHER PUBLICATIONS

"U.S. Appl. No. 12/064,613, Preliminary Amendment filed Feb. 22, 2008", 8 pgs.
"U.S. Appl. No. 12/064,613, Response filed Jan. 27, 2012 to Non Final Office Action mailed Sep. 29, 2011", 10 pgs.
"U.S. Appl. No. 12/064,613, Response filed Jul. 16, 2012 to Final Office Action mailed Apr. 6, 2012", 12 pgs.
"U.S. Appl. No. 12/064,613, Response filed Jul. 21, 2011 to Restriction Requirement mailed Jun. 29, 2011", 9 pgs.
"U.S. Appl. No. 12/064,613, Response filed Dec. 4,2012 to Non Final Office Action mailed Aug. 30, 2012", 11 pgs.
"U.S. Appl. No. 12/064,613, Restriction Requirement mailed Jun. 29, 2011", 8 pgs.
"U.S. Appl. No. 12/547,021, Final Office Action mailed May 14, 2012", 11 pgs.
"U.S. Appl. No. 12/547,021, Non Final Office Action mailed Dec. 14, 2011", 11 pgs.
"U.S. Appl. No. 12/547,021, Response filed Mar. 14, 2012 to Non Final Office Action mailed Dec. 14, 2011", 9 pgs.
"U.S. Appl. No. 13/173,400, Examiner Interview Summary mailed Sep. 1, 2015", 1 pg.
"U.S. Appl. No. 13/173,400, Advisory Action mailed Sep. 1, 2015", 5 pgs.
"U.S. Appl. No. 13/173,400, Advisory Action mailed Nov. 3, 2017", 3 pgs.
"U.S. Appl. No. 13/173,400, Examiner Interview Summary mailed Aug. 5, 2015", 3 pgs.
"U.S. Appl. No. 13/173,400, Final Office Action mailed Mar. 26, 2013", 21 pgs.
"U.S. Appl. No. 13/173,400, Final Office Action mailed Apr. 23, 2015", 17 pgs.
"U.S. Appl. No. 13/173,400, Final Office Action mailed Jun. 1, 2017", 17 pgs.
"U.S. Appl. No. 13/173,400, Final Office Action mailed Jun. 4, 2018", 22 pgs.
"U.S. Appl. No. 13/173,400, Final Office Action mailed Aug. 5, 2016", 35 pgs.
"U.S. Appl. No. 13/173,400, Non Final Office Action mailed Sep. 2, 2014", 20 pgs.
"U.S. Appl. No. 13/173,400, Non Final Office Action mailed Oct. 1, 2012", 17 pgs.
"U.S. Appl. No. 13/173,400, Non Final Office Action mailed Dec. 3, 2015", 35 pgs.
"U.S. Appl. No. 13/173,400, Non Final Office Action mailed Dec. 21, 2017", 18 pgs.
"U.S. Appl. No. 13/173,400, Non Final Office Action mailed Dec. 22, 2016", 16 pgs.
"U.S. Appl. No. 13/173,400, Preliminary Amendment filed Nov. 21, 2011", 3 pgs.
"U.S. Appl. No. 13/173,400, Response filed Jan. 2, 2014 to Non Final Office Action mailed Oct. 1, 2012", 10 pgs.
"U.S. Appl. No. 13/173,400, Response filed Feb. 2, 2015 to Non Final Office Action mailed Sep. 2, 2014", 8 pgs.
"U.S. Appl. No. 13/173,400, Response filed Mar. 22, 2017 to Non Final Office Action mailed Dec. 22, 2016", 10 pgs.
"U.S. Appl. No. 13/173,400, Response filed Apr. 18, 2018 to Non Final Office Action mailed Dec. 21, 2017", 10 pgs.
"U.S. Appl. No. 13/173,400, Response filed Jun. 20, 2013 to Final Office Action mailed Mar. 26, 2013", 10 pgs.
"U.S. Appl. No. 13/173,400, Response filed Aug. 10, 2015 to Final Office Action mailed Apr. 23, 2015", 10 pgs.
"U.S. Appl. No. 13/173,400, Response filed Oct. 2, 2017 to Final Office Action mailed Jun. 1, 2017", 9 pgs.
"U.S. Appl. No. 13/173,400, Response filed Nov. 29, 2017 to Advisory Action mailed Nov. 3, 2017", 9 pgs.
"U.S. Appl. No. 13/173,400, Response filed Dec. 5, 2016 to Final Office Action mailed Aug. 5, 2016", 13 pgs.
"U.S. Appl. No. 13/262,286, Advisory Action mailed Jun. 27, 2017", 3 pgs.
"U.S. Appl. No. 13/262,286, Final Office Action mailed Jan. 11, 2019", 9 pgs.
"U.S. Appl. No. 13/262,286, Final Office Action mailed Mar. 9, 2017", 8 pgs.
"U.S. Appl. No. 13/262,286, Final Office Action mailed Jun. 11, 2015", 6 pgs.
"U.S. Appl. No. 13/262,286, Final Office Action mailed Jul. 10, 2020", 12 pgs.
"U.S. Appl. No. 13/262,286, Final Office Action mailed Aug. 14, 2013", 9 pgs.
"U.S. Appl. No. 13/262,286, Non Final Office Action mailed Mar. 29, 2018", 10 pgs.
"U.S. Appl. No. 13/262,286, Non Final Office Action mailed Jun. 10, 2016", 8 pgs.
"U.S. Appl. No. 13/262,286, Non Final Office Action mailed Oct. 9, 2014", 7 pgs.
"U.S. Appl. No. 13/262,286, Non Final Office Action mailed Dec. 14, 2012", 11 pgs.
"U.S. Appl. No. 13/262,286, Non-Final Office Action mailed Aug. 9, 2019", 11 pgs.
"U.S. Appl. No. 13/262,286, Preliminary Amendment filed Aug. 17, 2012", 4 pgs.
"U.S. Appl. No. 13/262,286, Preliminary Amendment filed Sep. 30, 2011", 3 pgs.
"U.S. Appl. No. 13/262,286, Response filed Feb. 10, 2020 to Non Final Office Action mailed Aug. 9, 2019", 12 pgs.
"U.S. Appl. No. 13/262,286, Response filed Feb. 14, 2014 to Final Office Action mailed Aug. 14, 2013", 7 pgs.
"U.S. Appl. No. 13/262,286, Response filed Mar. 9, 2015 to Non Final Office Action mailed Oct. 9, 2014", 7 pgs.
"U.S. Appl. No. 13/262,286, Response filed Jun. 9, 2017 to Final Office Action mailed Mar. 9, 2017", 8 pgs.
"U.S. Appl. No. 13/262,286, Response filed Jun. 10, 2013 to Non Final Office Action mailed Dec. 14, 2012", 7 pgs.
"U.S. Appl. No. 13/262,286, Response filed Jul. 11, 2019 to Final Office Action mailed Jan. 11, 2019", 13 pgs.
"U.S. Appl. No. 13/262,286, Response filed Sep. 28, 2018 to Non Final Office Action mailed Mar. 29, 2018", 13 pgs.
"U.S. Appl. No. 13/262,286, Response filed Nov. 30, 2012 to Restriction Requirement mailed Oct. 30, 2012", 8 pgs.
"U.S. Appl. No. 13/262,286, Response filed Dec. 7, 2015 to Final Office Action mailed Jun. 11, 2015", 8 pgs.
"U.S. Appl. No. 13/262,286, Response filed Dec. 8, 2016 to Non Final Office Action mailed Jun. 10, 2016", 7 pgs.
"U.S. Appl. No. 13/262,286, Restriction Requirement mailed Oct. 30, 2012", 8 pgs.
"U.S. Appl. No. 13/713,710, Response filed Aug. 25, 2015 to Restriction Requirement mailed Jul. 2, 2015", 7 pgs.
"U.S. Appl. No. 13/725,030, Advisory Action mailed Jun. 5, 2014", 3 pgs.
"U.S. Appl. No. 13/725,030, Applicant's Summary of Examiner Interview filed 06-20, 2019", 2 pgs.
"U.S. Appl. No. 13/725,030, Examiner Interview Summary mailed Jan. 22, 2015", 4 pgs.
"U.S. Appl. No. 13/725,030, Examiner Interview Summary mailed Jan. 29, 2016", 5 pgs.
"U.S. Appl. No. 13/725,030, Examiner Interview Summary mailed Mar. 6, 2015", 3 pgs.
"U.S. Appl. No. 13/725,030, Examiner Interview Summary mailed May 6, 2014", 3 pgs.
"U.S. Appl. No. 13/725,030, Examiner Interview Summary mailed Jun. 7, 2019", 2 pgs.
"U.S. Appl. No. 13/725,030, Examiner Interview Summary mailed Jun. 25, 2018", 3 pgs.
"U.S. Appl. No. 13/725,030, Examiner Interview Summary mailed Jun. 29, 2015", 3 pgs.
"U.S. Appl. No. 13/725,030, Final Office Action mailed Mar. 17, 2014", 14 pgs.
"U.S. Appl. No. 13/725,030, Final Office Action mailed May 19, 2015", 23 pgs.
"U.S. Appl. No. 13/725,030, Final Office Action mailed Jun. 23, 2016", 22 pgs.

(56) References Cited

OTHER PUBLICATIONS

"U.S. Appl. No. 13/725,030, Final Office Action mailed Sep. 13, 2017", 20 pgs.
"U.S. Appl. No. 13/725,030, Final Office Action mailed Sep. 13, 2018", 23 pgs.
"U.S. Appl. No. 13/725,030, Non Final Office Action mailed Jan. 6, 2017", 28 pgs.
"U.S. Appl. No. 13/725,030, Non Final Office Action mailed Jan. 29, 2018", 19 pgs.
"U.S. Appl. No. 13/725,030, Non Final Office Action mailed Jul. 5, 2013", 12 pgs.
"U.S. Appl. No. 13/725,030, Non Final Office Action mailed Oct. 2, 2015", 31 pgs.
"U.S. Appl. No. 13/725,030, Non Final Office Action mailed Dec. 5, 2014", 19 pgs.
"U.S. Appl. No. 13/725,030, Notice of Allowance mailed Jun. 3, 2019", 13 pgs.
"U.S. Appl. No. 13/725,030, Preliminary Amendment filed Dec. 21, 2012", 6 pgs.
"U.S. Appl. No. 13/725,030, Response filed Jan. 2, 2014 to Non Final Office Action mailed Jul. 5, 2013", 10 pgs.
"U.S. Appl. No. 13/725,030, Response filed Mar. 4, 2015 to Non Final Office Action mailed Dec. 5, 2014", 14 pgs.
"U.S. Appl. No. 13/725,030, Response filed Mar. 13, 2019 to Final Office Action mailed Sep. 13, 2018", 16 pgs.
"U.S. Appl. No. 13/725,030, Response filed Apr. 1, 2016 to Non Final Office Action mailed Oct. 2, 2015", 23 pgs.
"U.S. Appl. No. 13/725,030, Response filed May 19, 2014 to Final Office Action mailed Mar. 17, 2014", 11 pgs.
"U.S. Appl. No. 13/725,030, Response filed Jun. 5, 2013 to Restriction Requirement mailed Apr. 5, 2013", 7 pgs.
"U.S. Appl. No. 13/725,030, Response filed Jun. 17, 2014 to Advisory Action mailed Jun. 5, 2014", 15 pgs.
"U.S. Appl. No. 13/725,030, Response filed Jun. 28, 2018 to Non Final Office Action mailed Jan. 29, 2018", 15 pgs.
"U.S. Appl. No. 13/725,030, Response filed Jul. 6, 2017 to Non Final Office Action mailed Jan. 6, 2017", 16 pgs.
"U.S. Appl. No. 13/725,030, Response filed Aug. 25, 2015 to Final Office Action mailed May 19, 2015", 21 pgs.
"U.S. Appl. No. 13/725,030, Response filed Nov. 23, 2016 to Final Office Action mailed Jun. 23, 2016", 14 pgs.
"U.S. Appl. No. 13/725,030, Response filed Nov. 23, 2016 Final Office Action mailed Jun. 23, 2016", 14 pgs.
"U.S. Appl. No. 13/725,030, Response filed Dec. 12, 2017 to Final Office Action mailed Sep. 13, 2017", 17 pgs.
"U.S. Appl. No. 13/725,030, Restriction Requirement mailed Apr. 5, 2013", 9 pgs.
"U.S. Appl. No. 13/787,625 Examiner Interview Summary mailed Aug. 21, 2015", 1 pg.
"U.S. Appl. No. 13/787,625, Advisory Action mailed Aug. 21, 2015", 3 pgs.
"U.S. Appl. No. 13/787,625, Examiner Interview Summary mailed Jan. 29, 2016", 3 pgs.
"U.S. Appl. No. 13/787,625, Final Office Action mailed Apr. 1, 2015", 10 pgs.
"U.S. Appl. No. 13/787,625, Non Final Office Action mailed Jan. 9, 2014", 12 pgs.
"U.S. Appl. No. 13/787,625, Non Final Office Action mailed Jul. 10, 2014", 10 pgs.
"U.S. Appl. No. 13/787,625, Notice of Allowance mailed Sep. 25, 2015", 10 pgs.
"U.S. Appl. No. 13/787,625, Notice of Allowance mailed Nov. 13, 2015", 7 pgs.
"U.S. Appl. No. 13/787,625, Response filed Apr. 9, 2014 to Non Final Office Action mailed Jan. 9, 2014", 7 pgs.
"U.S. Appl. No. 13/787,625, Response filed Aug. 4, 2015 to Final Office Action mailed Apr. 1, 2015", 7 pgs.
"U.S. Appl. No. 13/787,625, Response filed Oct. 27, 2014 to Non Final Office Action mailed Jul. 10, 2014", 7 pgs.
"U.S. Appl. No. 13/787,625, Response filed Nov. 18, 2013 to Restriction Requirement mailed Oct. 18, 2013", 6 pgs.
"U.S. Appl. No. 13/787,625, Restriction Requirement mailed Oct. 18, 2013", 6 pgs.
"U.S. Appl. No. 13/820,079, Advisory Action mailed Aug. 13, 2015", 3 pgs.
"U.S. Appl. No. 13/820,079, AFCP 2.0 Decision mailed Oct. 29, 2018", 1 pg.
"U.S. Appl. No. 13/820,079, Examiner Interview Summary mailed Sep. 28, 2015", 3 pgs.
"U.S. Appl. No. 13/820,079, Final Office Action mailed Apr. 23, 2015", 15 pgs.
"U.S. Appl. No. 13/820,079, Final Office Action mailed May 30, 2018", 16 pgs.
"U.S. Appl. No. 13/820,079, Final Office Action mailed Nov. 21, 2016", 16 pgs.
"U.S. Appl. No. 13/820,079, Non Final Office Action mailed May 31, 2016", 15 pgs.
"U.S. Appl. No. 13/820,079, Non Final Office Action mailed Oct. 23, 2014", 14 pgs.
"U.S. Appl. No. 13/820,079, Non Final Office Action mailed Nov. 1, 2017", 18 pgs.
"U.S. Appl. No. 13/820,079, Notice of Allowance dated Oct. 29, 2018", 10 pgs.
"U.S. Appl. No. 13/820,079, Notice of Allowance mailed Oct. 29, 2018", 10 pgs.
"U.S. Appl. No. 13/820,079, Preliminary Amendment filed Feb. 28, 2013", 8 pgs.
"U.S. Appl. No. 13/820,079, Response filed Jan. 22, 2015 to Non Final Office Action mailed Oct. 23, 2014", 10 pgs.
"U.S. Appl. No. 13/820,079, Response filed Mar. 1, 2018 to Non Final Office Action mailed Nov. 1, 2017", 9 pgs.
"U.S. Appl. No. 13/820,079, Response filed May 18, 2017 to Final Office Action mailed Nov. 21, 2016", 11 pgs.
"U.S. Appl. No. 13/820,079, Response filed Jul. 23, 2015 to Final Office Action mailed Apr. 23, 2015", 10 pgs.
"U.S. Appl. No. 13/820,079, Response filed Aug. 30, 2016 to Non Final Office Action mailed May 31, 2016", 8 pgs.
"U.S. Appl. No. 13/820,079, Response filed Sep. 23, 2015 to Final Office Action mailed Apr. 23, 2015", 10 pgs.
"U.S. Appl. No. 13/820,079, Response Filed Sep. 27, 2018 to Final Office Action mailed May 30, 2018", 10 pgs.
"U.S. Appl. No. 13/820,079, Response filed Dec. 26, 2013 to Restriction Requirement mailed Oct. 25, 2013", 9 pgs.
"U.S. Appl. No. 13/820,079, Restriction Requirement mailed Oct. 25, 2013", 9 pgs.
"U.S. Appl. No. 13/913,974, Applicant's Summary of Examiner Interview filed Dec. 18, 2018.", 1 pg.
"U.S. Appl. No. 13/913,974, Applicant-Initiated Interview Summary mailed Dec. 13, 2018", 1 pg.
"U.S. Appl. No. 13/913,974, Applicant's Summary of Examiner Interview filed Nov. 27, 2018", 1 pg.
"U.S. Appl. No. 13/913,974, Declaration of Dr. Jeffrey Ross dated Feb. 23, 16 and filed Feb. 24, 2016", 5 pgs.
"U.S. Appl. No. 13/913,974, Examiner Interview Summary mailed Jan. 29, 2016", 3 pgs.
"U.S. Appl. No. 13/913,974, Examiner Interview Summary mailed Mar. 2, 2017", 3 pgs.
"U.S. Appl. No. 13/913,974, Examiner Interview Summary mailed Jun. 25, 2018", 3 pgs.
"U.S. Appl. No. 13/913,974, Examiner Interview Summary mailed Nov. 5, 2018", 3 pgs.
"U.S. Appl. No. 13/913,974, Examiner Interview Summary mailed Dec. 10, 2018", 3 pgs.
"U.S. Appl. No. 13/913,974, Final Office Action mailed May 4, 2016", 20 pgs.
"U.S. Appl. No. 13/913,974, Final Office Action mailed Jun. 15, 2017", 14 pgs.
"U.S. Appl. No. 13/913,974, Final Office Action mailed Jun. 15, 2017", 16 pgs.
"U.S. Appl. No. 13/913,974, Non Final Office Action mailed Aug. 24, 2015", 12 pgs.

(56) References Cited

OTHER PUBLICATIONS

"U.S. Appl. No. 13/913,974, Non Final Office Action Mailed Nov. 17, 2016", 16 pgs.
"U.S. Appl. No. 13/913,974, Non Final Office Action mailed Dec. 28, 2017", 19 pgs.
"U.S. Appl. No. 13/913,974, Notice of Allowance mailed Dec. 13, 2018", 12 pgs.
"U.S. Appl. No. 13/913,974, Notice of Non-Compliant Amendment mailed Sep. 13, 2018", 3 pgs.
"U.S. Appl. No. 13/913,974, Preliminary Amendment filed Jun. 11, 2013", 6 pgs.
"U.S. Appl. No. 13/913,974, Response filed Feb. 24, 2016 to Non Final Office Action mailed Aug. 24, 2015", 10 pgs.
"U.S. Appl. No. 13/913,974, Response filed May 17, 2017 to Non Final Office Action mailed Nov. 17, 2016", 9 pgs.
"U.S. Appl. No. 13/913,974, Response filed Jun. 27, 2018 to Non Final Office Action mailed Dec. 28, 2017", 8 pgs.
"U.S. Appl. No. 13/913,974, Response filed Aug. 11, 2015 to Restriction Requirement mailed Jun. 11, 2015", 7 pgs.
"U.S. Appl. No. 13/913,974, Response filed May 17, 2017 to Non Final Office Action mailed Nov. 17, 2017", 9 pgs.
"U.S. Appl. No. 13/913,974, Response filed Dec. 13, 2017 to Final Office Action mailed Jun. 15, 2017", 9 pgs.
"U.S. Appl. No. 13/913,974, Restriction Requirement mailed Jun. 11, 2015", 8 pgs.
"U.S. Appl. No. 14/777,360 Preliminary Amendment filed Sep. 15, 2015", 7 pgs.
"U.S. Appl. No. 14/777,360, Advisory Action mailed Apr. 30, 2018", 4 pgs.
"U.S. Appl. No. 14/777,360, Applicant's Summary of Examiner Interview filed Oct. 24, 2018", 1 pgs.
"U.S. Appl. No. 14/777,360, Ex Parte Quayle Action mailed Aug. 16, 2018", 5 pgs.
"U.S. Appl. No. 14/777,360, Final Office Action mailed Jan. 16, 2018", 8 pgs.
"U.S. Appl. No. 14/777,360, Non Final Office Action mailed Aug. 7, 2017", 8 pgs.
"U.S. Appl. No. 14/777,360, Notice of Allowance mailed Oct. 11, 2018", 9 pgs.
"U.S. Appl. No. 14/777,360, Response filed Apr. 16, 2018 to Final Office Action mailed Jan. 16, 2018", 8 pgs.
"U.S. Appl. No. 14/777,360, Response filed Jun. 7, 2017 to Restriction Requirement mailed Mar. 9, 2017", 7 pgs.
"U.S. Appl. No. 14/777,360, Response filed Jul. 16, 2018 to Advisory Action mailed Apr. 30, 2018", 12 pgs.
"U.S. Appl. No. 14/777,360, Response filed Nov. 7, 2017 to Non Final Office Action mailed Aug. 7, 2017", 7 pgs.
"U.S. Appl. No. 14/777,360, Restriction Requirement mailed Mar. 9, 2017", 7 pgs.
"U.S. Appl. No. 14/777,397 Preliminary Amendment filed Sep. 15, 2015", 7 pgs.
"U.S. Appl. No. 14/777,397, Final Office Action mailed Feb. 22, 2018", 9 pgs.
"U.S. Appl. No. 14/777,397, Non Final Office Action mailed Jun. 12, 2017", 8 pgs.
"U.S. Appl. No. 14/777,397, Response filed Oct. 12, 2017 to Non Final Office Action mailed Jun. 12, 2017", 7 pgs.
"U.S. Appl. No. 15/079,985, Non Final Office Action mailed Aug. 15, 2017", 7 pgs.
"U.S. Appl. No. 15/079,985, Notice of Allowance mailed Jan. 30, 2018", 7 pgs.
"U.S. Appl. No. 15/079,985, Response filed Jul. 24, 2017 to Restriction Requirement mailed May 23, 2017", 7 pgs.
"U.S. Appl. No. 15/079,985, Response filed Dec. 15, 2017 to Non Final Office Action mailed Aug. 15, 2017", 7 pgs.
"U.S. Appl. No. 15/079,985, Restriction Requirement mailed May 23, 2017", 7 pgs.
"U.S. Appl. No. 16/243,592, Final Office Action mailed Oct. 26, 2021", 14 pgs.
"U.S. Appl. No. 16/243,592, Non Final Office Action mailed Jun. 14, 2021", 13 pgs.
"U.S. Appl. No. 16/243,592, Notice of Allowance mailed Feb. 22, 2022", 10 pgs.
"U.S. Appl. No. 16/243,592, Notice of Allowance mailed May 10, 2022", 7 pgs.
"U.S. Appl. No. 16/243,592, Preliminary Amendment filed Feb. 12, 2020", 7 pgs.
"U.S. Appl. No. 16/243,592, Preliminary Amendment filed Sep. 6, 2019", 5 pgs.
"U.S. Appl. No. 16/243,592, Response filed Jan. 26, 2022 to Final Office Action mailed Oct. 26, 2021", 7 pgs.
"U.S. Appl. No. 16/243,592, Response filed Mar. 11, 2021 to Restriction Requirement mailed Sep. 24, 2020", 6 pgs.
"U.S. Appl. No. 16/243,592, Response filed Oct. 14, 2021 to Non Final Office Action mailed Jun. 14, 2021", 7 pgs.
"U.S. Appl. No. 16/243,592, Restriction Requirement mailed Sep. 24, 2020", 5 pgs.
"U.S. Appl. No. 16/245,435, Final Office Action mailed Jan. 5, 2023", 18 pgs.
"U.S. Appl. No. 16/245,435, Non Final Office Action mailed Jul. 22, 2022", 15 pgs.
"U.S. Appl. No. 16/245,435, Preliminary Amendment filed Jan. 11, 2019", 3 pgs.
"U.S. Appl. No. 16/245,435, Response filed May 13, 2022 to Restriction Requirement mailed Nov. 15, 2021", 8 pgs.
"U.S. Appl. No. 16/245,435, Response filed Oct. 19, 2022 to Non Final Office Action mailed Jul. 22, 2022", 9 pgs.
"U.S. Appl. No. 16/245,435, Restriction Requirement mailed Nov. 15, 2021", 31 pgs.
"U.S. Appl. No. 16/245,435, Supplemental Preliminary Amendment filed Aug. 6, 2019", 7 pgs.
"U.S. Appl. No. 16/260,997, Advisory Action mailed Aug. 31, 2021", 3 pgs.
"U.S. Appl. No. 16/260,997, Corrected Notice of Allowability mailed May 9, 2022", 6 pgs.
"U.S. Appl. No. 16/260,997, Examiner Interview Summary mailed Jan. 27, 2022", 2 pgs.
"U.S. Appl. No. 16/260,997, Final Office Action mailed May 14, 2021", 20 pgs.
"U.S. Appl. No. 16/260,997, Non Final Office Action mailed Oct. 22, 2021", 21 pgs.
"U.S. Appl. No. 16/260,997, Non Final Office Action mailed Dec. 14, 2020", 14 pgs.
"U.S. Appl. No. 16/260,997, Notice of Allowance mailed Apr. 6, 2022", 9 pgs.
"U.S. Appl. No. 16/260,997, Response filed Mar. 1, 2022 to Non Final Office Action mailed Oct. 22, 2021", 11 pgs.
"U.S. Appl. No. 16/260,997, Response filed Mar. 9, 2021 to Non Final Office Action mailed Dec. 14, 2020", 8 pgs.
"U.S. Appl. No. 16/260,997, Response filed Aug. 16, 2021 to Final Office Action mailed May 14, 2021", 9 pgs.
"U.S. Appl. No. 16/554,792, Advisory Action mailed May 24, 2024", 3 pgs.
"U.S. Appl. No. 16/554,792, Examiner Interview Summary mailed Jul. 25, 2023", 2 pgs.
"U.S. Appl. No. 16/554,792, Final Office Action mailed Feb. 12, 2024", 13 pgs.
"U.S. Appl. No. 16/554,792, Non Final Office Action mailed Feb. 2, 2023", 17 pgs.
"U.S. Appl. No. 16/554,792, Non Final Office Action mailed Sep. 6, 2024", 21 pgs.
"U.S. Appl. No. 16/554,792, Preliminary Amendment filed Apr. 3, 2020", 12 pgs.
"U.S. Appl. No. 16/554,792, Preliminary Amendment filed Aug. 29, 2019", 3 pgs.
"U.S. Appl. No. 16/554,792, Response filed May 13, 2024 to Final Office Action mailed Feb. 12, 2024", 11 pgs.
"U.S. Appl. No. 16/554,792, Response filed Jul. 11, 2024 to Advisory Action mailed May 4, 2024", 12 pgs.
"U.S. Appl. No. 16/554,792, Response filed Aug. 1, 2023 to Non Final Office Action mailed Feb. 2, 2023", 13 pgs.

(56) References Cited

OTHER PUBLICATIONS

"U.S. Appl. No. 16/554,792, Response filed Aug. 17, 2022 to Restriction Requirement mailed Feb. 17, 2022", 13 pgs.
"U.S. Appl. No. 16/554,792, Response filed Nov. 22, 2023 to Restriction Requirement mailed Oct. 18, 2023", 9 pgs.
"U.S. Appl. No. 16/554,792, Response filed Nov. 23, 2022 to Restriction Requirement mailed Feb. 17, 2022", 13 pgs.
"U.S. Appl. No. 16/554,792, Restriction Requirement mailed Feb. 17, 2022", 18 pgs.
"U.S. Appl. No. 16/554,792, Restriction Requirement mailed Oct. 18, 2023", 12 pgs.
"Application Serial No. 16730926.9, Response filed May 15, 2018 to Office Action mailed Nov. 6, 2017", 31 pgs.
"U.S. Appl. No. 17/228,968, Advisory Action mailed Jul. 12, 2024", 4 pgs.
"U.S. Appl. No. 17/228,968, Examiner Interview Summary mailed Nov. 20, 2023", 4 pgs.
"U.S. Appl. No. 17/228,968, Final Office Action mailed Mar. 13, 2024", 39 pgs.
"U.S. Appl. No. 17/228,968, Non Final Office Action mailed Aug. 28, 2024", 38 pgs.
"U.S. Appl. No. 17/228,968, Non Final Office Action mailed Aug. 31, 2023", 33 pgs.
"U.S. Appl. No. 17/228,968, Response filed Jan. 2, 2024 to Non Final Office Action mailed Aug. 31, 2023", 14 pgs.
"U.S. Appl. No. 17/228,968, Response filed Jun. 13, 2024 to Final Office Action mailed Mar. 13, 2024", 17 pgs.
"U.S. Appl. No. 17/394,243, Final Office Action mailed Jul. 19, 2024", 17 pgs.
"U.S. Appl. No. 17/394,243, Non Final Office Action mailed Sep. 28, 2023", 14 pgs.
"U.S. Appl. No. 17/394,243, Response filed Mar. 15, 2024 to Non Final Office Action mailed Sep. 28, 2023", 15 pgs.
"U.S. Appl. No. 17/394,243, Supplemental Preliminary Amendment Filed Nov. 18, 2021", 4 pgs.
"U.S. Appl. No. 17/420,099, Final Office Action mailed Aug. 30, 2024", 11 pgs.
"U.S. Appl. No. 17/420,099, Non Final Office Action mailed Apr. 30, 2024", 10 pgs.
"U.S. Appl. No. 17/420,099, Preliminary Amendment Filed Jun. 30, 2021", 6 pgs.
"U.S. Appl. No. 17/420,099, Response filed Jul. 30, 2024 to Non Final Office Action mailed Apr. 30, 2024", 7 pgs.
"U.S. Appl. No. 17/636,687, Preliminary Amendment Filed Feb. 18, 2022", 7 pgs.
"U.S. Appl. No. 17/636,687, Restriction Requirement mailed Sep. 20, 2024", 7 pgs.
"U.S. Appl. No. 17/820,391, Supplemental Preliminary Amendment filed Jun. 14, 2023", 7 pgs.
"U.S. Appl. No. 17/858,960, Final Office Action mailed Oct. 30, 2023", 17 pgs.
"U.S. Appl. No. 17/858,960, Non Final Office Action mailed May 22, 2023", 15 pgs.
"U.S. Appl. No. 17/858,960, Notice of Allowance mailed Jan. 23, 2024", 10 pgs.
"U.S. Appl. No. 17/858,960, Notice of Allowance mailed May 8, 2024", 10 pgs.
"U.S. Appl. No. 17/858,960, Preliminary Amendment Filed Sep. 27, 2022", 6 pgs.
"U.S. Appl. No. 17/858,960, Response filed Jan. 11, 2024 to Final Office Action mailed Oct. 30, 2023", 12 pgs.
"U.S. Appl. No. 17/858,960, Response filed Aug. 22, 2023 to Non Final Office Action mailed May 22, 2023", 10 pgs.
"Application Serial No. PCT/US2011/001163, Published International Application mailed Jan. 12, 2012", 1 pg.
"Application Serial No. PCT/US2014/026456, International Preliminary Report on Patentability mailed Sep. 24, 2015", 9 pgs.
"U.S. Appl. No. 13/173,400, Response filed Jun. 2, 2016 to Non Final Office Action mailed Dec. 3, 2015", 20 pgs.

"Austrailian Application Serial No. 2014251336, Examination Report mailed Nov. 1, 2016", 3 pgs.
"Australian Application Serial No. 2006282783, First Examiner Report mailed Sep. 23, 2011", 3 pgs.
"Australian Application Serial No. 2006282783, Response filed Apr. 12, 2012 to First Examiners Report mailed Sep. 23, 2011", 21 pgs.
"Australian Application Serial No. 2006282783, Response filed Apr. 18, 2013 to Subsequent Examiners Report mailed May 28, 2012", 5 pgs.
"Australian Application Serial No. 2006282783, Subsequent Examiners Report mailed May 28, 2012", 2 pgs.
"Australian Application Serial No. 2010236855, First Amendment filed Aug. 6, 2014 to First Examiner Report mailed Jan. 17, 2014", 10 pgs.
"Australian Application Serial No. 2010236855, First Examiner Report mailed Jan. 17, 2014", 4 pgs.
"Australian Application Serial No. 2013224686, First Examiner Report mailed Dec. 18, 2014", 2 pgs.
"Australian Application Serial No. 2013224686, Voluntary Amendment filed Jun. 13, 2014", 15 pgs.
"Australian Application Serial No. 2013274322, First Examiner Report mailed Jul. 8, 2016", 3 pgs.
"Australian Application Serial No. 2013274322, Response filed Feb. 8, 2017 to First Examiner Report mailed Jul. 8, 2016", 14 pgs.
"Australian Application Serial No. 2013274322, Response filed Feb. 8, 2017 to Office Action mailed Jul. 24, 2016", 11 pgs.
"Australian Application Serial No. 2014236952, First Examination Report mailed Jun. 5, 2019", 4 pgs.
"Australian Application Serial No. 2014236952, Response filed Sep. 17, 2019 to First Examination Report mailed Jun. 5, 2019", 41 pgs.
"Australian Application Serial No. 2014251336, Response filed Feb. 15, 2017 to Office Action mailed Nov. 1, 2016", 14 pgs.
"Australian Application Serial No. 2015224503, First Examiner Report mailed Dec. 5, 2016", 4 pgs.
"Australian Application Serial No. 2015224503, Response filed Oct. 9, 2017 to Subsequent Examiners Report mailed May 4, 2017", 24 pgs.
"Australian Application Serial No. 2015224503, Response filed Nov. 16, 2017 to Subsequent Examiners Report mailed Nov. 7, 2017", 17 pgs.
"Australian Application Serial No. 2015224503, Second Amendment filed Apr. 5, 2017 in response to First Examiner Report mailed Dec. 5, 2016", 14 pgs.
"Australian Application Serial No. 2015224503, Second Amendment filed Apr. 5, 2017 to First Examiner Report mailed Dec. 5, 2016", 14 pgs.
"Australian Application Serial No. 2015224503, Subsequent Examiners Report mailed May 4, 2017", 4 pgs.
"Australian Application Serial No. 2015224503, Subsequent Examiners Report mailed Nov. 7, 2017", 3 pgs.
"Australian Application Serial No. 2015224503, Subsequent Examiners Report mailed Nov. 22, 2017", 3 pgs.
"Australian Application Serial No. 2015224503, Subsequent Examiners Report mailed Dec. 5, 2017", 3 pgs.
"Australian Application Serial No. 2016235074, First Examination Report mailed Jul. 19, 2019", 3 pgs.
"Australian Application Serial No. 2017272168, First Examination Report mailed Mar. 5, 2019", 4 pgs.
"Australian Application Serial No. 2017272168, Reply filed Feb. 25, 2020 to Subsequent Examiners Report mailed Oct. 4, 2019", 3 pgs.
"Australian Application Serial No. 2017272168, Response filed Aug. 28, 2019 to First Examination Report mailed Mar. 5, 2019", 15 pgs.
"Australian Application Serial No. 2017272168, Subsequent Examiners Report mailed Oct. 4, 2019", 3 pgs.
"Austrailian Application Serial No. 2011295779, Examination Report mailed Jan. 30, 2015", 3 pgs.
"Australian Application Serial No. 2011295779, Response filed Aug. 3, 2015 to Examination Report mailed Jan. 30, 2015", 14 pgs.

(56) References Cited

OTHER PUBLICATIONS

"Brazil Application Serial No. 1120150236413, Office Action mailed Jul. 22, 2019", 4 pgs.
"Brazil Application Serial No. BR1120140312249, Office Action mailed Feb. 27, 2018".
"Brazil Application Serial No. BR1120140312249, Office Action mailed Aug. 14, 2019", W/ Machine English Translation, 7 pgs.
"Brazilian Application Serial No. 1120150236413, Office Action mailed Feb. 27, 2018".
"Brazilian Application Serial No. BR1120150236421, Office Action mailed Feb. 27, 2018", 2 pgs.
"Brazilian Application Serial No. BR1120150236421, Office Action mailed Feb. 28, 2023", W/ English Claims, 11 pgs.
"Brazilian Application Serial No. BR1120150236421, Office Action mailed Jul. 20, 2020", (w/ Concise Statement of Relevance), 5 pgs.
"Brazilian Application Serial No. BR1120150236421, Office Action mailed Sep. 16, 2022", 9 pgs.
"Brazilian Application Serial No. BR1120150236421, Response filed May 5, 2023 toOffice Action mailed Feb. 28, 2023", w/ English Claims, 14 pgs.
"Brazilian Application Serial No. BR1120150236421, Response filed Oct. 26, 2020 to Office Action mailed Jul. 20, 2020", (w/ English Translation of Claims), 12 pgs.
"Brazilian Application Serial No. BR1120150236421, Response filed Nov. 7, 2022 to Office Action mailed Sep. 16, 2022", w/ English Claims, 6 pgs.
"Canadian Application Serial No. 2,618,731, Office Action mailed Jan. 5, 2016", 4 pgs.
"Canadian Application Serial No. 2,618,731, Office Action mailed Mar. 27, 2013", 3 pgs.
"Canadian Application Serial No. 2,618,731, Office Action mailed Mar. 29, 2018", 3 pgs.
"Canadian Application Serial No. 2,618,731, Office Action mailed Apr. 7, 2017", 5 pgs.
"Canadian Application Serial No. 2,618,731, Office Action mailed Jun. 13, 2014", 2 pgs.
"Canadian Application Serial No. 2,618,731, Office Action mailed Jul. 17, 2020", 4 pgs.
"Canadian Application Serial No. 2,618,731, Response filed Jul. 4, 2016 to Office Action mailed Jan. 5, 2016", 4 pgs.
"Canadian Application Serial No. 2,618,731, Response filed Sep. 26, 2017 to Office Action mailed Apr. 7, 2017", 65 pgs.
"Canadian Application Serial No. 2,618,731, Response filed Sep. 27, 2013 to Office Action mailed Mar. 27, 2013", 20 pgs.
"Canadian Application Serial No. 2,618,731, Response filed Oct. 1, 2018 to Office Action mailed Mar. 29, 2018", 15 pgs.
"Canadian Application Serial No. 2,618,731, Response filed Nov. 17, 2020 to Office Action mailed Jul. 17, 2020", 47 pgs.
"Canadian Application Serial No. 2,618,731, Response filed Dec. 12, 2014 to Office Action mailed Jun. 13, 2014", 28 pgs.
"Canadian Application Serial No. 2,757,457, Office Action mailed Feb. 26, 2016", 6 pgs.
"Canadian Application Serial No. 2,757,457, Office Action mailed Dec. 29, 2016", 3 pgs.
"Canadian Application Serial No. 2,757,457, Response filed Jun. 28, 2017 to Office Action mailed Dec. 29, 2016", 9 pgs.
"Canadian Application Serial No. 2,757,457, Response filed Aug. 26, 2016 to Office Action mailed Feb. 26, 2016", (English Translation of Claims), 33 pgs.
"Canadian Application Serial No. 2,809,990, Examiner's Rule 30(2) Requisition mailed Oct. 18, 2019", 3 pgs.
"Canadian Application Serial No. 2,809,990, Office Action mailed Jun. 15, 2020", 3 pgs.
"Canadian Application Serial No. 2,809,990, Office Action mailed Jul. 23, 2018", 4 pgs.
"Canadian Application Serial No. 2,809,990, Office Action mailed Nov. 27, 2017", 4 pgs.
"Canadian Application Serial No. 2,809,990, Response filed Jan. 22, 2019 to Office Action mailed Jul. 23, 2018", 15 pgs.
"Canadian Application Serial No. 2,809,990, Response filed Apr. 16, 2020 to Examiner's Rule 30(2) Requisition mailed Oct. 18, 2019", 18 pgs.
"Canadian Application Serial No. 2,809,990, Response filed May 25, 2018 to Office Action mailed Nov. 27, 2017", 27 pgs.
"Canadian Application Serial No. 2,809,990, Response filed Oct. 14, 2020 to Office Action mailed Jun. 15, 2020", 4 pgs.
"Canadian Application Serial No. 2,876,648, Examiner's Rule 30(2) Requisition mailed Aug. 14, 2019", 4 pgs.
"Canadian Application Serial No. 2,876,648, Office Action mailed Jan. 3, 2019", 3 pgs.
"Canadian Application Serial No. 2,876,648, Office Action mailed Jun. 20, 2018", 4 pgs.
"Canadian Application Serial No. 2,876,648, Response filed Feb. 13, 2020 to Examiner's Rule 30(2) Requisition mailed Aug. 14, 2019", 15 pgs.
"Canadian Application Serial No. 2,876,648, Response filed Jun. 28, 2019 to Office Action mailed Jan. 3, 2019", 11 pgs.
"Canadian Application Serial No. 2,876,648, Response Filed Dec. 14, 2018 to Office Action mailed Jun. 20, 2018", 11 pgs.
"Canadian Application Serial No. 2,907,144, Office Action mailed Apr. 29, 2020", 5 pgs.
"Canadian Application Serial No. 2,907,144, Office Action mailed Jul. 7, 2021", 4 pgs.
"Canadian Application Serial No. 2,907,144, Office Action mailed Nov. 27, 2020", 4 pgs.
"Canadian Application Serial No. 2,907,144, Response filed Mar. 17, 2021 to Office Action mailed Nov. 27, 2020", 21 pgs.
"Canadian Application Serial No. 2,907,144, Response filed Aug. 21, 2020 to Office Action mailed Apr. 29, 2020", 18 pgs.
"Canadian Application Serial No. 2,907,144, Response filed Nov. 4, 2021 to Office Action mailed Jul. 7, 2021", 31 pgs.
"Canadian Application Serial No. 2,907,161, Examiners Rule 86(2) Report mailed Feb. 8, 2023", 5 pgs.
"Canadian Application Serial No. 2,907,161, Examiners Rule 86(2) Report mailed Aug. 15, 2024", 3 pgs.
"Canadian Application Serial No. 2,907,161, Office Action mailed Jan. 21, 2021", 3 pgs.
"Canadian Application Serial No. 2,907,161, Office Action mailed Feb. 4, 2020", 3 pgs.
"Canadian Application Serial No. 2,907,161, Response filed Jun. 4, 2020 to Office Action mailed Feb. 4, 2020", 15 pgs.
"Canadian Application Serial No. 2,907,161, Response filed Jun. 8, 2023 to Examiners Rule 86(2) Report mailed Feb. 8, 2023", 19 pgs.
"Chinese Application Serial No. 200680030925.4, First Office Action mailed Jan. 2, 2010", (English Translation), 4 pgs.
"Chinese Application Serial No. 200680030925.4, Office Action mailed Sep. 28, 2011", (w/ English Translation), 10 pgs.
"Chinese Application Serial No. 200680030925.4, Response filed Apr. 15, 2011 to Office Action mailed Jan. 31, 2011", (w/ English Translation of Amended Claims), 9 pgs.
"Chinese Application Serial No. 200680030925.4, Response Filed Oct. 19, 2010 to Office Action mailed Jun. 4, 2010", (w/ English Translation of Claims), 10 pgs.
"Chinese Application Serial No. 200680030925.4, Response filed Oct. 19, 2010 to Second Office Action mailed Jun. 4, 2010", (w/ English Translation of Amended Claims), 10 pgs.
"Chinese Application Serial No. 200680030925.4, Response filed Dec. 12, 2011 to Office Action mailed Sep. 28, 2011", (w/ English Translation of Amended Claims), 7 pgs.
"Chinese Application Serial No. 200680030925.4, Second Office Action mailed Jun. 4, 2010", (w/ English Translation), 8 pgs.
"Chinese Application Serial No. 200680030925.4, Third Office Action mailed Jan. 31, 2011", (w/ English Translation), 15 pgs.
"Chinese Application Serial No. 201080024899.0, Argument filed Oct. 14, 2013 in response to Office Action mailed Jan. 9, 2013", (w/ English Translation), 5 pgs.
"Chinese Application Serial No. 201080024899.0, Decision on Rejection mailed Oct. 30, 2013", 7 pgs.
"Chinese Application Serial No. 201080024899.0, Office Action mailed Jan. 9, 2013", (w/ English Translation), 16 pgs.
"Chinese Application Serial No. 201180052952.2, Office Action mailed Apr. 17, 2014", (w/ English Translation), 21 pgs.

(56) References Cited

OTHER PUBLICATIONS

"Chinese Application Serial No. 201180052952.2, Office Action mailed May 15, 2015", (w/ English Translation), 31 pgs.
"Chinese Application Serial No. 201180052952.2, Office Action mailed Oct. 19, 2015", (w/ English Translation), 12 pgs.
"Chinese Application Serial No. 201180052952.2, Office Action mailed Dec. 18, 2014", (w/ English Translation), 11 pgs.
"Chinese Application Serial No. 201180052952.2, Response filed Feb. 27, 2015 to Office Action mailed Dec. 18, 2014", (w/ English Translation of Claims), 13 pgs.
"Chinese Application Serial No. 201180052952.2, Response filed Jul. 30, 2015 to Office Action mailed May 15, 2015", (w/ English Translation of Amended Claims).
"Chinese Application Serial No. 201180052952.2, Response filed Sep. 2, 2014 to Office Action mailed Apr. 17, 2014", (w/ English Translation of Claims), 14 pgs.
"Chinese Application Serial No. 201180052952.2, Response filed Dec. 24, 2015 to Office Action mailed Oct. 19, 2015", (w/ English Translation of Amended Claims), 14 pgs.
"Chinese Application Serial No. 201210287455.7, Office Action mailed Nov. 14, 2013", (w/ English Translation), 11 pgs.
"Chinese Application Serial No. 201210287455.7, Response filed Mar. 31, 2014 to Office Action mailed Nov. 14, 2013", (w/ English Translation of Amended Claims), 9 pgs.
"Chinese Application Serial No. 201380041965.9, Office Action mailed Jan. 16, 2017", 6 pgs.
"Chinese Application Serial No. 201380041965.9, Office Action mailed Mar. 19, 2015", 2 pgs.
"Chinese Application Serial No. 201380041965.9, Office Action mailed Apr. 25, 2017", 3 pgs.
"Chinese Application Serial No. 201380041965.9, Office Action mailed May 30, 2016", 6 pgs.
"Chinese Application Serial No. 201380041965.9, Office Action mailed Oct. 26, 2017", 5 pgs.
"Chinese Application Serial No. 201380041965.9, Response filed Jan. 4, 2018 to Office Action mailed Oct. 26, 2017", no translation, 11 pgs.
"Chinese Application Serial No. 201380041965.9, Response filed Mar. 31, 2017 Office Action mailed Jan. 16, 2017", W/ English Claims, 13 pgs.
"Chinese Application Serial No. 201380041965.9, Response filed Sep. 8, 2017 to Office Action mailed Apr. 25, 2017", 12 pgs.
"Chinese Application Serial No. 201380041965.9, Response filed Dec. 8, 2016 to Office Action mailed May 30, 2016", 15 pgs.
"Chinese Application Serial No. 201480024592.9, Decision of Rejection mailed Jan. 13, 2021", (w/ English Summary), 8 pgs.
"Chinese Application Serial No. 201480024592.9, Office Action mailed Apr. 18, 2018", (w/ English Translation), 22 pgs.
"Chinese Application Serial No. 201480024592.9, Office Action mailed Aug. 3, 2020", (w English Translation), 19 pgs.
"Chinese Application Serial No. 201480024592.9, Office Action mailed Dec. 17, 2019", (w/ English Translation), 20 pgs.
"Chinese Application Serial No. 201480024592.9, Response filed Mar. 2, 2020 to Office Action mailed Dec. 17, 2019", (w/ English Translation of Claims), 18 pgs.
"Chinese Application Serial No. 201480024592.9, Response filed Apr. 27, 2021 to Decision of Rejection mailed Jan. 13, 2021", (w/ English Translation of Claims), 19 pgs.
"Chinese Application Serial No. 201480024592.9, Response filed Dec. 15, 2020 to Office Action mailed Aug. 3, 2020", (w/ English Translation of Claims), 13 pgs.
"Chinese Application Serial No. 201480024707.4, Office Action mailed Mar. 29, 2017", (w/ English Translation), 11 pgs.
"Chinese Application Serial No. 201480024707.4, Response filed Aug. 10, 2017 to Office Action mailed Mar. 29, 2017", W/ English Claims, 17 pgs.
"Chinese Application Serial No. 201680027075.6, Office Action mailed Apr. 18, 2019", w/ English translation, 5 pgs.
"Chinese Application Serial No. 201680027075.6, Office Action mailed Nov. 19, 2018", W/English Translation, 21 pgs.
"Chinese Application Serial No. 201680027075.6, Response Filed Apr. 4, 2019 to Office Action mailed Nov. 19, 2018", w/English Claims, 16 pgs.
"European Application Serial No. 20764535.9, Response filed Oct. 10, 2022 to Communication pursuant to Rules 161 and 162 filed Oct. 10, 2022", 18 pgs.
"European Application Serial No. 06790024.1, Office Action mailed Sep. 10, 2010", 7 pgs.
"European Application Serial No. 06790024.1, Office Action mailed Sep. 18, 2009", 1 pg.
"European Application Serial No. 06790024.1, Response filed Jan. 20, 2011 to Office Action mailed Sep. 10, 2010", 11 pgs.
"European Application Serial No. 06790024.1, Result of Consultation mailed Nov. 30, 2009", 3 pgs.
"European Application Serial No. 06790024.1, Supplementary European Search Report dated Jun. 5, 2009", 9 pgs.
"European Application Serial No. 06790024.1, Supplementary European Search Report mailed Jun. 5, 2009", 6 pgs.
"European Application Serial No. 10723848.7, Office Action mailed Jul. 8, 2014", 8 pgs.
"European Application Serial No. 10723848.7, Office Action mailed Dec. 2, 2011", 2 pgs.
"European Application Serial No. 10723848.7, Response filed Jun. 12, 2012 to Office Action mailed Dec. 2, 2011", 8 pgs.
"European Application Serial No. 11181797.9, Examination Notification Art. 94(3) mailed Feb. 3, 2014", 4 pgs.
"European Application Serial No. 11181797.9, Extended European Search Report mailed Jun. 11, 2012", 7 pgs.
"European Application Serial No. 11181797.9, Office Action mailed Feb. 3, 2014", 4 pgs.
"European Application Serial No. 11181797.9, Office Action mailed Feb. 21, 2013", 3 pgs.
"European Application Serial No. 11181797.9, Office Action mailed Jul. 16, 2012", 2 pgs.
"European Application Serial No. 11181797.9, Response filed Jan. 11, 2013 to Extended European Search Report mailed Jun. 11, 2012", 4 pgs.
"European Application Serial No. 11181797.9, Response filed Jun. 26, 2013 to Office Action mailed Feb. 21, 2013", 5 pgs.
"European Application Serial No. 11181797.9, Response filed Aug. 13, 2014 to Office Action mailed Feb. 3, 2014", 13 pgs.
"European Application Serial No. 11181797.9, Response filed Dec. 23, 2011 to Office Action mailed Oct. 28, 2011", 5 pgs.
"European Application Serial No. 11181797.9, Result of Consultation mailed Jun. 26, 2014", 3 pgs.
"European Application Serial No. 11776927.3, Examination Notification Art. 94(3) mailed Feb. 5, 2014", 6 pgs.
"European Application Serial No. 11776927.3, Office Action mailed Apr. 23, 2013", 2 pgs.
"European Application Serial No. 11776927.3, Response filed Jul. 2, 2015 to Telephone Interview on Jun. 23, 2015", 24 pgs.
"European Application Serial No. 11776927.3, Response filed Aug. 15, 2014 to Examination Notification Art. 94(3) mailed Feb. 5, 2014", 9 pgs.
"European Application Serial No. 11776927.3, Response filed Aug. 15, 2015 to Examination Notification Art. 94(3) mailed Feb. 5, 2014", 8 pgs.
"European Application Serial No. 11776927.3, Response filed Nov. 4, 2013 to Office Action mailed Apr. 23, 2013", 9 pgs.
"European Application Serial No. 11776927.3, Result of Consultation mailed Jun. 29, 2015", 3 pgs.
"European Application Serial No. 11803935.3, Examination Notification Art. 94(3) mailed Jul. 11, 2014", 5 pgs.
"European Application Serial No. 11803935.3, Examination Notification Art. 94(3) mailed Jul. 24, 2015", 5 pgs.
"European Application Serial No. 11803935.3, Extended European Search Report mailed Oct. 25, 2013", 8 pgs.
"European Application Serial No. 11803935.3, Response filed Jan. 20, 2015 to Office Action mailed Jul. 11, 2014", 10 pgs.
"European Application Serial No. 11803935.3, Response filed May 22, 2014 to Search Report mailed Nov. 12, 2013", 11 pgs.
"European Application Serial No. 11803935.3, Response filed Jun. 24, 2016 to Office Action mailed Jul. 24, 2015", 13 pgs.

(56) References Cited

OTHER PUBLICATIONS

"European Application Serial No. 12820042.5, Response filed Oct. 22, 2019 t to Communication pursuant to Rules 161(1) and 162 EPC mailed Apr. 11, 2019", 17 pgs.
"European Application Serial No. 13732752.4, Communication Pursuant to Article 94(3) EPC mailed Jan. 8, 2018", 4 pgs.
"European Application Serial No. 13732752.4, Communication Pursuant to Article 94(3) EPC mailed Jan. 17, 2017", 5 pgs.
"European Application Serial No. 13732752.4, Communication Pursuant to Article 94(3) EPC mailed May 6, 2016", 4 pgs.
"European Application Serial No. 13732752.4, Communication Pursuant to Article 94(3) EPC mailed Jun. 21, 2019", 4 pgs.
"European Application Serial No. 13732752.4, Communication Pursuant to Article 94(3) EPC mailed Oct. 31, 2018", 4 pgs.
"European Application Serial No. 13732752.4, Office Action mailed Feb. 12, 2015", 2 pgs.
"European Application Serial No. 13732752.4, Response filed Mar. 8, 2019 to Communication Pursuant to Article 94(3) EPC mailed Oct. 31, 2018", 12 pgs.
"European Application Serial No. 13732752.4, Response filed Jul. 18, 2018 to Communication Pursuant to Article 94(3) EPC mailed Jan. 8, 2018", 9 pgs.
"European Application Serial No. 13732752.4, Response filed Aug. 24, 2015 to Office Action mailed Feb. 12, 2015", 12 pgs.
"European Application Serial No. 13732752.4, Response filed Nov. 1, 2017 to Communication Pursuant to Article 94(3) EPC mailed Jan. 17, 2017", 15 pgs.
"European Application Serial No. 13732752.4, Response filed Nov. 16, 2016 to Communication Pursuant to Article 94(3) EPC mailed May 6, 2015", 11 pgs.
"European Application Serial No. 14721618.8, Communication Pursuant to Article 94(3) EPC mailed Jan. 2, 2017", 4 pgs.
"European Application Serial No. 14721618.8, Communication Pursuant to Article 94(3) EPC mailed Jan. 3, 2019", 3 pgs.
"European Application Serial No. 14721618.8, Communication Pursuant to Article 94(3) EPC mailed Oct. 31, 2017", 3 pgs.
"European Application Serial No. 14721618.8, Offfice Action mailed Nov. 20, 2015", 2 pgs.
"European Application Serial No. 14721618.8, Response filed May 13, 2019 to Communication Pursuant to Article 94(3) EPC mailed Jan. 3, 2019", 83 pgs.
"European Application Serial No. 14721618.8, Response filed May 26, 2016 to Office Action mailed Nov. 20, 2015", 8 pgs.
"European Application Serial No. 14721618.8, Response filed Jul. 11, 2017 to Communication Pursuant to Article 94(3) EPC mailed Jan. 2, 2017", 15 pgs.
"European Application Serial No. 14721618.8, Response filed Aug. 16, 2018 to Communication Pursuant to Article 94(3) EPC mailed Oct. 31, 2017", 82 pgs.
"European Application Serial No. 14725270.4, Office Action mailed Jun. 29, 2017", 4 pgs.
"European Application Serial No. 14725270.4, Office Action mailed Nov. 20, 2015", 2 pgs.
"European Application Serial No. 14725270.4, Response filed May 27, 2016 to Office Action mailed Nov. 20, 2015", 9 pgs.
"European Application Serial No. 14725270.4, Response filed Nov. 9, 2017 to Office Action mailed Jun. 29, 2017", 79 pgs.
"European Application Serial No. 15170077.0, Communication Pursuant to Article 94(3) EPC mailed Feb. 1, 2017", 2 pgs.
"European Application Serial No. 15170077.0, Communication Pursuant to Article 94(3) EPC mailed Oct. 24, 2017", 2 pgs.
"European Application Serial No. 15170077.0, Extended European Search Report mailed Dec. 7, 2015", 12 pgs.
"European Application Serial No. 15170077.0, Response filed Mar. 5, 2018 to Communication Pursuant to Article 94(3) EPC mailed Oct. 24, 2017", 22 pgs.
"European Application Serial No. 15170077.0, Response filed Jul. 13, 2016 to Extended European Search Report mailed Dec. 7, 2015", 8 pgs.
"European Application Serial No. 15170077.0, Response filed Aug. 11, 2017 to Communication Pursuant to Article 94(3) EPC mailed Feb. 1, 2017", 10 pgs.
"European Application Serial No. 15170077.0, Response filed Aug. 21, 2015 to Office Action mailed Jun. 12, 2015", 4 pgs.
"European Application Serial No. 16730926.9, Communication Pursuant to Article 94(3) EPC mailed Dec. 21, 2018", 5 pgs.
"European Application Serial No. 16730926.9, Invitation pursuant to Article 94(3) and Rule 71(1) EPC mailed Aug. 20, 2019", 16 pgs.
"European Application Serial No. 16730926.9, Response filed Apr. 17, 2019 to Communication Pursuant to Article 94(3) EPC mailed Dec. 21, 2018", 19 pgs.
"European Application Serial No. 17768594.8, Communication Pursuant to Article 94(3) EPC mailed Jan. 13, 2021", 7 pgs.
"European Application Serial No. 17768594.8, Response filed Jul. 23, 2021 to Communication Pursuant to Article 94(3) EPC mailed Jan. 13, 2021", 18 pgs.
"European Application Serial No. 20703611.2, Communication Pursuant to Article 94(3) EPC mailed Jul. 17, 2023", 7 pgs.
"European Application Serial No. 20703611.2, Response filed Jan. 17, 2024 to Communication Pursuant to Article 94(3) EPC mailed Jul. 17, 2023", 10 pgs.
"European Application Serial No. 20703611.2, Response Filed Feb. 28, 2022 to Communication Pursuant to Rules 161(1) and 162 EPC mailed Feb. 28, 2022", 9 pgs.
"European Application Serial No. 20764535.9, Communication Pursuant to Article 94(3) EPC mailed Sep. 30, 2024", 4 pgs.
"European Application Serial No. 20764535.9, Communication under Article 113 EPC mailed Jun. 19, 2023", 3 pgs.
"European Application Serial No. 20764535.9, Response filed Aug. 25, 2023 to Communication under Article 113 EPC mailed Jun. 19, 2023", 6 pgs.
"European Application Serial No. 21168393.3, Extended European Search Report mailed Sep. 13, 2021", 9 pgs.
"European Application Serial No. 21168393.3, Response Filed Apr. 20, 2022 to Extended European Search Report mailed Sep. 13, 2021", 11 pgs.
"Indian Application No. 11201/DELNP/2014, First Examination Report Received mailed Mar. 30, 2019", W/English Translation, 11 pgs.
"Indian Application Serial 2789/DELNP/2013, Hearing Notice mailed Dec. 12, 2022", 2 pgs.
"Indian Application Serial No. 9483/DELNP/2015, Response filed Jun. 11, 2020 to First Examiners Report mailed Dec. 18, 2019", 37 pgs.
"Indian Application Serial No. 1741/DELNP/2008, First Examiner Report mailed Jun. 24, 2013", 3 pgs.
"Indian Application Serial No. 1741/DELNP/2008, Response filed May 28, 2014 to Office Action mailed Jun. 24, 2013", 13 pgs.
"Indian Application Serial No. 2789/DELNP/2013, First Examination Report mailed Jan. 7, 2020", 7 pgs.
"Indian Application Serial No. 2789/DELNP/2013, Response filed Jul. 6, 2020 to First Examination Report mailed Jan. 7, 2020", 40 pgs.
"Indian Application Serial No. 2789/DELNP/2013, Revised Hearing Notice mailed Jan. 23, 2023", 2 pgs.
"Indian Application Serial No. 7719/DELNP/2011, Office Action mailed Nov. 1, 2017", 6 pgs.
"Indian Application Serial No. 9483/DELNP/2015, Hearing Notice mailed Nov. 1, 2023", 4 pgs.
"Indian Application Serial No. 9619/DELNP/2015, First Examination Report mailed Dec. 23, 2019", 6 pgs.
"Indian Application Serial No. 9619/DELNP/2015, Hearing Notice mailed Nov. 2, 2023", 3 pgs.
"Indian Application Serial No. 9619/DELNP/2015, Response filed Jun. 17, 2020 to First Examination Report mailed Dec. 23, 2019", 19 pgs.
"International Application No. PCT/US/2011/050266, International Search Report mailed Jan. 23, 2012", 6 pgs.
"International Application No. PCT/US/2011/050266, Written Opinion mailed Jan. 23, 2012", 8 pgs.

(56) References Cited

OTHER PUBLICATIONS

"International Application Serial No. PCT/US2006/033415, International Preliminary Report on Patentability dated Feb. 26, 2008", 5 pgs.
"International Application Serial No. PCT/US2006/033415, International Search Report mailed Dec. 21, 2006", 3 pgs.
"International Application Serial No. PCT/US2006/033415, Written Opinion mailed Dec. 21, 2006", 4 pgs.
"International Application Serial No. PCT/US2010/029463, International Preliminary Report on Patentability mailed Oct. 13, 2011", 8 pgs.
"International Application Serial No. PCT/US2010/029463, International Search Report mailed Dec. 20, 2010", 5 pgs.
"International Application Serial No. PCT/US2010/029463, Written Opinion mailed Dec. 20, 2010", 8 pgs.
"International Application Serial No. PCT/US2010/046644, International Preliminary Report on Patentability mailed Mar. 8, 2012", 8 pgs.
"International Application Serial No. PCT/US2010/046644, International Search Report mailed Jun. 22, 2011", 6 pgs.
"International Application Serial No. PCT/US2010/046644, Written Opinion mailed Jun. 22, 2011", 7 pgs.
"International Application Serial No. PCT/US2011/001163, International Preliminary Report on Patentability mailed Jan. 17, 2013", 7 pgs.
"International Application Serial No. PCT/US2011/01163, Search Report mailed Nov. 3, 2011", 3 pgs.
"International Application Serial No. PCT/US2011/01163, Written Opinion mailed Nov. 3, 2011", 5 pgs.
"International Application Serial No. PCT/US2011/050266, International Preliminary Report on Patentability mailed Mar. 5, 2013", 9 pgs.
"International Application Serial No. PCT/US2011/050266, International Search Report mailed Jan. 23, 2012", 6 pgs.
"International Application Serial No. PCT/US2011/050266, Written Opinion mailed Jan. 23, 2012", 8 pgs.
"International Application Serial No. PCT/US2013/045387, International Preliminary Report on Patentability mailed Dec. 24, 2014", 7 pgs.
"International Application Serial No. PCT/US2013/045387, International Search Report mailed Oct. 10, 2013", 4 pgs.
"International Application Serial No. PCT/US2013/045387, Written Opinion mailed Oct. 10, 2013", 5 pgs.
"International Application Serial No. PCT/US2014/026363, International Preliminary Report on Patentability mailed Sep. 24, 2015", 12 pgs.
"International Application Serial No. PCT/US2014/026363, International Search Report mailed Jul. 15, 2014", 4 pgs.
"International Application Serial No. PCT/US2014/026363, Written Opinion mailed Jul. 15, 2014", 6 pgs.
"International Application Serial No. PCT/US2014/026456, International Search Report mailed Aug. 1, 2014", 6 pgs.
"International Application Serial No. PCT/US2014/026456, Written Opinion mailed Aug. 1, 2014", 7 pgs.
"International Application Serial No. PCT/US2016/024032, International Preliminary Report on Patentability mailed Oct. 5, 2017", 10 pgs.
"International Application Serial No. PCT/US2016/024032, International Search Report mailed Aug. 26, 2016", 5 pgs.
"International Application Serial No. PCT/US2016/024032, Written Opinion mailed Aug. 26, 2016", 8 pgs.
"International Application Serial No. PCT/US2017/050278, International Preliminary Report on Patentability mailed Mar. 21, 2019", 10 pgs.
"International Application Serial No. PCT/US2017/050278, International Search Report mailed Dec. 12, 2017", 6 pgs.
"International Application Serial No. PCT/US2017/050278, Written Opinion mailed Dec. 12, 2017", 8 pgs.
"International Application Serial No. PCT/US2020/012587, International Preliminary Report on Patentability mailed Jul. 22, 2021", 9 pgs.
"International Application Serial No. PCT/US2020/012587, International Search Report mailed Apr. 17, 2020", 5 pgs.
"International Application Serial No. PCT/US2020/012587, Written Opinion mailed Apr. 17, 2020", 7 pgs.
"International Application Serial No. PCT/US2020/046963, International Preliminary Report on Patentability mailed Mar. 3, 2022", 7 pgs.
"International Application Serial No. PCT/US2020/046963, International Search Report mailed Nov. 26, 2020", 4 pgs.
"International Application Serial No. PCT/US2020/046963, Written Opinion mailed Nov. 26, 2020", 5 pgs.
"International Application Serial No. PCT/US2022/078272, International Preliminary Report on Patentability mailed May 2, 2024", 13 pgs.
"International Application Serial No. PCT/US2022/078272, International Search Report mailed Feb. 7, 2023", 8 pgs.
"International Application Serial No. PCT/US2022/078272, Written Opinion mailed Feb. 7, 2023", 11 pgs.
"International Application Serial No. PCT/US2022/078287, International Preliminary Report on Patentability mailed May 2, 2024", 9 pgs.
"International Application Serial No. PCT/US2022/078287, International Search Report mailed Jan. 31, 2023", 6 pgs.
"International Application Serial No. PCT/US2022/078287, Written Opinion mailed Jan. 31, 2023", 7 pgs.
"Israel Application Serial No. 215463, Notification Prior to Examination mailed Nov. 19, 2012", (English Translation), 3 pgs.
"Israel Application Serial No. 215463, Office Action mailed Oct. 20, 2014", (English Translation), 3 pgs.
"Israeli Application Serial No. 189418, Notification Prior to Refusal mailed Jan. 13, 2014", (w/ English Summary), 2 pgs.
"Israeli Application Serial No. 189418, Office Action dated Apr. 7, 2013", (English Translation), 2 pgs.
"Israeli Application Serial No. 189418, Office Action mailed May 17, 2010", (English Translation), 1 pg.
"Israeli Application Serial No. 189418, Office Action mailed Oct. 5, 2011", (w/ English Summary, 2 pgs.
"Israeli Application Serial No. 189418, Response filed Feb. 9, 2014 to Office Action dated Apr. 7, 2013", (English Translation), 36 pgs.
"Israeli Application Serial No. 189418, Response filed Mar. 19, 2012 to Office Action mailed Oct. 5, 2011", (English Translation), 9 pgs.
"Israeli Application Serial No. 189418, Response filed Sep. 14, 2010 to Office Action mailed May 17, 2010", (English Translation), 5 pgs.
"Israeli Application Serial No. 224964, Office Action mailed Nov. 23, 2016", (Translation), 2 pgs.
"Israeli Application Serial No. 224964, Office Action mailed Dec. 20, 2015", (English Translation), 2 pgs.
"Israeli Application Serial No. 224964, Response filed Jun. 19, 2016 to Office Action mailed Dec. 20, 2015", (Translation), 9 pgs.
"Israeli Application Serial No. 224964, Response filed Jun. 25, 2017".
"Israeli Application Serial No. 224964, Response filed Jun. 25, 2017 to Office Action mailed Nov. 23, 2016", (Translation), 4 pgs.
"Israeli Application Serial No. 233821, Office Action mailed Jul. 7, 2015", (English Translation), 2 pgs.
"Israeli Application Serial No. 233821, Response filed Apr. 10, 2016 to Office Action mailed Jul. 7, 2015", (English Translation of Claims), 3 pgs.
"Japanese Application Serial No. 2008-528231, Decision of Rejection mailed Feb. 4, 2013", (w/ English Translation), 4 pgs.
"Japanese Application Serial No. 2008-528231, Office Action mailed May 10, 2012", (w/ English Translation), 8 pgs.
"Japanese Application Serial No. 2008-528231, Response filed Nov. 12, 2012 to Office Action mailed May 10, 2012", (w/ English Translation of Amendment), 18 pgs.
"Japanese Application Serial No. 2012-243398, Amendment filed Jun. 25, 2013", (w/ English Translation, 11 pgs.

(56) References Cited

OTHER PUBLICATIONS

"Japanese Application Serial No. 2012-243398, Notice of Reasons for Rejection mailed Mar. 5, 2014", (w/ English Translation), 7 pgs.
"Japanese Application Serial No. 2012-248398, Amendment and Argument filed Aug. 18, 2014", (w/ English Translation), 50 pgs.
"Japanese Application Serial No. 2012-248398, Amendment filed Jun. 25, 2013", (w/ English Translation of Amendment), 10 pgs.
"Japanese Application Serial No. 2012-248398, Examiners Decision of Final Refusal mailed Jan. 7, 2015", (w/ English Translation), 6 pgs.
"Japanese Application Serial No. 2012-248398, Notice of Reasons for Rejection mailed Mar. 5, 2014", (w/ English Translation), 8 pgs.
"Japanese Application Serial No. 2012-503673, Argument and Amendment filed Nov. 28, 2014 in response to Office Action mailed Aug. 28, 2014", (w/ English Translation), 20 pgs.
"Japanese Application Serial No. 2012-503673, Decision of Rejection mailed Apr. 22, 2015", (w/ English Translation), 6 pgs.
"Japanese Application Serial No. 2012-503673, Office Action mailed Aug. 28, 2014", (w/ EnglishTranslation), 11 pgs.
"Japanese Application Serial No. 2013-527329, Office Action mailed Jul. 8, 2015", (w/ English Translation), 12 pgs.
"Japanese Application Serial No. 2013-527329, Response filed Oct. 7, 2015 to Office Action mailed Jul. 8, 2015", (w/ English Translation of Written Amendment), 12 pgs.
"Japanese Application Serial No. 2015-094591, Office Action mailed Apr. 13, 2016", (w/ English Translation), 10 pgs.
"Japanese Application Serial No. 2015-094591, Written Argument and Amendment filed Oct. 13, 2016 to Office Action mailed Apr. 13, 2016", (w/ English Translation Of Claims), 21 pgs.
"Japanese Application Serial No. 2015-164446, Examiners Decision of Final Refusal mailed Mar. 30, 2017", (w/ English Translation), 9 pgs.
"Japanese Application Serial No. 2015-164446, Office Action mailed Jul. 27, 2016", (w/ English Translation), 9 pgs.
"Japanese Application Serial No. 2015-164446, Office Action mailed Dec. 14, 2016", (w/ English Translation), 12 pgs.
"Japanese Application Serial No. 2015-164446, Response filed Nov. 21, 2016 to Office Action mailed Jul. 27, 2016", (w/ English Translation of Written Amendment and Argument), 19 pgs.
"Japanese Application Serial No. 2015-164446, Written Amended filed Mar. 13, 2017 in response to Office Action mailed Dec. 14, 2016", (Translation), 2 pgs.
"Japanese Application Serial No. 2015-517391, Office Action mailed Mar. 21, 2017", 8 pgs.
"Japanese Application Serial No. 2015-517391, Office Action mailed Aug. 28, 2018", W/English Translation, 8 pgs.
"Japanese Application Serial No. 2015-517391, Office Action mailed Nov. 7, 2017", W/English Translation, 7 pgs.
"Japanese Application Serial No. 2015-517391, Response filed Mar. 15, 2018 to Office Action mailed Nov. 7, 2017", w/claims, 15 pgs.
"Japanese Application Serial No. 2015-517391, Response filed Jun. 20, 2017 to Office Action mailed Mar. 21, 2017", 13 pgs.
"Japanese Application Serial No. 2015-94591, Amendment filed Jun. 5, 2015", (w/ English Translation), 5 pgs.
"Japanese Application Serial No. 2016-201559, Decision mailed Oct. 24, 2018", (w/ English Translation), 4 pgs.
"Japanese Application Serial No. 2016-201559, Office Action mailed Nov. 8, 2017", (w/ English Translation), 6 pgs.
"Japanese Application Serial No. 2016-201559, Response filed May 8, 2018 to Office Action mailed Nov. 8, 2017", (w/ English Translation of Amended Claims), 16 pgs.
"Japanese Application Serial No. 2016-502115, Examiners Decision of Final Refusal mailed Dec. 18, 2018", (w/ English Translation), 9 pgs.
"Japanese Application Serial No. 2016-502115, Office Action mailed Feb. 6, 2018", (w/ English Translation), 11 pgs.
"Japanese Application Serial No. 2016-502115, Response filed Aug. 6, 2018 to Office Action mailed Feb. 6, 2018", (w/ English Translation of Claims), 10 pgs.
"Japanese Application Serial No. 2016-502149, Office Action mailed Mar. 6, 2018", w/ English translation, 6 pgs.
"Japanese Application Serial No. 2016-502149, Response filed Sep. 6, 2018 to Office Action mailed Mar. 6, 2018", w/English claims, 42 pgs.
"Japanese Application Serial No. 2017-147965, Examiners Decision of Final Refusal mailed Jan. 23, 2019", (w/ English Translation), 8 pgs.
"Japanese Application Serial No. 2017-147965, Office Action mailed Jun. 13, 2018", (w/ English Translation), 7 pgs.
"Japanese Application Serial No. 2017-147965, Response Filed Dec. 18, 2018 to Office Action mailed Jun. 13, 2018", (English Translation of Claims), 2 pgs.
"Japanese Application Serial No. 2018-248452, Notification of Reasons for Rejection mailed Feb. 18, 2020", w/ English Translation, 7 pgs.
"Japanese Application Serial No. 2018-502040, Notification of Reasons for Refusal mailed Jan. 22, 2020", 6 pgs.
"Japanese Application Serial No. 2019-031120, Examiners Decision of Final Refusal mailed Jan. 18, 2021", (w/ English Translation), 6 pgs.
"Japanese Application Serial No. 2019-031120, Notification of Reasons for Rejection mailed Mar. 23, 2020", (w/ English Translation), 12 pgs.
"Japanese Application Serial No. 2019-031120, Written Opinion and Amendment filed Aug. 24, 2020 in response to Notification of Reasons for Rejection mailed Mar. 23, 2020", (w/ English Translation), 13 pgs.
"Japanese Application Serial No. 2019-031120, Written Request and Amendment filed May 14, 2021 in response to Examiners Decision of Final Refusal mailed Jan. 18, 2021", 7 pgs.
"Japanese Application Serial No. 2019-079360, Examiners Decision of Final Refusal mailed Oct. 29, 2019", w/ English Translation, 11 pgs.
"Japanese Application Serial No. 2019-079360, Notification of Reasons for Refusal mailed Jun. 25, 2019", (w/ English Translation), 8 pgs.
"Japanese Application Serial No. 2019-079360, Response filed Sep. 19, 2019 to Notification of Reasons for Refusal mailed Jun. 25, 2019", (w/ English Translation of Claims), 37 pgs.
"Japanese Application Serial No. 2019-095766, Examiners Decision of Final Refusal mailed Jan. 26, 2022", (w/ English Translation), 10 pgs.
"Japanese Application Serial No. 2019-095766, Notification of Reasons for Refusal mailed Apr. 15, 2021", (w/ English Translation), 10 pgs.
"Japanese Application Serial No. 2019-095766, Office Action mailed May 28, 2020", (w/ English Translation), 13 pgs.
"Japanese Application Serial No. 2019-095766, Response filed Sep. 13, 2021 to Notification of Reasons for Refusal mailed Apr. 15, 2021", (w/ English Translation), 21 pgs.
"Japanese Application Serial No. 2019-095766, Response filed Nov. 19, 2020 to Office Action mailed May 28, 2020", (English Translation), 2 pgs.
"Japanese Application Serial No. 2020-035278, Notification of Reasons for Rejection mailed May 19, 2020", (w/ English Translation), 5 pgs.
"Japanese Application Serial No. 2020-035278, Response filed Aug. 19, 2020 to Notification of Reasons for Rejection mailed May 19, 2020", (w/ English Translation of Claims), 9 pgs.
"Japanese Application Serial No. 2021-082285, Notification of Reasons for Rejection mailed Jul. 25, 2022", (w/ English Translation), 12 pgs.
"Japanese Application Serial No. 2021-082285, Response filed Jan. 25, 2023 to Notification of Reasons for Rejection mailed Jul. 25, 2022", w/ English Claims, 20 pgs.
"Japanese Application Serial No. 2021-082285, Voluntary Amendment filed Jun. 14, 2021", (w/ English Translation of Claims), 8 pgs.
"Japanese Application Serial No. 2021-539108, Examiners Decision of Final Refusal mailed Jul. 23, 2024", w/ English translation, 9 pgs.

(56) References Cited

OTHER PUBLICATIONS

"Japanese Application Serial No. 2021-539108, Notification of Reasons for Refusal mailed Oct. 23, 2023", W/ English Translation, 9 pgs.

"Japanese Application Serial No. 2021-539108, Response filed Apr. 23, 2024 to Notification of Reasons for Refusal mailed Oct. 23, 2023", w/ english claims, 10 pgs.

"Japanese Application Serial No. 2021-539108, Voluntary Amendment filed Jan. 4, 2023", w/ English claims, 8 pgs.

"Japanese Application Serial No. 2022-080860, Decision of Rejection mailed Feb. 27, 2024", w/ English Translation, 5 pgs.

"Japanese Application Serial No. 2022-080860, Notification of Reasons for Rejection mailed Jun. 5, 2023", w/english translation, 13 pgs.

"Japanese Application Serial No. 2022-080860, Response filed Dec. 4, 2023 to Notification of Reasons for Rejection mailed Jun. 5, 2023", W/English Translation, 12 pgs.

"Japanese Application Serial No. 2022-511024, Notification of Reasons for Refusal mailed Jun. 18, 2024", w/ English translation, 14 pgs.

"Japanese Application Serial No. 2022-511024, Voluntary Amendment Filed Sep. 6, 2023", w/ english claims, 8 pgs.

"Japanese Application Serial No. 2023-204715, Notification of Reasons for Refusal mailed May 23, 2024", w/ English Translation, 8 pgs.

"Japanese Application Serial No. 2023-204715, Response filed Aug. 21, 2024 to Notification of Reasons for Refusal mailed May 23, 2024", w/ english claims, 11 pgs.

"Korean Application Serial No. 10-2008-7007151, Notice of Preliminary Rejection mailed Nov. 24, 2012", (w/ English Translation), 9 pgs.

"Korean Application Serial No. 10-2008-7007151, Office Action mailed Jun. 27, 2013", (w/ English Translation), 4 pgs.

"Korean Application Serial No. 10-2008-7007151, Response filed Jan. 24, 2012 to Notice of Preliminary Rejection mailed Nov. 24, 2012", (w/ English Translation of Claims), 18 pgs.

"Korean Application Serial No. 10-2008-7007151, Response filed Oct. 28, 2013 to Office Action mailed Jun. 27, 2013", (w/ English Translation of Claims), 25 pgs.

"Korean Application Serial No. 10-2013-7008118, Notice of Preliminary Rejection mailed Nov. 20, 2017", (w/ English Translation), 6 pgs.

"Korean Application Serial No. 10-2013-7008118, Response filed Mar. 20, 2018 to Notice of Preliminary Rejection mailed Nov. 20, 2017", (w/ English Translation of Claims), 14 pgs.

"Korean Application Serial No. 10-2013-7028378, Notice of Preliminary Rejection mailed Jan. 24, 2014", (w/ English Translation), 8 pgs.

"Korean Application Serial No. 10-2013-7028378, Response filed Mar. 24, 2014 to Notice of Preliminary Rejection mailed Jan. 24, 2014", (w/ English Translation of the Claims), 28 pgs.

"Korean Application Serial No. 10-2014-7007674, Notice of Preliminary Rejection mailed Jun. 23, 2014", (w/ English Translation), 4 pgs.

"Korean Application Serial No. 10-2015-7000492, Notice of Preliminary Rejection mailed Jun. 13, 2019", 12 pgs.

"Korean Application Serial No. 10-2015-7029638, Notice of Preliminary Rejection mailed Aug. 28, 2020", (w/ English Translation), 14 pgs.

"Korean Application Serial No. 10-2015-7029638, Response filed Nov. 30, 2020 to Notice of Preliminary Rejection mailed Aug. 28, 2020", (w/ English Translation of Claims), 39 pgs.

"Korean Application Serial No. 10-2015-7029696, Notice of Preliminary Rejection mailed Aug. 28, 2020", w/ English translation, 14 pgs.

"Korean Application Serial No. 10-2015-7029696, Response filed Nov. 30, 2020 to Notice of Preliminary Rejection mailed Aug. 28, 2020", w/ English Claims, 20 pgs.

"Korean Application Serial No. 10-2021-7021860, Notice of Preliminary Rejection mailed Mar. 28, 2022", w/ English translation, 5 pgs.

"Korean Application Serial No. 10-2021-7021860, Notice of Preliminary Rejection mailed Sep. 28, 2021", (w/ English Translation), 6 pgs.

"Korean Application Serial No. 10-2021-7021860, Office Action mailed Nov. 25, 2022", w/ English Translation, 7 pgs.

"Korean Application Serial No. 10-2021-7021860, Response filed Apr. 27, 2023 to Office Action mailed Nov. 25, 2022", w/ English Claims, 18 pgs.

"Korean Application Serial No. 10-2021-7021860, Response filed Jun. 27, 2022 to Notice of Preliminary Rejection mailed Mar. 28, 2022", (w/ Translation of English claims), 16 pgs.

"Korean Application Serial No. 10-2021-7021860, Response filed Nov. 26, 2021 to Notice of Preliminary Rejection mailed Sep. 28, 2021", (w/ English Translation of Claims), 30 pgs.

"Korean Application Serial No. 10-2021-7023310, Notice of Preliminary Rejection mailed Sep. 24, 2021", w/ English translation, 5 pgs.

"Korean Application Serial No. 10-2023-7014385, Final Office Action mailed Jan. 30, 2024", w/ English Translation, 7 pgs.

"Korean Application Serial No. 10-2023-7014385, Notice of Preliminary Rejection mailed Aug. 9, 2023", w/ English Translation, 11 pgs.

"Korean Application Serial No. 10-2023-7014385, Response filed Jun. 19, 2024 to Final Office Action mailed Jan. 30, 2024", w/ English claims, 11 pgs.

"Korean Application Serial No. 10-2023-7014385, Response filed Sep. 7, 2023 to Notice of Preliminary Rejection mailed Aug. 9, 2023", w/ english claims, 13 pgs.

"Liver Regeneration", [online]. (c) 1998-2016 Mayo Foundation for Medical Education and Research, Retrieved from the Internet: < URL: http://www.mayo.edu/research/centers-programs/center-regenerative-medicine/focus-areas/liver-regeneration>, (2016), 2 pgs.

"Lone bone", [online]. Wikipedia, the free encyclopedia. {retrieved on Aug. 18, 2015]. Retrieved from the Internet: < URL: http://en.wikipedia.org/wiki/Long-bone>, 2 pgs.

"Mexican Application Serial No. [Pending], Office Action mailed Feb. 24, 2015".

"Mexican Application Serial No. MX/a/2008/002589, Office Action mailed Nov. 12, 2013", (w/ English Translation), 3 pgs.

"Mexican Application Serial No. MX/a/2008/002589, Response filed Jan. 22, 2014 to Office Action mailed Nov. 12, 2013", (w/ English Translation of Amendments), 12 pgs.

"Mexican Application Serial No. MX/A/2011/010197, Office Action mailed Apr. 17, 2013", (w/ English Summary), 7 pgs.

"Mexican Application Serial No. MX/A/2011/010197, Office Action mailed Aug. 31, 2012", (w/ English Summary), 3 pgs.

"Mexican Application Serial No. MX/A/2011/010197, Response filed Sep. 10, 2013 to Office Action mailed Apr. 17, 2013", (w/ English Translation of Claims), 7 pgs.

"Mexican Application Serial No. MX/A/2011/010197, Response filed Dec. 19, 2012 to Office Action mailed Aug. 31, 2012", (w/ English Translation of Amended Claims), 13 pgs.

"Mexican Application Serial No. MX/a/2013/002372, Substantive Examination Report mailed Mar. 17, 2016", (w/ English Summary), 3 pgs.

"Mexican Application Serial No. MX/a/2014/006778, Office Action mailed Jan. 30, 2017", (w/ English Translation), 4 pgs.

"Mexican Application Serial No. MX/a/2014/006778, Office Action mailed Sep. 14, 2016", (w/ English Summary), 3 pgs.

"Mexican Application Serial No. MX/a/2014/006778, Response filed Jun. 5, 2017 to Office Action mailed Jan. 30, 2017", (w/ English Translation of Claims), 14 pgs.

"Mexican Application Serial No. MX/a/2014/015270, Office Action mailed Dec. 16, 2017".

"Mexican Application Serial No. MX/a/2014/015270, Response filed May 15, 2018 to Office Action mailed Dec. 16, 2017", no/translation, 8 pgs.

"Mexican Application Serial No. MX/a/2015/013152, Office Action mailed May 15, 2019".

(56) References Cited

OTHER PUBLICATIONS

"Mexican Application Serial No. MX/a/2015/013152, Office Action mailed Aug. 25, 2020", 7 pgs.
"Mexican Application Serial No. MX/a/2015/013152, Office Action mailed Oct. 15, 2019", W/Machine English Translation, 10 pgs.
"Mexican Application Serial No. MX/a/2015/013152, Office Action mailed Nov. 14, 2018".
"Mexican Application Serial No. MX/a/2015/013154, Office Action mailed May 14, 2019", 3 pgs.
"Mexican Application Serial No. MX/a/2015/013154, Office Action mailed Oct. 10, 2019", W/ English Translation, 9 pgs.
"Mexican Application Serial No. MX/a/2015/013154, Office Action mailed Oct. 23, 2018", W/ English Translation, 7 pgs.
"Mexican Application Serial No. MX/a/2015/013154, Response filed Jul. 8, 2019 to Office Action mailed May 14, 2019", (w/ English Translation of Claims), 6 pgs.
"Mexican Application Serial No. MX/a/2015/013154, Response filed to Office Action mailed Oct. 23, 2018", w/ English Claims, 11 pgs.
"Mexican Application Serial No. MX/a/2017/011107, Office Action mailed Jun. 12, 2019", (w/ English Translation), 3 pgs.
"Mexican Application Serial No. MX/a/2017/011107, Response filed Aug. 26, 2019 to Office Action mailed Jun. 12, 2019", (w/ English Translation of Claims), 13 pgs.
"Mexican Application Serial No. MX/a/2021/010536, Office Action mailed Jul. 19, 2024", w/ Machine English Translation, 12 pgs.
"Russian Application Serial No. 2008111503, Office Action mailed Sep. 15, 2011", (English Translation), 4 pgs.
"Russian Application Serial No. 2008111503, Office Action mailed Oct. 27, 2011", W/ English Translation, 10 pgs.
"Russian Application Serial No. 2008111503, Official Action mailed Jul. 12, 2010", (w/ English Translation), 10 pgs.
"Russian Application Serial No. 2008111503, Response Filed Jan. 16, 2012 to Office Action mailed Sep. 15, 2011", (w/ English Translation of Amended Claims), 10 pgs.
"Russian Application Serial No. 2008111503, Response filed Jan. 16, 2012 to Office Action mailed Oct. 27, 2011", (w/ English Translation of Amended Claims), 10 pgs.
"Russian Application Serial No. 2008111503, Response filed Jul. 14, 2011 to Official Action dated Jul. 12, 2010", (w/ English Translation of Amended Claims), 18 pgs.
"Russian Application Serial No. 2008111503, Response filed Jul. 15, 2011 to Official Action dated Jul. 12, 2010", (w/ English Translation of Amended Claims), 18 pgs.
"Russian Application Serial No. 2011143730, Office Action mailed Apr. 1, 2014", (w/ English Translation), 9 pgs.
"Russian Application Serial No. 2011143730, Office Action mailed Sep. 19, 2014", (w/ English Translation), 7 pgs.
"Russian Application Serial No. 2011143730, Response filed Aug. 28, 2014 to Office Action mailed Apr. 1, 2014", (w/ English Translation of Claims), 6 pgs.
"Russian Application Serial No. 2012122055, Office Action mailed Mar. 9, 2017", (w/ English Translation), 7 pgs.
"Russian Application Serial No. 2012122055, Office Action mailed Jul. 11, 2016", (With English Translation), 13 pgs.
"Russian Application Serial No. 2012122055, Official Decision of Grant dated Jul. 13, 2017", (w/ English Translation), 14 pgs.
"Russian Application Serial No. 2012122055, Response filed Jan. 11, 2017 to Office Action mailed Jul. 11, 2016", (w/ English Summary), 4 pgs.
"Russian Application Serial No. 2012122055, Response filed Jun. 8, 2017", (w / English Translation of Claims), 14 pgs.
"Russian Application Serial No. 2013114382, Office Action mailed Feb. 16, 2016", (w/ English Translations), 10 pgs.
"Russian Application Serial No. 2013114382, Office Action mailed Nov. 21, 2015", (w/ English Translation), 7 pgs.
"Russian Application Serial No. 2013114382, Response filed Jan. 21, 2016 to Office Action mailed Nov. 21, 2015", (w/ English Translation of Amended Claims), 7 pgs.
"Russian Application Serial No. 2013114382, Response filed Aug. 16, 2016 to Office Action mailed Feb. 16, 2016", (w/ English Translation of Amended Claims), 8 pgs.
"Singapore Application Serial No. 11201507620V, Office Action mailed Feb. 13, 2017", 14 pgs.
"Singapore Application Serial No. 11201507620V, Office Action mailed Feb. 13, 2017".
"Singapore Application Serial No. 11201507620V, Office Action mailed May 6, 2019", 7 pgs.
"Singapore Application Serial No. 11201507620V, Office Action mailed May 9, 2016", Written Opinion, 7 pgs.
"Singapore Application Serial No. 11201507620V, Response filed Jun. 29, 2017 to Office Action mailed Feb. 15, 2017", 26 pgs.
"Singapore Application Serial No. 11201507673W, Written Opinion mailed Sep. 2, 2016", 6 pgs.
"Singapore Application Serial No. 11201507673W, Response filed Feb. 17, 2017 to Written Opinion issued on Sep. 23, 2016", 19 pgs.
"Singapore Application Serial No. 200801197-5, Examination Report mailed Aug. 6, 2010", 6 pgs.
"Singapore Application Serial No. 200801197-5, Examination Report mailed Sep. 16, 2010", 8 pgs.
"Singapore Application Serial No. 200801197-5, Invitation to Respond to Written Opinion mailed Apr. 2, 2009", 12 pgs.
"Singapore Application Serial No. 200801197-5, Response filed Sep. 2, 2009 to Written Opinion mailed Apr. 2, 2009", 4 pgs.
"Singaporean Application Serial No. SG 200801197-5, Examination Report mailed Sep. 16, 2010", 8 pgs.
"Stem Cell Definition", [online]. [retrieved on Sep. 21, 2015]. Printout from <www.google.com/search?q=%22stem+cell%22+definition&sourceid=ie7&rls=com.micorsoft.en.>, (2015), 1-2.
"Turkey Application Serial No. 117769273, Office Action mailed Jul. 29, 2019", 4 pgs.
Abbott, Allison, "Cell culture: Biology's new dimension", Nature, 424(6951), (2003), 3 pgs.
Alberts, B., et al., "Molecular Biology of the Cell (Third Edition), Garland Publishing", New York and London, (1994), 971-977.
Allen, Robert, et al., "Adrenal Extracellular Matrix Scaffolds Support Adrenocortical Cell Proliferation and Function In Vitro", Tissue Engineering, Part A, vol. 16, No. 11, 2010., (Aug. 5, 2010), 12 pgs.
Assad, Suheir, et al., "Insulin Production by Human Embryonic Stem Cells", Diabetes (2001), vol. 50, 1691-1697.
Atala, A., "Recent developments in tissue engineering and regenerative medicine", Curr. Opin. Pediatr., 18(2), (2006), 167-171.
Atala, A., et al., "Tissue-engineered autologous bladders for patients needing cystoplasty", Lancet, 367(9518), (2006), 1241-1246.
Bader, A., et al., "Tissue engineering of heart valves—human endothelial cell seeding of detergent acellularized porcine valves", Eur. J. Cardiothorac. Surg, 14(3), (1998), 279-284.
Badylak, S. F., et al., "Whole-organ tissue engineering: decellularization and recellularization of three-dimensional matrix scaffolds", Annu Rev Biomed Eng., 13, (Aug. 15, 2011), 27-53.
Badylak, S. F, "Xenogeneic extracellular matrix as a scaffold for tissue reconstruction", Transpl. Immunol., 12(3-4), (2004), 367-377.
Badylak, SF, "Xenogeneic extracellular matrix as a scaffold for tissue reconstruction", Trnaspl Immunol. Apr. 2004; 12(3-4):367-77, 2.
Badylak, Stephen F, et al., "Marrow-Derived Cells Populate Scaffolds Composed of Xenogeneic Extracellular Matrix", Experimental Hematology, 29(11), (Nov. 2001), 1310-1318.
Baertschiger, R. M., et al., "Xenotransplantation Literature Update Nov.-Dec. 2005", Xenotransplantation, 13(2), (2006), 96-99.
Banerjee, Ipsita, et al., "Impact of co-culture on pancreatic differentiation of embryonic stem cells", J. Tissue Eng. Regen. Med., 5(4), (2010), 313-323.
Banyasz, Tamas, et al., "Transformation of adult rat cardiac myocytes in primary culture", Experimental Physiology, 93(3), (2008), 13 pgs.
Baptista, P. M., et al., "A Novel Acellular Biologically Derived Scaffold for Tissue Engineering", Pittsburgh Tissue Engineering Initiative, [retrieved on Jul. 27, 2005] [Online]. Retrieved from the Internet: < URL: www.regenerate-online.com/abstract_Baptista.html>, (2005), 2 pgs.

(56) References Cited

OTHER PUBLICATIONS

Baptista, P. M, et al., "Human liver bioengineering using a whole liver decellularized bioscaffold", Methods Mol Biol., 1001, (Abstract Only), (2013), 1 pg.
Baptista, P. M., et al., "Human Liver Bioengineering Using a Whole Liver Decellularized Bioscaffold", In: Organ Regeneration Methods and Protocols, Methods in Molecular Biology 1001, edited by Basu, Joydeep, et al.,, (2013), 289-298.
Baptista, P. M, et al., "The use of whole organ decellularization for the generation of a vascularized liver organoid.", Hepatology, 53(2), (Feb., 2011), 604-617.
Baptista, Pedro, et al., "A Novel Whole Organ Bioscaffold for Tissue Engineering and Regenerative Medicine Applications", The FASEB Journal, 21 (Meeting Abstract Supplement), Database Biosis Abstract, (2007), A1233.
Baptista, Pedro M., et al., "Whole Organ Decellularization—A Tool for Bioscaffold Fabrication and Organ Bioengineering", Annu Int Conf IEEE Eng Med Biol Soc, 2009:6526-9, <https://pubmed.ncbi.nlm.nih.gov/19964173/>, (2009), 5 pgs.
Barakat, O., et al., "Use of Decellularized Porcine Liver for Engineering Humanized Liver Organ", Journal of Surgical Research, 173(11), (2012), e11-e25.
Batchelder, Cynthia A., et al., "Natural Scaffolds for Renal Differentiation of Human Human Embryonic Stem Cells for Kidney Tissue Engineering", PLOS One, 10(12): e0143849, (2015), 18 pgs.
Bauer, A., et al., "hDAF porcine cardiac xenograft maintains cardiac output after orthotopic gtransplantation into a baboon—a perioperative study", (Abstract), Xenotransplantation, 12(6), 444-449, (2005), 1 pg.
Ben-Yehudah, Ahmi, et al., "Evaluating protocols for embryonic stem cell differentiation into insulin-secreting beta-cells using insulin II-GFP as a specific and noninvasive reporter", Cloning Stem Cells, 11(2), (2009), 245-257.
Bijonowski, Brent, et al., "Bioreactor design for perfusion-based, highly vascularized organ regeneration", Current Opinion In Chemical Engineering, vol. 2, No. 1, (Feb. 1, 2013), 32-40.
Bishop, Elliot S., et al., "3-D bioprinting technologies in tissue engineering and regenerative medicine: Current and future trends", Genes & Diseases, 4, (2017), 185-195.
Bodnar, E., et al., "Damage of Porcine Aortic Valve Tissue Caused by the Surfactant Sodiumdodecylsulphate", Thorac,. Cardiovasc. Surg., 34(2), (1986), 82-85.
Bonandrini, Barbara, et al., "Recellularization of Well-Preserved Acellular Kidney Scaffold Using Embryonic Stem Cells", Tissue Engineering: Part A, vol. 20, Nos. 9 and 10, (2014), 1486-1498.
Bonvillain, R. W, et al., "A nonhuman primate model of lung regeneration: detergent-mediated decellularization and initial in vitro recellularization with mesenchymal stem cells.", Tissue Eng Part A., 18(23-24), (Abstract Only), (Dec., 2012), 1 pg.
Bonvillain, Ryan W, "A Nonhuman Primate Model of Lung Regeneration: Detergent-Mediated Decellularization and Initial In Vitro Recellularization with Mesenchymal Stem Cells", Tissue Engineering Part A , 18(23-24), (2012), 2437-2452.
Bordignon, "Stem-cell therapies for blood diseases", Nature 7097, (2006), 1100-1102.
Borschel, G. H., et al., "Contractile Skeletal Muscle Tissue-Engineered on an Acellular Scaffold", Plast .. Reconstr. Surg., 113(2), (2004), 595-602.
Boyd, Ashleigh, et al., "A Comparison of Protocols Used to Generate Insulin-Producing Cell Clusters from Mouse Embryonic Stem Cells", Stem Cells, 26(5), (2008), 1128-1137.
Brendel, Klaus, et al., "The acellular perfused kidney: a model for basement membrane permeability", Biology and Chemistry of Basement Membranes, Nicholas A Kefalides, author; New York : Academic Press, (1978), 177-193.
Brodie, T. G., "The perfusion of surviving organs", The Journal of Physiology, 29(3), (Jan. 1, 1903), 266-275.
Carter, V., et al., "Vimentin antibodies: a non-HLA antibody as a potential risk factor in renal transplantation", Transplant Proc., 37(2), (2005), 654-657.

Cartmell, J. S., et al., "Development of Cell-Seeded Patellar Tendon Allografts for Anterior Cruciate Ligament Reconstruction", Tissue Eng., 10(7-8), (2004), 1065-1075.
Cebotari, S., et al., "Construction of Autologous Human Heart Valves Based on an Acellular Allograft Matrix", Circulation, 106 (Suppl 1), (2002), 1-63--1-68.
Cechin, S., et al., "Influence of in vitro and in vivo oxygen modulation on p cell differentiation from human embryonic stem cells.", Stem Cells Transl. Med., 3(3), (2013), 277-289.
Chen, F., et al., "Acellular collagen matrix as a possible "off the shelf" biomaterial for urethral repair", Urology, 54(3), (1999), 407-410.
Chen, F., et al., "Experimental and clinical experience using tissue regeneration for urethral reconstruction", World J. Urol., 18(1), (2000), 67-70.
Chen, R.-Y., et al., "Process development of an acellular dermal matrix (ADM) for biomedical applications", Biomaterials, 25, (2004), 2679-2686.
Citro, et al., "", Biomaterials, 199, (Jan. 2019), 40-51.
Conconi, M. T., et al., "Homologous muscle acellular matrix seeded with autologous myoblasts as a tissue-engineering approach to abdominal wall-defect repair", Biomaterials, 26(15), (2005), 2567-2574.
Courtman, D. W., et al., "Development of a pericardial acellular matrix biomaterial: Biochemical and mechanical effects of cell extraction", J Biomed Materi Res., 28(6), (1994), 655-666.
Crapo, Peter M., et al., "An overview of tissue and whole organ decellularization process", Biomaterials, 32, (2011), 3233-3243.
Cukierman, E., et al., "Taking cell-matrix adhesions to the third dimension", Science, 294(5547), (2001), 5 pgs.
Czyz, Jaroslaw, et al., "Embryonic stem cell differentiation: The role of extracellular factors", Differentiation, 68, (2001), 167-174.
Dahl, S. L., et al., "Decellularized Native and Engineered Arterial Scaffolds for Transplantation", Cell Transplant., 12(6), (2003), 659-666.
Daly, A. B, et al., "Initial binding and recellularization of decellularized mouse lung scaffolds with bone marrow-derived mesenchymal stromal cells", Tissue Eng Part A., 18(1-2), (Abstract Only), (Jan. 2012), 1 pg.
D'Amour, et al., "Production of pancreatic hormone-expressing endocrine cells from human embryonic stem cells", Nat Bioteclmol 24(11), (2006), 11 pgs.
Davis, G. E., et al., "Endothelial Extracellular Matrix—Biosynthesis, Remodeling, and Functions During Vascular Morphogenesis and Neovessel Stabilization", Circ. Res,. 97, (2005), 1093-1107.
De Carlo, E, et al., "Pancreatic Acellular Matrix Supports Islet Survival and Function in a Synthetic Tubular Device: In Vitro and in Vivo Studies", International Journal of Molecular Medicine, vol. 25, No. 2,, (Feb. 2010), 195-202.
De Carlo, E., et al., "Pancreatic acellular matrix supports islet survival and function in a synthetic tubular device: In vitro and in vivo studies", International Journal of Molecular Medicine, 25, (2010), 195-202.
Decker, Gustav, et al., "Changes in Serum VEGF and SCF During Liver Regeneration in Humans", Digestive Disease Week Abstracts and Itinerary Planner Biosciences Information Service Philadelphia PA US, (May 17-22, 2003).
Dellgren, G., et al., "Eleven years' experience with the Biocor stentless aortic bioprsthesis: clinical and hemodynamic follow-up with long-term relative survival rate", Eur. J. Cardiothorac .. Surg., 22(6), (2002), 912-921.
Den Butter, G., et al., "Comparison of solutions for preservation of the rabbit liver as tested by isolated perfusion", Transpl .. Int., 8(6), (1995), 466-471.
Deng, M. C., et al., "Destination Mechanical circulatory Support: Proposal for Clinical Standards", J. Heart Lung Transplant., 22(4), (2003), 365-369.
Deyl, Z., et al., "Steric Hindrances in Protein Permeation Through the Basement Membrane Studied in Acellular Kidney", Physiologia Bohemoslovaca, 36(5), (1987), 425-434.
Doris, Taylor, "", Doctor's statement ( ?????).

(56) References Cited

OTHER PUBLICATIONS

Downing, Gregory J., et al., "Technical Assessment of the First 20 Years of Research Using Mouse Embryonic Stem Cell Lines", Stem Cells, 22, (2004), 1168-1180.
Duhaut, S., et al., "Approximately 150 Nucleotides from the 5' End of an Influenza a segment 1 Defective Virion RNA Are needed for Genome Stability during passage of Defective Virus in Infected Cells", Virology, 275(2) 278-285 Academic Press, Orlando, US, (Sep. 30, 2000), 8 pgs.
Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.
Edgar, Lauren, et al., "Utility of extracellular matrix powders in tissue engineering", Organogenesis, 14(4), (Sep. 5, 2018), 172-186.
Elkins, R. C., et al., "Decellularized Human Valve Allografts", Ann. Thorac. Surg., 71(Suppl 5), (2001), S428-S432.
Engbers-Buijtenhuijs, P., et al., "Biological characterisation of vascular grafts cultured in a bioreactor", Biomaterials, 27(11), (2006), 2390-2397.
Eshenhagen, T., et al., "Engineering Myocardial Tissue", Circ. Res., 97(12), (2005), 1220-1231.
Everwein, et al., Acta Biomaterialia, 117, (2020), 213-225.
Faulk, D. M, et al., "Role of the Extracellular Matrix in Whole Organ Engineering", J Cell Physiol., (Abstract Only), (Dec. 18, 2013), 1 pg.
Firth, J. D., et al., "Sodium handling in the isolated perfused kidney of the cirrhotic rat", Clin. Sci., 77(6), (1989), 657-661.
Frantz, Christian, et al., "The extracellular matrix at a glance", Cell Science at a Glance 123(24), (2010), 4195-4200.
Fridman, Robert, et al., "A Pilot Study to Evaluate the Effects of Perfusion-decellularized Porcine Hepatic-derived Wound Matrix on Difficult-to-heal Diabetic Foot Ulcers", Wounds 29(10), The official journal of AAWC, Wounds, A Compendium of Clinical Research and Practice,, (Oct. 2017).
Frohlich, M., et al., "Tissue engineered bone grafts: biological requirements, tissue culture and clinical relevance", Current Stem Cell Research & Therapy, vol. 3, (2008), 254-264.
Furuta, A., et al., "Pulsatile Cardiac Tissue Grafts Using a Novel Three-Dimensional Cell Sheet Manipulation Technique Functionally Integrates With the Host Heart, in Vivo", Circ. Res,. 98(5), (2006), 705-712.
Gerecht-Nir, S., et al., "Biophysical regulation during cardiac development and application to tissue engineering", Int. J. Dev. Biol., 50(2-3), (2006), 233-243.
Gibly, R. E., et al., "Advancing islet transplantation: from engraftment to the immune response", Diabetologia, 54, (2011), 2494-2505.
Gilbert, Thomas W., et al., "Decellularization of tissues and organs", Biomaterials, 27, (2006), 3675-3683.
Gilpin, Sarah E., et al., "Enhanced Lung Epithelial Specification of Human Induced Pluripotent Stem Cells on Decellularized Lung Matrix", Ann Thorac Surg,, 98, (2014), 721-729.
Goh, S. K., et al., "Perfusion-decellularized pancreas as a natural 3D scaffold for pancreatic tissue and whole organ engineering.", Biomaterials, 34(28), (2013), 6760-6772.
Grabow, N., et al., "Mechanical and Structural Properties of a Novel hybrid heart Valve Scaffold for Tissue Engineering", Artif. Organs, 28(11), (2004), 971-979.
Grayson, Warren L, et al., "Effects of Initial Seeding Density and Fluid Perfusion Rate on Formation of Tissue-Engineered Bone", Tissue Engineering: Part A, vol. 14, No. 11, (Nov. 1, 2008), 1809-1820.
Groetzner, J., et al., "Results of Pediatric Cardiac Transplantation—Long-Term Results of a 15-Year Experience", Thorac. Cardiov. Surg., 53 (Suppl 2), (2005), S149-S154.
Gualandris, A., et al., "The Latent Transforming Growth Factor-B-binding Protein-1 Promotes In Vitro Differentiation of Embryonic Stem Cells into Endothelium", Mol. Biol. Cell., 11(12), (2000), 4295-4308.

Guan, Yong, et al., "The effective bioengineering method of implantation decellularlzed renal extracellular matrix scaffolds", Oncotarget,6(34), (2015), 36126-36138.
Guruswamy, Rajesh Damodaran, et al., "Tissue and organ decellularization in regenerative medicine", Biotechnology Progress, American Chemical Society, Hoboken, USA, vol. 34, No. 6, (Oct. 8, 2018), 12 pgs.
Guvendiren, Murat, et al., "Designing Biomaterials for 3D Printing", ACS Biomaterials Science & Engineering, 2(10), (2016), 1679-1693.
Handa, et al., "The American Journal of Pathology", 184(2), (2014), 348-357.
Hashimoto, Yoshihide, et al., "The effect of deceilularized bone/bone marrow produced by high-hydrostatic pressurization on the osteogenic differentiation of mesenchymal stem cells", Biomaterials, vol. 32, No. 29, (Oct. 2011), 7060-7067.
Heinrich, Wrba, et al., "The Action of Serum from Partially Hepatectomized Rats on Explants of Liver and Tumors", Cancer Research, (Jan. 1963), 1116-1120.
Hirashima, M., et al., "Maturation of Embryonic Stem Cells Into Endothelial Cells in an in Vtro Model of Vasculogenesis.", Blood, 93(4), (1999), 1253-1263.
Hochedlinger, et al., "Nuclear reprogramming and pluripotency", Nature 7097, (2006), 1061-1067.
Hohlfeld, J., et al., "Tissue engineered fetal skin constructs for paediatric burns", Lancet, 366(9488), (2005), 840-842.
Hopper, R. A., et al., "Acellularization of Human Placenta With Preservation of the Basement Membrane: a potential matrix for tissue engineering", Ann. Plast. Surg., 51.6, (2003), 598-602.
Hou, S.-Y., et al., "Tissue-engineered peripheral nerve grafting by differentiated bone marrow stromal cells", Neuroscience, 140(1), (2006), 101-110.
Huang, et al., "Enhanced Functional Maturation of Fetal Porcine Hepatocytes in Three- Dimensional Poly-I-lactic Acid Scaffolds", A Culture Condition Suitable for Engineered Liver Tissues in Large-Scale Animal Studies,, Cell Transplantation, (2006), 799-809.
Huang, Ngan F., et al., "Regulation of the matrix microenvironments for stem cell engineering and regenerative medicine", Ann Biomed Eng, (Apr. 2011), 1201-1214.
Hudson, T. W., et al., "Engineering an Improved Acellular Nerve Graft via Optimized Chemical Processing", Tissue Eng., 10(9-10), (2004), 1346-1358.
Hussein, Kamal Hany, et al., "Heparin-gelatin mixture improves vascular reconstruction efficiency and hepatic function in bioengineered livers", Acta Biomaterialia, Elsevier, Amsterdam, NL, vol. 38, (Apr. 28, 2016), 82-93.
Hussein, Kamal H., "Three dimensional culture of HepG2 liver cells on a rat decellurized liver matrix for pharmacological studies", Journal of Biomedical Materials B: Applied Biomaterials, vol. 104B, Issue 2, (2015), 263-273.
Ikeda, E., et al., "Growing bioengineered teeth from single cells: potential for dental regenerative medicine", Expert Opin. Biol. Ther, 8(6), (2008), 735-744.
Isenberg, B. C., et al., "Small Diameter Artificial Arteries Engineered In Vitro", Circ. Res., 98(1), (2006), 25-35.
Jawad, H., et al., "Myocardial tissue engineering", British Medical Bulletin, 87, (2008), 31-47.
Jay, Steven M, et al., "Engineering of multifunctional gels integrating highly efficient growth factor delivery with endothelial cell transplantation", The FASEB journal, vol. 22, No. 8, (Apr. 16, 2008), 2949-2956.
John, Gentile, et al., "Effects of Post-Hepatectomized Rat Sera on Cultured Cells", Journal of Surgical Oncology, (Jan. 1969), 3-11.
Julie, Thompson, et al., "Extracorporeal Cellular Therapy (ELAD) in Severe Alcoholic Hepatitis: A Multinational, Prospective, Controlled, Randomized Trial behalf of the VTI-208 Study Group", Liver Transplantation, vol. 24, (Nov. 24, 2017), 380-393.
Juncosa-Melvin, N., et al., "The Effect of Autologous Mesenchymal Stem Cells on the Biomechanics and Histology of Gel-Collagen Sponge Constructs Used for Rabbit Patellar Tendon Repair", Tissue Eng., 12(2), (2006), 369-379.

(56) References Cited

OTHER PUBLICATIONS

Kang, Yu-Zhan, et al., "Decellularization technology application in which live reconstruct biological scaffold", National Medical Journal of China, vol. 89, No. 16, (2009), 1135-1138.

Kasimir, M.-T., et al., "The decellularized porcine heart valve matrix in tissue engineering. Platelet adhesion and activation", Thromb. Haemost., 94, (2005), 562-567.

Kazuo, Ohashi, et al., "Stability and Repeat Regeneration Potential of the Engineered Liver Tissues under the Kidney Capsule in Mice", Cell Transplantation vol. 14 no. 9, (Oct. 1, 2005), 621-627.

Keller, Gorder, "Embryonic stem cell differentiation: emergence of a new era in biology and medicine", Genes & Development, 19, (2005), 1129-1155.

Ketchedjian, A., et al., "Recellularization of Decellularized Allograft Scaffolds in Ovine Great Vessel Reconstructions", Ann. Thorac. Surg., 79(3), (2005), 888-896.

Kitahara, Hiroto, et al., "Heterotopic transplantation of a decellularized and recellularized whole porcine heart", Interactive Cardiovascular and Thoracic Surgery, (2016), 1-9.

Knight, R. L., et al., "Tissue Engineering of Cardiac Valves: Re-Seeding of Acellular Porcine Aortic Valve Matrices with human Mesenchymal Progenitor Cells", J. Heart Valve Dis., 14(6), (2005), 806-813.

Kofidis, T., et al., "Myocardial Restoration and Tissue Engineering of Heart Structures", Methods Mol. Med., 140, (2007), 273-290.

Kolker, A. R., et al., "Multilayer Reconstruction of abdominal Wall defects with Acellular Dermal Allograft (AlloDerm) and component Separation", Ann. Plast. Surg., 55(1), (2005), 36-41.

Kren, S, "Abstract 580: The Production of a Bio-Engineered Endothelial Intima From Cultured Cells Using Whole Cardiac Caraveric Extracellular Matrix", Circulation, 116, (2007), 5 pgs.

Kren, S, et al., "The Production of a Bio-Engineered Endothelial Intima From Cultured Cells Using Whole Cardiac Cadaveric Extracellular Matrix", Circulation, vol. 116, (2007), 105 pg.

Kren, S., et al., "The production of a bio-engineered endothelial intima from cultured cells using whole cardiac cadaveric extracellular matrix", Circulation, 116 Database Biosis, Biosciences Information Service, Philadelphia, PA, US; XP002612652, Database accession No. PREV200800197471 * abstract, (2007).

Kren, Stefan, et al., "The Production of a Bio-Engineered Endothelial Intima From Cultured Cells Using Whole Cardiac Cadaveric Extracellular Matrix", Circulation, 116 (Meeting Abstract Supplement), Database Biosis, Abstract 580, (2007), 4 pgs.

Kroon, Evert, et al., "Pancreatic endoderm derived from human embryonic stem cells generates glucose-responsive insulin-secreting cells in vivo", Nature Biotechnology, Advance Online Publication, (2008), 26 pgs.

Ladhoff, Juliane, et al., "Immune privilege of endotheial cells differentiated from endothelial progenitor cells", Cardiovascular Research, 88, (2010), 121-129.

Lamb, M., et al., "In Vitro Maturation of Viable Islets From Partially Digested Young Pig Pancreas", Cell Transplant., 23(3), (2014), 263-272.

Langer, R., et al., "Tissue Engineering", Science, 260, (1993), 920-926.

Lapidot, Tsvee, et al., "How do stem cells find their way home?", Blood, 106(6), (2005), 1901-1910.

Lee, Hyungseok, et al., "Development of Liver Decellularized Extracellular Matrix Bioink for Three-Dimensional Cell Printing-Based Liver Tissue Engineering", Biomacromolecules, 18(4), (Apr. 10, 2017), 1229-1237.

Lee, M. S., "Graft Jacket Augmentation of Chronic Achilles Tendon Ruptures", Orthopedics, 27(1 Suppl.), (2004), 151-153.

Levenberg, S., et al., "Engineering vascularized skeletal muscle tissue", Nat. Biotechnol., 23(7), (2005), 879-884.

L'heureux, N., et al., "Human tissue-engineered blood vessels for adult arterial revascularization", Nat. Med., 12(3), (2006), 361-365.

Lichtenberg, A., et al., "Flow-Dependent Re-Endothelialization of Tissue-Engineered Heart Valve", J. Heart Valve Dis., 15(2), (2006), 287-294.

Lin, P., et al., "Accesing Porcine Liver-Derived Biomatrix for Hepatic Tissue Engineering", Tissue Eng., 10(7-8), (2004), 1046-1053.

Lin, Paul, et al., "Assessing Porcine Liver-Derived Biomatrix for Hepatic Tissue Engineering", Tissue Engineering, vol. 10, No. 7/8, (2004), 1046-1053.

Lindvall, et al., "Stem cells for the treatment of neurological disorders", Nature 7097, (2006), 1094-1096.

Liu, Xiaoqing, et al., "Elastic fiber homeostasis requires lysyl oxidase-like 1 protein", Nature Genetics, 36(2), (2004), 178-182.

Lovett, Michael, et al., "Vascularization Strategies for Tissue Engineering", Tissue Engineering Part B: Reviews, vol. 15, No. 3, (Sep. 1, 2009), 353-370.

Lu, Tung-Ying, et al., "Repopulation of decellularized mouse heart with human induced pluripotent stem cell-derived cardiovascular progenitor cells", Nature Communications, 4, (2013), 1-11.

Mao, Shennen A., et al., "Sustained In Vivo Perfusion of a Re-Endothelialized Tissue Engineered Porcine Liver", International Journal of Transplantation Research and Medicine, vol. 3, No. 1, (Jan. 2017), 9 Pages.

Margariti, A., et al., "Direct reprogramming of fibroblasts into endothelial cells capable of angiogenesis and reendothelialization in tissue-engineered vessles", Proc. Natl. Acad. Sci. USA, 109(34), (2012), 13793-137938.

Matsuura, J. H., et al., "Cellular Remodeling of Depopulated Bovine Ureter Used as an Arteriovenous Graft in the Canine Model", J. Am. Coll. Surg., 198(5), (2004), 778-783.

Matthiesen, et al., "Large Solid Organ Perfusion Decellularization—A Start for Human—Sized Tissue Scaffolds", Circulation, 116, (2007), 5 pgs.

Matthiesen, T, et al., "Creating Biocompatible 3-D Scaffolds for Engineering Cardiovascular Tissues: Heart, Lung, and Kidney", Circulation, vol. 116, Suppl. S, (2007), 4 pgs.

Matthiesen, T. S., et al., "Abstract 572: Large Solid Organ Perfusion Decellularization—A Start for Human-Sized Tissue Scaffolds", Circulation, 116 Suppl. S, (2007), 5 pgs.

Matthiesen, Thomas, et al., "Creating Biocompatible 3-D Scaffolds for Engineering Cardiovascular Tissues: Heart, Lung, and Kidney", Circulation, 116 (Meeting Abstract Supplement), Database Biosis, Abstract 428, (Oct., 2007), 4 pgs.

Matthiesen, Thomas S, et al., "Large Solid Organ Perfusion Decellularization—A Start for Human-Sized Tissue Scaffolds?", Circulation, vol. 116, No. 16, Database Biosis, (2007), 103.

Mazzetti, S., et al., "Molecular anatomy of the cerebral microvessels in the isolated guinea-pig brain", Brain Res., 999(1), (2004), 81-90.

Mcfetridge, P. S., et al., "Preparation of porcine carotid arteries for vascular tissue engineering applications", J. Biomed. Mater Res. A, 70(2), (2004), 224-234.

Mirsadraee, S., et al., "Development and Characterization of an Acellular Human Pericardial matrix for Tissue Engineering", Tissue Eng., 12(4), (2006), 763-773.

Miyagawa, S., et al., "Tissue Cardiomyoplasty using bioengineered Contractile Cardiomyocyte Sheets to Repair Damaged Myocardium: Their Integration with Recipient Myocardium", Transplantation, 80(11), (2005), 1586-1595.

Morrison, et al., "Assymetric and symmetric stem-cell divisions in development and cancer", Nature 7097, (2006), 1068-1074.

Munoz-Elias, Guillermo, et al., "Marrow Stromal Cells, Mitosis, and Neuronal Differentiation: Stem Cell and Precursor Functions", Stem Cells, 21(4), (Jul. 2003), 437-448.

Muotri, et al., "Generation of neuronal variability and complexity", Nature 7097, (2006), 1087-1093.

Muscari, Claudio, et al., "Comparison between Culture Conditions Improving Growth and Differentiation of Blood and Bone Marrow Cells Committed to the Endothelial Cell Lineage", Biol. Proced. Online, 12, Article No. 89, (2010), 89-106.

Naito, H., et al., "Three-Dimensinal Cardiac Tissue Engineering Using a Thermorespoonsive Artificial Extracellular Matrix", ASAIO Journal, 50(4):, (2004), 344-348.

Navarro-Tableros, Victor, et al., "Recellularization of Rat Liver Scaffolds by Human Liver Stem Cells", Tissue Engineering: Part A, vol. 21, Nos. 11 and 12, (2015), 1929-1939.

(56) References Cited

OTHER PUBLICATIONS

Nikalson, L. E., et al., "Functional Arteries Grown in Vitro", Science, 284(5413), (1999), 489-493.
Oliver, R. F, et al., "Dermal collagen Implants", Biomaterials, 3(1), (1982), 38-40.
Oswald, Joachim, et al., "Mesenchymal Stem Cells can be Differentiated Into Endothelial Cells In Vitro", Stem Cells, 22(3), (2004), 377-384.
Ott, et al., "Combined transplantation of skeletal myoblasts and bone marrow stem cells for myocardial repair in rats", Eur. J. Cardiothorac. Surg 25, (2004), 627-634.
Ott, H C, et al., "Perfusion-decellularized matrix: using nature's platform to engineer a bioartificial heart", Nature Medicine, vol. 14, (2008), 213-221.
Ott, H. C, et al., "Cell-Based Cardiovascular Repair", Basic Res Cardiol, 100, (2005), 504- 517.
Ott, H. C, et al., "Perfusion-Decellularized Matrix: Using Nature's Platform To Engineer A Bioartificial Heart", Nat. Med., 14(2), (Abstract Only), (2008), 1 pg.
Ott, H. C, et al., "Perfusion-Decellularized Matrix: Using Nature's Platform to Engineer a Bioartificial Heart", Nat Med., 14(2), (Feb. 1, 2008), 213-221.
Ott, H. C., et al., "Regeneration and orthotopic transplantation of a bioartificial lung", Nature Medicine, 16(18), (Aug. 2010), 927-933.
Ott, H. C, et al., "Regeneration and orthotopic transplantation of a bioartificial lung", Nat Med., 16(8), (Abstract Only), (Aug., 2008), 1 pg.
Ott, H.C., et al., "Perfusion decellularized matrix, using nature's platform to engineer a bioartificial heart", Nature Medicine, vol. 14, No. 2. Feb. 2008., (Jan. 13, 2008), 9 pgs.
Park, H., et al., "A novel composite scaffold for cardiac tissue engineering", In Vitro Cell Dev. Biol. Anim., 41, (2005), 188-196.
Park, J.-K., et al., "Bioartificial Liver Systems: Current Status and Future Perspective", J Biosci Bioeng., 99(4), (2005), 311-319.
Pati, Falguni, et al., "Printing three-dimensional tissue analogues with decellularized extracellular matrix bioink", Nature Communications, 5:3935, (2014), 1-11.
Pelham, Jr., et al., "Cell locomotion and focal adhesions are regulated by substrate flexibility", Proc. Natl. Acad. Sci. USA 94, (1997), 13661-13665.
Perry, Robert, et al., "Clinical Scale Expansion of Human Pluripotent Stem Cells", (Abstract Only), Blood, 106(11), (2005), 1 pg.
Peters, J. M., et al., "Organ Weights and Water Levels of the Rat following Reduced Food Intake", The Journal of Nutrition, 90, (1966), 354-360.
Petersen, T. H, et al., "Tissue-engineered lungs for in vivo implantation", Science, 329(5991), (Abstract Only), (Jul. 30, 2010).
Petersen, T. H, et al., "Tissue-engineered lungs for in vivo implantation", Science Express, www.sciencexpress.org, (Jun. 24, 2010), 10 pgs.
Petro, Clayton C., et al., "An in vivo analysis of Miromesh—a novel porcine liver prosthetic created by perfusion decellularization", Journal of Surgical Resarch 201, (2016), 29-37.
Phillips, J. B., et al., "Neural Tissue Engineering: A Self-Organizing Collagen Guidance Conduit", Tissue Eng., 11, (2005), 1611-1617.
Philp, D., et al., "Complex extracellular matrices promote tissue-specific stem cell differentiation.", (Abstract Only), Stem Cells, 23(2), 288-296, (2005), 1.
Powers, M. J., et al., "Functional Behavior of Primary Rat Liver Cells in a Three—Dimensional Perfused Microarray Bioreactor", Tissue Eng., 8(3), (2002), 499-513.
Przybylski, et al., "Direct vascular connection between adrenal gland and kidney may play an important role in pathogenesis of hypertension", Med Hypotheses, (1991), 2 pgs.
Radisic, M., et al., "Mathematical model of oxygen distribution in engineered cardiac tissue with parallel channel array perfused with culture medium containing oxygen carriers.", Am J Physiol Heart Circ Physiol., 288(3), (Mar., 2005), H1278-89.
Rando, "Stem cells, ageing and the quest for immortality", Nature 7097, (2006), 1080-1086.

Rieder, E., et al., "Decellularization protocols of porcine heart valves differ importantly in efficiency of cell removal and susceptibility of the matrix to recellularization with human vascular cells.", J Thorac Cardiovasc Surg., 127(2), (Feb., 2004), 399-405.
Robertson, Matthew J., et al., "Optimizing Recellularization of Whole Decellularized Heart Extracellular Matrix", PLoS One, 9(2): e90406, (Feb. 2014), 1-10.
Robinson, K. A., et al., "Extracellular Matrix Scaffold for Cardiac Repair", Circulation 112[suppl I), (2005), 1-135--1-143.
Ross, Edward A, et al., "Embryonic Stem Cells Proliferate and Differentiate when Seeded into Kidney Scaffolds", Journal of The American Society of Nephrology, vol. 20, No. 11, (2009), 2338-2347.
Ross, Edward A., et al., "Mouse stem cells seeded into decellularized rat kidney scaffolds endothelialize and remodel basement membranes", Organogenesis, 8:2, (2012), 49-55.
Roy, S., et al., "Biomechanical properties of decellularized porcine common carotid arteries", Am. J. Physiol. Heart Circ. Physiol., 289(4), (2005), H1567-H1576.
Saito, A., "Development of bioartificial kidneys", Nephrology, 8(Issue s2), (Oct. 2003), S10-S15.
Saito, Hiroki, et al., "Generation of Glucose-Responsive Functional Islets with a Three-Dimensional Structure from Mouse Fetal Pancreatic Cells and iPS Cells In Vitro", PLoS One, 6(12): e28209, (Dec. 2011), 1-7.
Sankar, Krishana S., et al., "Culturing Pancreatic Islets in Microfluidic Flow Enhances Morphology of the Associated Endothelial Cells", PLoS One, 6: e24904, (2011), 1-11.
Sarraf, C. E., et al., "Cell proliferation rates in an artificial tissue-engineered environment", Cell Prolif., 38(4), (2005), 215-221.
Sawada, N., et al., "Effects of Extracellular Matrix Components on the Growth and Differentiation of Cultured Rat Hepatocytes", In Vitro Cellular & Developmental Biology , vol. 23, No. 4, (Apr. 1987), 267-73.
Sayk, F., et al., "Histopathologic Findings in a Novel Decellularized Pulmonary Homograft: An Autopsy Study", Ann. Thorac.. Surg., 79(5), (2005), 1755-1758.
Scadden, "The stem-cell niche as an entity of action", Nature 7097, (2006), 1075-1079.
Schaner, P. J, et al., "Decellularized vein as a potential scaffold for vascular tissue engineering", J Vasc Surg., 40(1), (Jul. 2004), 146-53.
Schenke-Lavland, K., et al., "Reprogrammed Mouse Fibroblasts Differentiate into Cells of the Cardiovascular and Hematopoietic Lineages", Stem Cells, 26(6), (2008), 1537-1546.
Schenke-Layland, K., et al., "Complete dynamic repopulation of decellularized heart valves by application of defined physical signals-an in vitro study.", Cardiovasc Res., 60(3), (Dec. 1, 2003), 497-509.
Schenke-Layland, K., et al., "Impact of decellularization of xenogeneic tissue on extracellular matrix integrity for tissue engineering of heart valves", J. Struct. Biol., 143, (2003), 201-208.
Schlager, Gunther, "Kidney Weight in Mice: Strain Differences and Genetic Determinatino", The Journal of Heredity, 59, (1968), 171-174.
Schmidt, C. E, et al., "Acellular vascular tissues: natural biomaterials for tissue repair and tissue engineering", Biomaterials, 21(22), (Nov. 2000), 2215-31.
Scudellari, Megan, "How iPS cells changed the world", Nature News &Comments, (Jun. 15, 2016), 8.
Seaberg, R. M., et al., "Stem and progenitor cells: the premature desertion of rigorous definitions", TRENDS in Neurosciences, 26(3), (Mar. 2003), 125-131.
Sekine, H., et al., "Cardiomyocyte Bridging Between Hearts and Bioengineered Myocardial Tissues with Mesenchymal Transition of Mesothelial Cells", J. Heart Lung Transplant., 25(3), (2006), 324-332.
Shaheen, Mohammed F, et al., "Sustained perfusion of revascularized bioengineered livers heterotopically transplanted into immunosuppressed pigs", Nature Biomedical Engineering, vol. 4, No. 4, (Oct. 2019), 437-445.

(56) References Cited

OTHER PUBLICATIONS

Sharma, N. S., et al., "Sodium Butyrate-Treated EmbryonicStem Cells Yield Hepatocyte—Like CellsExpressing a Glycolytic Phenotype", Biotechnology and Bioengineering, 94(6), (2006), 1053-1063.
Shen, Gan, et al., "Tissue engineering of blood vessels with endothelial cells differentiated from mouse embryonic stem cells", Cell Research, 13(5), (2003), 335-341.
Shimizu, Kazunori, et al., "Effective Cell-Seeding Technique Using Magnetite Nanoparticles and Magnetic Force onto Decellularized Blood Vessels for Vascular Tissue Engineering", Journal of Bioscience And Bioengineering, vol. 103, No. 5, (May 1, 2007), 472-478.
Shimizu, T., et al., "Fabrication of Pulsatile Cardiac Tissue Grafts Using A Novel 3—Dimensional Cell Sheet Manipulation Technique and Temperature-Responsive Cell Culture Surfaces", Circ Res., 90(3), (Feb. 22, 2002), e40-e48.
Shirakigawa, N., et al., "Decellularized liver as a practical scaffold with a vascular network template for liver tissue engineering", (Abstract Only), J Biosci Bioeng., 114(5), 546-551, (2012), 1 pg.
Shyy, J. Y.-J., et al., "Role of Integrins in Endothelial Mechanosensing of Shear Stress", Circ. Res., 91, (2002), 769-775.
Smardencas, A., et al., "Seeding of endothelial cells on the luminal surface of a sheet model of cold-stored (at 4) sheep carotid arteries.", Cell Transplant., 21(1), (2011), 285-297.
Smith, "A glossary for stem-cell biology", Nature 7097, (2006), 1059-1060.
Song, J. J., et al., "Enhanced In Vivo Function of Bioartificial Lungs in Rats", Ann. Thorac. Surg., 92(3), (2011), 998-1006.
Song, J. J, et al., "Regeneration and experimental orthotopic transplantation of a bioengineered kidney", Nat Med., 19(5), (May 2013), 646-651.
Song, Jeremy J, et al., "Organ engineering based on decellularized matrix scaffolds", Trends in Molecular Medicine, vol. 17, No. 8, (Aug. 2011), 424-432.
Song, Jeremy J,, et al., "Organ engineering based on decellularized matrix scaffolds", Trends in Molecular Medicine 17(8), (2011), 424-432.
Song, Jeremy J., et al., "Regeneration and experimental orthotopic transplantation of a bioengineered kidney", Nature Medicine Advance Online Publication, Received Sep. 4, 2012; accepted Feb. 11, 2013; published online Apr. 14, 2013, (2013), 1-8.
Song, Jeremy, et al., "Regeneration and experimental orthotopic transplantation of a bioengineered kidney", Nature Medicine Advance Online Publication, (Sep. 4, 2012), 1-8.
Soto-Gutierrez, A., et al., "A Whole-Organ Regenerative Medicine Approach for Liver Replacement", Tissue Engineering Part C: Methods, 17(6), (2011), 677-686.
Srivastave, et al., "Potential of stem-cell-based therapies for heart disease", Nature 7097, (2006), 1097-1099.
Stevenson, L. W., et al., "Left Ventricular Assist Device as Destination for Patients Undergoing Intravenous Inotropic Therapy. A Subset Analysis from REMATCH (Randomized Evaluation of Mechanical Assistance in Treatment of Chronic Heart Failure)", Circulation, 110(8), (2004), 975-981.
Stocum, D. L., "Regenerative biology and medicine", J. Musculoskelet Neuronal Interact., 2(3), (2002), 270-273.
Sudo, R., et al., "Reconstruction of 3d stacked-up structures by rat small hepatocytes on microporous membranes", FASEB J., 19, (2005), 1695-1697.
Sun, T., et al., "Development of a Closed Bioreactor System for Culture of Tissue—Engineered Skin at an Air-Liquid Interface", Tissue Eng., 11(11/12), (2005), 1824-1831.
Suresh, Vijayan, et al., "A retrospective study of the prognostic impact of cytokine secretion in mixed lymphocyte culture on long-term graft function following allogeneic renal transplantation", Transpl Int., 18(9), (2005), 1067-1071.
Swanson, Julia C., et al., "Characterization of Mitral Valve Anterior Leaflet Perfusion Patterns", NIH Public Access, published in final edited form as: J. Heart Valve Dis., 18(5), (2009), 488-495.

Tabata, Yasuhiko, et al., "Neovascularization effect of biodegradable gelatin microspberes incorporating basic fibroblast growth factor", Journal of Biomaterials Science. Polymer Edition, vol. 10, No. 1, (Jan. 1, 1999), 79-94.
Takagi, K., et al., "In Vivo Recellularization of Plain Decellularized Xenografts with Specific Cell Characterization in the Systemic Circulation: Histological and Immunohistochemical Study", Artif. Organs, 30(4), (2006), 233-241.
Takahashi, Kazutoshi, et al., "Induction of pluripotent stem cells from mouse embryonic and adult fibroblast cultures by defined factors", cell 126.4, (2006), 663-676.
Tan, P. H., et al., "Phenotypic and functional differences between human saphenous vein (HSVEC) and umbilical vein (HUVEC) endothelial cells", Atherosclerosis, 173(2), (2004), 171-183.
Tateishi, Keisuke, et al., "Generation of insulin-secreting islet-like clusters from human skin fibroblasts", J Biol Chem., 283(46), (Nov. 14, 2008), 31601-31607.
Taylor, D. A, et al., "Regenerating Functional Myocardium: Improved Performance after Skeletal Myoblast Transplantation", Nature Medicine, 4(8), (1998), 929-933.
Taylor, Doris A, et al., "From stem cells and cadaveric matrix to engineered organs", Current Opinion In Biotechnology, vol. 20, No. 5, (Oct. 1, 2009), 598-605.
Teebken, O. E., et al., "Tissue engineering of vascular grafts: human cell seeding of decellularised porcine matrix", Eur. J. Vasc. Endovasc. Surg., 19(4), (2000), 381-386.
Teebken, O. E, et al., "Tissue engineering:in vitro creation of tissue substitutes", Zentralbl Chir., 132(3), (2007), 236-246.
Terramani, Thomas T., et al., "Human macrovascular endothelial cells: optimization of culture conditions", In Vitro Cell Dev. Biol. Anim., 36(12), (2000), 125-132.
Thebaud, N. B., et al., "Human progenitor-derived endothelial cells vs. venous endothelial cells for vascular tissue engineering: an in vitro study.", J Tissue Eng Regen Med., 4(6), (2010), 473-484.
Toni, R., et al., "The Bioartifical Thyroid: a Biotechnical Perspective in Endocrine Organ Engineering for Transplantation Replacement", Acta Biomed., 78(Suppl 1), (2007), 129-155.
Touroo, Jeremy S., et al., "Bioengineering human blood vessel mimics for medical device testing using serum-free conditions and scaffold variations", Tissue Eng. Part C Methods, 19(4), (2013), 307-315.
Tower, T. T., et al., "Fiber alignment imaging during mechanical testing of soft tissues", Ann. Biomed. Eng., 30(10), (2002), 1221-1233.
Uchimura, E., et al., "Novel method of preparing acellular cardiovascular grafts by decellularization with poly(ethylene glycol)", J. Biomed. Mater. Res,. 67(3), (2003), 834-837.
Uygun, B. E, et al., "Decellularization and recellularization of whole livers", J Vis Exp., (48), (Abstract Only), (Feb. 2011), 1 pg.
Uygun, Basak E, et al., "Organ reengineering through development of a transplantable recellularized liver graft using decellularized liver matrix", Nature Medicine, vol. 16, No. 7, (2010), 814-820.
Uzarski, Joseph S., et al., "Epithelial Cell Repopulation and Preparation of Rodent Extracellular Matrix Scaffolds for Renal Tissue Development", Journal of Visualized Experiments, e53271, (2015), 9 pgs.
Van Putte, Bart P., et al., "Single-pass isolated lung perfusion versus recirculating isolated lung perfusion with melphalan in a rat model", Ann. Thorac. Surg., 74(3), (2002), 893-898.
Wagner, Darcy E, et al., "Design and Synthesis of an Artificial Pulmonary Pleura for High Throughput Studies in Acellular Human Lungs", Cellular and Molecular Bioengineering, vol. 7, No. 2, (2014), 184-195.
Wagner, S. M., et al., "The isolated normothermic hemoperfused porcine forelimb as a test system for transdermal absoption studies", J. Artif. Organs, 6(3), (2003), 183-191.
Wagner, S. M., et al., "The isolated normothermic hemoperfused porcine forelimb as a test system for transdermal absorption studies", J. Artif. Organs., 6(3), (2003), 183-191.
Walles, T., et al., "Acellular Scaffold Implantation—No. Alternative to Tissue Engineering", Int. J. Artif. Organs, 26(3), (2003), 225-234.

(56) References Cited

OTHER PUBLICATIONS

Wang, P.-C., et al., "Reconstruction of Renal Glomerular Tissue Using Collagen Vitrigel Scaffold", J. Biosci.. Bioeng., 99(6), (2005), 529-540.

Wang, X, et al., "Preparation and characterization of a collagen/chitosan/heparin matrix for an implantable bioartificial liver", J Biomater Sci Polym Ed., 16(9), (2005), 1063-1080.

Wang, Xiaojun, et al., "Decellularized liver scaffolds effectively support the proliferation and differentiation of mouse fetal hepatic progenitors", J. Biomed Mater Res Part A, 102A, (2014), 2027-2025.

Wang, Yunfang, et al., "Lineage Restriction of Human Hepatic Stem Cells to Mature Fates Is Made Efficient by Tissue-Specific Biomatrix Scaffolds", Hepatology, 53, (2011), 293-305.

Weind, Kirsten L., et al., "The Aortic Valve Blood Supply", J. Heart Valve Dis., 9(1), (Jan. 2000), 1-8.

Woods, T., et al., "Effectiveness of three extraction techniques in the development of a decellularized bone-anterior cruciate ligament-bone graft", Biomaterials, 26(35), (Dec. 1, 2005), 7339-7349.

Xing, Qianzhe, et al., "Hepatectomised patient sera promote hepatocyte differentiation of human-induced pluripotent stem cells", Digestive and Liver Disease W.B Saunders GB, (May 29, 2014), 731-732.

Xu, et al., Journal of Biornaterials applications. 30(4), (2015), 379-387.

Yagi, H., et al., "Human-Scale Whole-Organ Bioengineering for Liver Transplantation: A Regenerative Medicine Approach", Cell. Transplant., 22(2), (2013), 231-242.

Yang, Lijun, et al., "In vitro trans-differentiation of adult hepatic stem cells into pancreatic endocrine hormone-producing cells", Proc. Natl. Acad. Sci. USA, 99(12), (2002), 8078-8083.

Yasui, Haruyo, et al., "Excitation propagation in three-dimensional engineered hearts using decellularized matrix", Biomaterials, 35, (2014), 7839-7850.

Yoshio, Nei Gai, "Theories on freeze-drying", Vacuum Industry, 1957, vol. 4, No. 5 p. 131-136., (May 5, 1957), 9 pgs.

Zandonella, C., "Tissue Engineering: The Beat Goes On", Nature, 421(6926), (2003), 884-886.

Zeltinger, J., et al., "Development and characterization of Tissue-Engineered Aortic Valves", Tissue Engineering, 7(11), (2001), 9-22.

Zhang, Jianhua, et al., "Functional cardiomyocytes derived from human induced pluripotent stem cells", Circ. Res., 104(4), (2009), e30-e41.

Zhou, et al., "", Cell Tiss. Res., 365, (2016), 157-171.

Zhou, Bo-Jiang, et al., "Effects of hepatectomized rat serum on the transdifferentiation of adult rat bone marrow cells into hepatocyte-like cell", Chinese Journal of Hepatology vol. 12, No. 12 US National Library of Medicine NLM Bethesda Md US, (Dec. 2004), 730-733.

Zhou, Pengcheng, et al., "Decellularization and Recellularization of Rat Livers With Hepatocytes and Endothelial Progenitor Cells", Artificial Organs, (2015), 1-14.

Zimmermann, W. H, et al., "Engineered heart tissue for regeneration of diseased hearts", Biomaterials, 25(9), (Apr. 2004), 1639-47.

Zimmermann, W. H., et al., "Engineered heart tissue grafts improve systolic and diastolic function in infarcted rat hearts", Nat. Med., 12(4), (2006), 452-458.

\* cited by examiner

Figure 1. Irradiated decellularized tissue inside of a shaping mold.
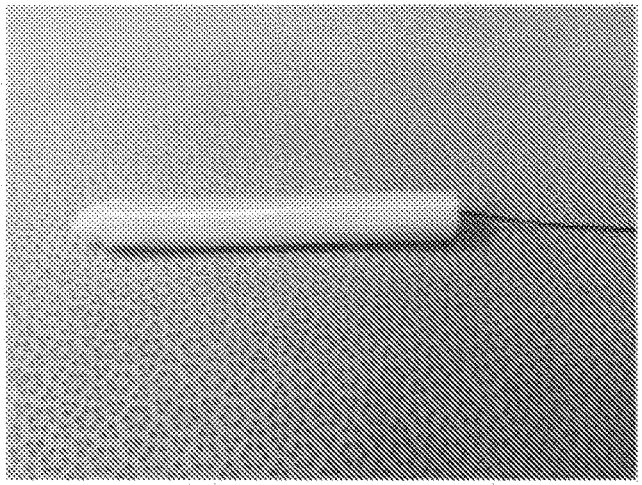
Figure 2. Removing irradiated decellularized tissue from a shaping mold.
Figure 3. Decellularized tissue retaining the shape of the mold it was irradiated in.
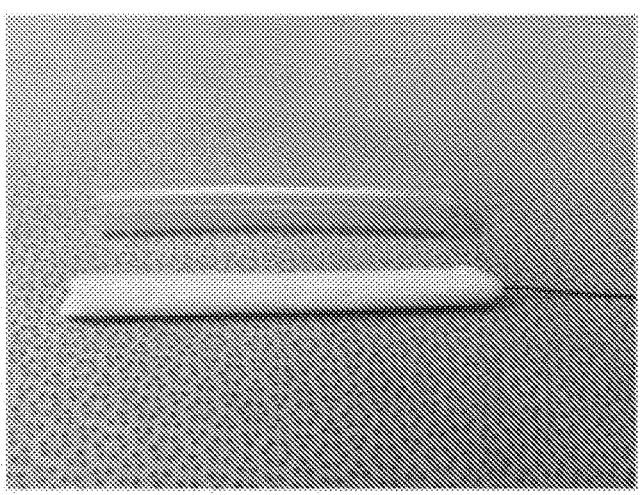

FISTULA FILLER AND DEPLOYMENT SYSTEM

CROSS REFERENCE

This application is a U.S. National Stage Filing under 35 U.S.C. 371 from International Application No. PCT/US2019/036942, filed Jun. 13, 2019, which claims the benefit of U.S. Provisional Application No. 62/684,426, filed Jun. 13, 2018, which are incorporated by reference herein in their entirety.

BACKGROUND

A fistula is an abnormal anastomosis, that is, an abnormal connection between a set of organs or vessels, e.g., where there are two hollow spaces (technically, two epithelialized surfaces), such as blood vessels, intestines, or other hollow organs. The connection may take on the form of a tract which is often difficult to heal or close. Fistulas can be caused by injury or surgery, but they can also result from an infection or inflammation. Fistulas are generally a disease condition, but they may be surgically created for therapeutic reasons.

Surgery is often required to assure adequate drainage of the fistula (so that pus may escape without forming an abscess). Various surgical procedures can be commonly used, most commonly fistulotomy, placement of a seton (a cord that is passed through the path of the fistula to keep it open for draining), or an endorectal flap procedure (where healthy tissue can be pulled over the internal side of the fistula to keep feces or other material from reinfecting the channel). Current treatment often involves filling the fistula with fibrin glue or plugging it with plugs made of porcine small intestine submucosa. Surgery for fistulae, e.g., anorectal fistulae, is not without side effects, including recurrence, reinfection and incontinence.

SUMMARY

The retention of the shape of decellularized tissue or of a portion of an organ can be accomplished through the irradiation of the decellularized tissue or the portion of the organ inside a shaping mold. The enclosure of decellularized tissue or a portion of an organ inside of a mold or other constraining material, such as stainless steel or platinum or polymers such as polytetrafluoroethylene (PTFE) or polycaprolactone (PCL), allows the tissue to take on the shape of the mold or constraint and subsequently retain that shape after it is irradiated. This can result in decellularized extracellular matrix having defined (pre-determined) shapes, e.g., for therapeutic uses. For example, the defined shape may be introduced to a deployment system such as one for surgical placement of a fistula filler, e.g., a product that takes on the shape of the fistula, or a plug, e.g., a product that displaces the area of the fistula in order to fit inside the fistula and can be in one embodiment more rigid than a fistula filler. The system can include a hollow device which contains the filler or plug. The system may be inserted into the fistula tract and the filler or plug may be deployed by pulling, pushing or otherwise expelling the filler or plug into the tract. The deployment device can then be removed from the tract leaving behind the filler or plug within the fistula tract.

Thus, disclosed herein are methods to maintain or inhibit an alteration in volume or shape of hydrated decellularized extracellular matrix from a mammalian organ or tissue or a portion thereof. A "hydrated decellularized extracellular matrix" can be a decellularized extracellular matrix that is not fully dry, e.g., it is at least partially hydrated with an aqueous solution such as deionized water, or saline, e.g., phosphate buffered saline. The method can include at least partially reducing malleability of an isolated at least partially hydrated at least partially decellularized organ or portion thereof in a mold. In some embodiments, a method can comprise at least partially reducing malleability. In some cases, a method can comprise exposing an at least partially hydrated at least partially decellularized organ or portion thereof to a select dose of radiation. In some embodiments a method can include providing a hydrated decellularized extracellular matrix from a mammalian organ or tissue or a portion thereof; placing or introducing the hydrated decellularized extracellular matrix from the mammalian organ or tissue or the portion thereof into a mold having a predefined shape which optionally can be in packaging, e.g., a pouch, tray, vial, or sterile container; and subjecting the hydrated decellularized extracellular matrix from the mammalian organ or tissue or the portion thereof in the mold to a selected dose of radiation to provide for maintenance or inhibition of an alteration in the volume or shape of the hydrated decellularized extracellular matrix that is in the mold. In another embodiment, a hydrated decellularized extracellular matrix from a mammalian organ or tissue or a portion thereof can be placed or introduced into a mold having a predefined shape which optionally can be in packaging, e.g., a pouch, tray, vial, or sterile container; subjecting the hydrated decellularized extracellular matrix from the mammalian organ or tissue or the portion thereof in the mold to dehydration; and subjecting the dehydrated decellularized extracellular matrix in the mold to a selected dose of radiation, e.g., to provide for maintenance or inhibition of an alteration in the volume or shape of the decellularized extracellular matrix that is in the mold. In one embodiment, the decellularized extracellular matrix from the mammalian organ or tissue or a portion thereof can be hydrated in saline, e.g., 0.9% normal saline or phosphate buffered saline, water or autologous serum, plasma, e.g., platelet rich plasma. In one embodiment, the decellularized extracellular matrix from the mammalian organ or tissue or a portion thereof can be placed into a preselected mold. In one embodiment, the hydrated decellularized extracellular matrix from the mammalian organ or tissue or portion thereof can be pressed into the mold. In one embodiment, multiple layers of hydrated decellularized extracellular matrix from the mammalian organ or tissue or a portion thereof can be placed or pressed into the mold. In one embodiment, the mammal can be a pig or human. In one embodiment, the organ can be a liver, muscle, lung, spleen or heart. In one embodiment, the dose of radiation can be about 5 kGy to 50 kGy. In one embodiment, the dose of radiation can be about 5 kGy to 15 kGy. In one embodiment, the dose of radiation can be about 15 kGy to 25 kGy. In one embodiment, the dose of radiation can be about 25 kGy to 50 kGy. In one embodiment, the radiation can be E-beam radiation or gamma radiation. In one embodiment, the radiation can be thermal or UV radiation. In one embodiment, after irradiation, the decellularized extracellular matrix can be dried. In one embodiment, the hydrated portion can be about 0.25 cm×0.25 cm, e.g., 1 cm×1 cm, to about 60 cm×60 cm (length×width). In one embodiment, the hydrated portion can be about 0.5 cm×0.5 cm×0.5 cm to about 30 cm×30 cm×30 cm. In one embodiment, the hydrated portion thereof can be about 1 cm×1 cm (length× width) to about 10 cm×10 cm. In one embodiment, the hydrated portion can be about 1 cm×2 cm to about 10 cm×12 cm. In one embodiment, the hydrated portion can be about 1 cm×6 cm to about 3 cm×20 cm. In one embodiment, the hydrated portion for anal uses can be about 0.5 cm×4 cm to about 3×10 cm, for vaginal uses can be about 0.5 cm×4 cm to about 3 cm×10 cm, for biliary uses can be about 0.2 cm×2 cm to about 3 cm×1 cm, for gastroenterological use can be about 0.2 cm×2 cm to about 3×10 cm, for bladder uses can be about 0.5 cm×4 cm to about 3 cm×10 cm, for esophageal uses can be about 0.2 cm×2 cm to 3 cm×10 cm, for nerve wraps can be about 0.2 cm (diameter)×1 cm length to about 2 cm×10 cm, or for tendon wraps can be about 1 cm×2 cm to about 4 cm×12 cm. In one embodiment, the portion can be obtained from a decellularized mammalian organ or tissue. In one embodiment, the portion can be obtained from the mammalian organ or tissue before decellularization. In one embodiment, the hydrated decellularized extracellular matrix from the mammalian organ or tissue or the portion thereof prior to radiation, can be inflated with a gas or vapor. In one embodiment, the hydrated portion, prior to and after radiation, has the shape of a cube, rectangular prism or an irregular strip. In one embodiment, the cube can be about 1 cm×1 cm to about 10 cm×10 cm. In one embodiment, the rectangular prism can be about 1 cm×2 cm to about 10 cm to about 12 cm. In one embodiment, an irregular strip about 1 cm×6 cm to about 3 cm to about 20 cm. In one embodiment, the molded and irradiated portion can be about 1 cm×1 cm to about 60 cm×60 cm. In one embodiment, the molded and irradiated portion can be about 0.5 cm×0.5 cm×0.5 cm to about 30 cm×30 cm×30 cm. In one embodiment, the molded and irradiated portion thereof can be about 1 cm×1 cm to about 10 cm×10 cm. In one embodiment, the molded and irradiated portion can be about 1 cm×2 cm to about 10 cm×12 cm. In one embodiment, the molded and irradiated portion can be about 1 cm×6 cm to about 3 cm×20 cm. In one embodiment, the molded and irradiated decellularized extracellular matrix can be subjected to dehydration.

Also disclosed herein is an isolated irradiated portion of a decellularized extracellular matrix from a mammalian organ or tissue having a defined shape useful for therapy. In one embodiment, the shape of the isolated irradiated portion of a decellularized extracellular matrix can be useful as a nerve or tendon wrap. In one embodiment, the shape can be useful for, for example, anal, vaginal, biliary, gastrointestinal, bladder or esophageal fistula repair. For example, a filler for vaginal repair may be about 0.5 cm×about 4 cm to about 3 cm×about 10 cm; for biliary repair may be about 0.2 cm×about 2 cm to 3 cm× about 10 cm; for gastrointestinal repair may about 0.2 cm×about 2 cm to about 3×about 10 cm; for bladder repair may be about 0.5 cm×about 4 cm to about 3 cm×about 10 cm; or for esophageal repair may be about 0.2 cm×about 2 cm to about 3×about 10 cm. In one embodiment, a nerve wrap may have a diameter of about 0.2 cm and a length of about 1 cm or a diameter of about 2 cm and a length of about 10 cm, and a tendon wrap may have a diameter of about 1 cm and a length of about 2 cm or a diameter of about 4 cm and a length of about 12 cm.

Also disclosed herein are methods of preparing a surgical filler deployment device. The method can include providing a deployment device for a surgical filler; providing the isolated irradiated portion described herein; and introducing the isolated irradiated portion into a hollow portion of the device. In one embodiment, the deployment device can be formed of plastic, metal, a composite, a biologic material, or combination thereof. In one embodiment, the deployment device can be a cylindrical tube, a triangular tube, a square tube, or a rectangular tube. In one embodiment, the deployment device can be at least partially biodegradable. In one embodiment, the deployment device can further comprise a pusher or a plunger.

Uses for the deployment device can include a method of treating a mammal in need of a surgical filler, e.g., where the mammal may be in need of anal, vaginal, biliary, gastrointestinal, bladder or esophageal fistula repair, or abnormal connections caused by trauma wounds. Uses for the isolated irradiated portion of a decellularized extracellular matrix from a mammalian organ or tissue, e.g., without a deployment device, can include use as a nerve or tendon wrap.

Also disclosed herein are kits that can comprise an at least partially hydrated at least partially decellularized extracellular matrix and a mold. In some embodiments a kit can comprise an isolated molded, at least partially irradiated portion of the at least partially decellularized extracellular matrix and a surgical filler deployment device. In some embodiments a kit can comprise an isolated molded, at least partially irradiated portion of an at least partially decellularized extracellular matrix in a sealed container. In some embodiments a kit can be in a cleanroom. In some embodiments a kit can be in a factory.

Also disclosed herein is a system that can comprise an isolated molded, at least partially irradiated portion of an at least partially decellularized extracellular matrix, an input attached to an at least partially irradiated at least partially hydrated at least partially decellularized extracellular matrix, an output attached to an at least partially irradiated at least partially hydrated at least partially decellularized extracellular matrix, growth media, and at least one of: a temperature control apparatus, an atmosphere controlling apparatus, or a humidity controlling apparatus. In some embodiments an at least partially hydrated at least partially decellularized extracellular matrix can be cannulated, and an input and an output can be attached to an at least partially irradiated at least partially hydrated at least partially decellularized extracellular matrix by a cannula. In some embodiments a system can be in a cleanroom. In some embodiments a system can be in a factory.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of exemplary embodiments are set forth with particularity in the appended claims. A better understanding of the features and advantages will be obtained by reference to the following detailed description that sets forth illustrative embodiments, in which the principles of exemplary embodiments are utilized, and the accompanying drawings of which:

FIG. 1 depicts an image of irradiated decellularized tissue inside of an exemplary shaping mold.

FIG. 2 depicts an image of removal of irradiated decellularized tissue from a shaping mold.

FIG. 3 depicts an image of molded decellularized tissue (it retains the shape of the mold it was irradiated in).

DETAILED DESCRIPTION

Decellularized tissue from organs or tissues such as liver, lung, muscle, spleen or heart can be cut or pressed into various shapes. However, the decellularized tissue may be limited in the retention of that shape due to the nature of collagen fibers and the empty cellular compartments in the extracellular matrix. To create a decellularized tissue or portion thereof, or a portion of a decellularized organ, that retains a desired shape as described herein, the tissue or portion can be placed into a shaped mold or other constraining device and irradiated. Following irradiation, the decellularized tissue or portion, once removed from the shaping mold or constraining device, retains the shape of the mold or device that the tissue or portion was irradiated in. Thus, this disclosure provides for irradiating decellularized portions of organ or tissues placed into a shaping mold or constraining device to impart a desired shape on the decellularized portion of an organ or tissue. The shape retaining decellularized portion of an organ or tissue can be put to use in a number of applications including but not limited to the use of portions of whole organ or tissue portions thereof as surgical fillers, surgical mesh, wraps, surgical protectors, drug delivery units, surgical connectors or fillers for fistulas and other voids. Alternatively, the shape retaining decellularized portion of an organ or tissue may be seeded with any type of cells following sterilization.

In one embodiment, the irradiation of decellularized tissue or a portion of an organ inside a selected mold increases the tissue or portion memory/recoil. In some embodiments, a dose of radiation can be from about 1 kGy to about 100 kGy, from about 5 kGy to about 100 kGy, from about 10 kGy to about 100 kGy, from about 15 kGy to about 100 kGy, from about 20 kGy to about 100 kGy, from about 25 kGy to about 100 kGy, from about 30 kGy to about 100 kGy, from about 35 kGy to about 100 kGy, from about 40 kGy to about 100 kGy, from about 45 kGy to about 100 kGy, from about 50 kGy to about 100 kGy, from about 55 kGy to about 100 kGy, from about 60 kGy to about 100 kGy, from about 65 kGy to about 100 kGy, from about 70 kGy to about 100 kGy, from about 75 kGy to about 100 kGy, from about 80 kGy to about 100 kGy, from about 85 kGy to about 100 kGy, from about 90 kGy to about 100 kGy, or from about 95 kGy to about 100 kGy.

In one embodiment, the increased shape retention of the decellularized tissue or portion of an organ by irradiating the decellularized tissue or portion of an organ, allows for ease of cutting (e.g., trimming), thereby providing for desired three dimensional portions of the matrix. In one embodiment, the molded, irradiated decellularized tissue or portion of an organ can be for use in treatment of fistulas. In one embodiment, the molded, irradiated decellularized tissue or portion of an organ can be for use as a shape retaining surgical filler. In one embodiment, the molded, irradiated decellularized tissue or portion of an organ can be for use as a shape retaining surgical wrap, connector or protector. In one embodiment, the molded, irradiated decellularized tissue or portion of an organ can be for use as a shape retaining surgical wrap. In one embodiment, prior to molding, the decellularized tissue or portion of an organ can be inflated with a gas or vapor, e.g., while inside a mold for a shape retaining surgical filler or for a shape retaining wound matrix.

Disclosed herein are systems which can be composed of a hollow deployment device containing a fistula filler or plug that may be inserted into the fistula tract. The deployment device allows for placement of a soft fistula filler or plug into a fistula tract. The deployment device also allows for easier placement of a long filler or plug into a fistula tract. Placement of a fistula filler or plug can be aided by the hollow device which allows the filler or plug to be placed within the tract prior to removal of the hollow device. The deployment device may be formed of a polymer including but not limited to polytetrafluororethylene, polypropylene, polyethylene, polystyrene, nylon, polyetheretherketone, or polyurethane. In one embodiment, the hollow deployment device may be composed of plastic, metal, composite, biologic material, or combination thereof. In one embodiment, the hollow deployment device may be a cylindrical tube, triangular tube, square tube, rectangular tube or some combination thereof. In one embodiment, the hollow deployment device may have non-rigid walls to facilitate placement of the molded, irradiated decellularized tissue or portion of an organ in a non-linear tract. In one embodiment, the hollow deployment device may have non-rigid walls to facilitate expelling of the molded, irradiated decellularized tissue or portion of an organ into the tract. In one embodiment, the hollow deployment device may have an opening in the wall such as a slit or hole to facilitate initial placement of the molded, irradiated decellularized tissue or portion of an organ into the hollow device during manufacturing. In one embodiment, the molded, irradiated decellularized tissue or portion of an organ may be further combined with a biodegradable polymer. In one embodiment, the system may be supplied with a pusher or plunger to push the molded, irradiated decellularized tissue or portion of an organ into the tract. In one embodiment, the system may be supplied with medical-grade string or suture to pull the molded, irradiated decellularized tissue or portion of an organ into or out of the tract. In one embodiment, the system may be used to deploy the molded, irradiated decellularized tissue or portion of an organ into anal fistulas, vaginal fistulas, biliary fistulas, gastrointestinal fistulas, bladder fistulas and esophageal fistulas.

Exemplary Sources of Organs and Tissues for Decellularized Extracellular Matrix (ECM)

A tissue is a group of cells with a common structure and function, e.g., epithelial tissue, connective tissue, muscle tissue (skeletal, cardiac, or smooth muscle), and nervous tissue, and includes a pliable sheet that covers or lines or connects organs. An organ is a collection of tissues (two or more) joined in structural unit to serve a common function. Organs include but are not limited to the brain, liver, pancreas, bone, spleen, heart, stomach, kidney, lungs, whole muscles, thymus, anus, and intestine. As used herein, an organ can include perfusable whole organs, or parts of an organ, or vascularized structures thereof, and a tissue includes any structures that contain vascularized tissues, e.g., a trachea.

The ECM of an organ or tissue, or a vascularized portion thereof, may be obtained from any source including, without limitation, heart, liver, lungs, skeletal muscles, brain, pancreas, spleen, kidneys, uterus, eye, spinal cord, intestine, omentum, whole muscle, or bladder, or any portion thereof (e.g., an aortic valve, a mitral valve, a pulmonary valve, a tricuspid valve, a pulmonary vein, a pulmonary artery, coronary vasculature, septum, a right atrium, a left atrium, a right ventricle, or a left ventricle). A solid organ refers to an organ that has a "substantially closed" vasculature system. A "substantially closed" vasculature system with respect to an organ means that, upon perfusion with a liquid, the majority of the liquid can be contained within the solid organ or pass out the native vascular structures and does not leak out of the solid organ, assuming the major vessels are cannulated, ligated, or otherwise restricted. Despite having a "substantially closed" vasculature system, many of the organs listed above have defined "entrance" and "exit" vessels which can be useful for introducing and moving the liquid throughout the organ during perfusion. In addition, other types of vascularized organs or tissues such as, for example, all or portions of joints (e.g., knees, shoulders, or hips), anus, trachea, or spinal cord, can be perfusion decellularized. Further, avascular tissues such as, for example, cartilage or cornea, may be decellularized when part of a larger vascularized structures such as a whole leg.

Decellularization of Organs or Tissues

Decellularization generally includes the following steps: stabilization of the solid organ, e.g., a vascularized structure thereof, or tissue, decellularization of the solid organ or tissue, renaturation and/or neutralization of the solid organ or tissue, washing the solid organ, degradation of any DNA remaining on the organ, disinfection of the organ or tissue and homeostasis of the organ.

The initial step in decellularizing an organ vascularized structure or tissue can include to cannulate the organ or tissue. The vessels, ducts, and/or cavities of an organ or tissue may be cannulated using methods and materials known in the art. Next, the cannulated organ vascularized structure or tissue can be perfused with a cellular disruption medium. Perfusion through an organ can be multi-directional (e.g., antegrade and retrograde). Alternatively, decellularization can be achieved by immersion of an organ or portion thereof into a cellular disruption medium. Methods described herein can include the use of perfusion or immersion decellularized extracellular matrices.

Langendorff perfusion of a heart is routine in the art, as is physiological perfusion (also known as four chamber working mode perfusion). See, for example, Dehnert, The Isolated Perfused Warm-Blooded Heart According to Langendorff, In Methods in Experimental Physiology and Pharmacology: Biological Measurement Techniques V. Biomesstechnik-Verlag March GmbH, West Germany, 1988.

Briefly, for Langendorff perfusion, the aorta can be cannulated and attached to a reservoir containing physiological solution to allow the heart to function outside of the body for a specified duration of time. To achieve perfusion decellularization the protocol has been modified to perfuse a cellular disruption medium delivered in a retrograde direction down the aorta either at a constant flow rate delivered, for example, by an infusion or roller pump or by a constant hydrostatic pressure pump. In both instances, the aortic valves can be forced shut and the perfusion fluid can be directed into the coronary ostia (thereby perfusing, via antegrade, the entire ventricular mass of the heart), which then drains into the right atrium via the coronary sinus. For working mode perfusion, a second cannula can be connected to the left atrium and perfusion can be changed to retrograde.

In one embodiment, a physiological solution can include phosphate buffer saline (PBS). In one embodiment, the physiological solution can be a physiologically compatible buffer supplemented with, e.g., nutritional supplements (for instance, glucose). For example, for heart, the physiological solution may be Modified Krebs-Henseleit buffer having 118 mM NaCl, 4.7 mM KCl, 1.2 mM $MgSO_4$, 1.2 mM $KH_2PO_4$, 25 mM $NaHCO_3$, 11 mM glucose, 1.75 mM $CaCl_2$, 2.0 mM pyruvate and 5 U/L insulin; or Krebs buffer containing 118 mM NaCl, 4.7 mM KCl, 25 mM $NaHCO_3$, 1.2 mM $MgSO_4$, 1.2 mM $KH_2PO_4$, 2 mM $CaCl_2$) gassed with 95% $O_2$, 5% $CO_2$. Hearts may be perfused with glucose (e.g., about 11 mM) as a sole substrate or in combination with about 1 or 1.2 mM palmitate. For kidney, the physiological solution may be KPS-1® Kidney Perfusion Solution. For liver, the physiological solution may be Krebs-Henseleit buffer having 118 mM NaCl, 4.7 mM KCl, 1.2 mM $MgSO_4$, 1.2 mM $KH_2PO_4$, 26 mM $NaHCO_3$, 8 mM glucose, and 1.25 mM $CaCl_2$) supplemented with 2% BSA.

One or more cellular disruption media may be used to decellularize an organ or tissue. A cellular disruption medium generally includes at least one detergent such as but not limited to SDS, PEG, CHAPS or Triton X. A cellular disruption medium can include water such that the medium can be osmotically incompatible with the cells. Alternatively, a cellular disruption medium can include a buffer (e.g., PBS) for osmotic compatibility with the cells. Cellular disruption media also may include enzymes such as, without limitation, one or more collagenases, one or more dispases, one or more DNases, or a protease such as trypsin. In some instances, cellular disruption media also or alternatively may include inhibitors of one or more enzymes (e.g., protease inhibitors, nuclease inhibitors, and/or collegenase inhibitors).

In certain embodiments, a cannulated organ or tissue may be perfused sequentially with two different cellular disruption media. For example, the first cellular disruption medium may include an anionic detergent such as SDS and the second cellular disruption medium can include an ionic detergent such as Triton X. Following perfusion with at least one cellular disruption medium, a cannulated organ or tissue may be perfused, for example, with wash solutions and/or solutions containing one or more enzymes such as those disclosed herein.

Alternating the direction of perfusion (e.g., antegrade and retrograde) may assist in decellularizing the entire organ or tissue. Decellularization generally decellularizes the organ from the inside out, resulting in very little damage to the ECM. An organ or tissue may be decellularized at a suitable temperature between 4 and 40° ° C. Depending upon the size and weight of an organ or tissue and the particular detergent(s) and concentration of detergent(s) in the cellular disruption medium, an organ or tissue generally can be perfused from about 0.05 hours to about 5 hours, per gram of solid organ or tissue (generally >50 grams), or about 2 hours to about 12 hours, per gram of solid organ or tissue for organs (generally <50 grams), with cellular disruption medium. Including washes, an organ may be perfused for up to about 0.75 hours to about 10 hours per gram of solid organ or tissue (generally >50 grams), or about 12 hours to about 72 hours, per gram of tissue (generally <50 grams). Decellularization time can be dependent upon the vascular and cellular density of the organ or tissue with limited scaling for overall mass. Therefore, as general guidance the time ranges and masses above are provided. Perfusion generally can be adjusted to physiologic conditions including pulsatile flow, rate and pressure.

A decellularized organ or tissue has the extracellular matrix (ECM) component of all or most regions of the organ or tissue, including ECM components of the vascular tree. ECM components can include any or all of the following: fibronectin, fibrillin, laminin, elastin, members of the collagen family (e.g., collagen I, III, and IV), ECM associated growth proteins including growth factors and cytokines, glycosaminoglycans, ground substance, reticular fibers and thrombospondin, which can remain organized as defined structures such as the basal lamina. Successful decellularization can be defined as the absence of detectable myofilaments, endothelial cells, smooth muscle cells, and nuclei in histologic sections using standard histological staining procedures or removal of over 97% of detectable DNA as measured by fluorometric assay. Residual cell debris may be removed from the decellularized organ or tissue.

The morphology and the architecture of the ECM can be maintained during and following the process of decellularization. "Morphology" as used herein refers to the overall shape of the organ, tissue or of the ECM, while "architecture" as used herein refers to the exterior surface, the interior surface, and the ECM therebetween.

The morphology and architecture of the ECM may be examined visually and/or histologically. For example, the basal lamina on the exterior surface of a solid organ or within the vasculature of an organ or tissue should not be removed or significantly damaged due to perfusion decellularization. In addition, the fibrils of the ECM should be similar to or significantly unchanged from that of an organ or tissue that has not been decellularized.

One or more compounds may be applied in or on a decellularized organ or tissue to, for example, preserve the decellularized organ, or to prepare the decellularized organ or tissue for recellularization and/or to assist or stimulate cells during the recellularization process. Such compounds include, but are not limited to, one or more growth factors (e.g., VEGF, DKK-1, FGF, BMP-1, BMP-4, SDF-1, IGF, and HGF), immune modulating agents (e.g., cytokines, glucocorticoids, IL2R antagonist, leucotriene antagonists), and/or factors that modify the coagulation cascade (e.g., aspirin, heparin-binding proteins, and heparin). In addition, a decellularized organ or tissue may be further treated with, for example, irradiation (e.g., UV, gamma) to reduce or eliminate the presence of any type of microorganism remaining on or in a decellularized organ or tissue.

Recellularization of Organs or Tissues

A molded, irradiated decellularized portion of an organ or tissue may be contacted with a population of cells, either differentiated (mature or primary) cells, stem cells, or partially differentiated cells. Thus, the cells can be totipotent cells, pluripotent cells, or multipotent cells, and can be uncommitted or committed, and may be single-lineage cells. The cells may be undifferentiated cells, partially differentiated cells, or fully differentiated cells including fetal derived cells. Cells may include progenitor cells, precursor cells, or "adult" derived stem cells including umbilical cord cells and fetal stem cells. Cells useful in the matrices of the invention include embryonic stem cells (as defined by the National Institute of Health (NIH); see, for example, the Glossary at stemcells.nih.gov on the World Wide Web) and iPS cells.

Examples of cells that can be used to recellularize a portion of an organ or tissue include, without limitation, embryonic stem cells, umbilical cord blood cells, tissue-derived stem or progenitor cells, bone marrow-derived step or progenitor cells, blood-derived stem or progenitor cells, mesenchymal stem cells (MSC), skeletal muscle-derived cells, multipotent adult progentitor cells (MAPC), or iPS cells Additional cells that can be used include cardiac stem cells (CSC), multipotent adult cardiac-derived stem cells, cardiac fibroblasts, cardiac microvasculature endothelial cells, aortic endothelial cells, coronary endothelial cells, microvascular endothelial cells, venous endothelial cells, arterial endothelial cells, smooth muscle cells, cardiomyocytes, hepatocytes, beta-cells, keratinocytes, purkinji fibers, neurons, bile duct epithelial call, islet cells, pneumocytes, clara cells, brush boarder cells, or podocytes. Bone marrow-derived stem cells such as bone marrow mononuclear cells (BM-MNC), endothelial or vascular stem or progenitor cells, and peripheral blood-derived stem cells such as endothelial progenitor cells (EPC) may also be used as cells.

The number of cells that are introduced into and onto a perfusion decellularized scaffold may depend both the organ (e.g., which organ, the size and weight of the organ) or tissue and the type and developmental stage of the regenerative cells. Different types of cells may have different tendencies as to the population density those cells will reach. Similarly, different organ or tissues may be cellularized at different densities. By way of example, a decellularized organ or tissue can be "seeded" with at least about 500, 1,000 (e.g., at least 10,000, 100,000, 1,000,000, 10,000,000, or 100,000,000) cells; or can have from about 1,000 cells/mg tissue (wet weight, e.g., prior to decellularization) to about 10,000,000 cells/mg tissue (wet weight) attached thereto.

Cells can be introduced ("seeded") into a decellularized organ or tissue by injection into one or more locations. In addition, more than one type of cell may be introduced into a decellularized organ or tissue. For example, a population of differentiated cell types can be injected at multiple positions in a decellularized organ or tissue or different cell types may be injected into different portions of a decellularized organ or tissue. Alternatively, or in addition to injection, cells or a cocktail of cells may be introduced by perfusion into a cannulated decellularized organ or tissue. For example, cells can be perfused into a decellularized organ using a perfusion medium, which can then be changed to an expansion and/or differentiation medium to induce growth and/or differentiation of the cells. Location specific differentiation may be achieved by placing cells into the various locations within the organ, e.g., into regions of the heart, such as, atrial, ventricular or nodal.

During recellularization, a portion of an organ or tissue can be maintained under conditions in which at least some of the cells can multiply and/or differentiate within and on the decellularized organ or tissue. Those conditions include, without limitation, the appropriate temperature and/or pressure, electrical and/or mechanical activity, force, the appropriate amounts of $O_2$ and/or $CO_2$, an appropriate amount of humidity, and sterile or near-sterile conditions. During recellularization, the decellularized portion of an organ or tissue and the regenerative cells attached thereto can be maintained in a suitable environment. For example, the cells may require a nutritional supplement (e.g., nutrients and/or a carbon source such as glucose), exogenous hormones or growth factors, and/or a particular pH.

Cells may be allogeneic to a decellularized organ or tissue (e.g., a human decellularized organ or tissue seeded with human cells), or cells may be xenogeneic to a decellularized organ or tissue (e.g., a pig decellularized organ or tissue seeded with human cells). "Allogeneic" as used herein refers to cells obtained from the same species as that from which the organ or tissue originated (e.g., related or unrelated individuals), while "xenogeneic" as used herein refers to cells obtained from a species different than that from which the organ or tissue originated.

Perfusion decellularized matrices of organs with a substantially closed vascular system can be useful because perfusion decellularization preserves the intact matrix and microenvironment, including an intact vascular and microvascular system, that vascular system, or ducts or other conduits, may be utilized to deliver cells as well as nutrients and/or differentiation or maintenance factors, to the cells in vitro. Cells and nutrients and/or other factors may be delivered by other means, e.g., injection, or passive means, or a combination thereof. In one embodiment, a cell population of interest can be perfused into the perfusion decellularized organ ECM after inflation allowing for the seeding into the interstitial space or matrix outside of the vascular conduits. This includes the active migration and/or homing of cells to their native microstructure, e.g. the homing of endothelial cells to the vasculature. In one embodiment, a cell population of interest can be perfused into the perfusion decellularized ECM followed by a second cell population, e.g., a beta cell population can be introduced followed by an endothelial cell population, where the endothelial cells remain in the vascular conduits as in their native microenvironment. In one embodiment, a cell population of interest can be perfused into the perfusion decellularized ECM after inflation followed by a second cell population, e.g., an endothelial cell population can be introduced followed by a population of cells that include beta cells, where the endothelial cells remain in the vascular conduits as in their native microenvironment. In another embodiment, two or more cell populations can be combined and perfused together. In another embodiment, two or more distinct cell populations can be introduced serially through either perfusion, direct injection or a combination of both.

The cells may be introduced in media that support the proliferation, metabolism, and/or differentiation of the cells. Alternatively, after the cells have populated the ECM, the medium can be changed to one that supports the proliferation, metabolism and differentiation of the cells. The cultured cells may exist in the ECM at physiological cell densities and, in the presence of media that support the proliferation, metabolism, and/or differentiation of the cells and/or the appropriate microenvironment in the ECM, allow for the maintenance and/or functional differentiation of the cells.

Stem or progenitor media may contain a variety of components including, for example, KODMEM medium (Knockout Dulbecco's Modified Eagle's Medium), DMEM, Ham's F12 medium, FBS (fetal bovine serum), FGF2 (fibroblast growth factor 2), KSR or hLIF (human leukemia inhibitory factor). The cell differentiation media may also contain supplements such as L-Glutamine, NEAA (nonessential amino acids), P/S (penicillin/streptomycin), N2, B27 and beta-mercaptoethanol. It is contemplated that additional factors may be added to the cell differentiation media, including, but not limited to, fibronectin, laminin, heparin, heparin sulfate, retinoic acid, members of the epidermal growth factor family (EGFs), members of the fibroblast growth factor family (FGFs) including FGF2, FGF7, FGF8, and/or FGF10, members of the platelet derived growth factor family (PDGFs), transforming growth factor (TGF)/bone morphogenetic protein (BMP)/growth and differentiation factor (GDF) factor family antagonists including but not limited to noggin, follistatin, chordin, gremlin, cerberus/DAN family proteins, ventropin, high dose activin, and amnionless or variants or functional fragments thereof. TGF/BMP/GDF antagonists could also be added in the form of TGF/BMP/GDF receptor-Fc chimeras. Other factors that may be added include molecules that can activate or inactivate signaling through Notch receptor family, including but not limited to proteins of the Delta-like and Jagged families as well as inhibitors of Notch processing or cleavage, or variants or functional fragments thereof. Other growth factors may include members of the insulin like growth factor family (IGF), insulin, the wingless related (WNT) factor family, and the hedgehog factor family or variants or functional fragments thereof. Additional factors may be added to promote mesendoderm stem/progenitor, endoderm stem/progenitor, mesoderm stem/progenitor, or definitive endoderm stem/progenitor proliferation and survival as well as survival and differentiation of derivatives of these progenitors.

In one embodiment, perfusion decellularized matrices can be combined with iPS or ES cells differentiated using the embryoid body (EB) method. For example, human iPS cell lines reprogrammed by transduction, e.g., lentiviral-mediated transduction, of transcription factors (OCT4, SOX2, NANOG and LIN28; Oct3/4, Sox2, Klf4, and c-Myc; or Oct3/4, Sox2, and Klf4) can be employed. iPS clones of fetal origin or of newborn origin may be employed. Human ES cell lines may also be employed. iPS cells and ES cells may be maintained on irradiated mouse embryonic fibroblasts (MEFs) at a density of 19,500 cells/cm2 in 6-well culture plates (Nunc) in DMEM/F12 culture medium supplemented with 20% KnockOut serum replacer (Invitrogen), 0.1 mmol/L nonessential amino acids, 1 mmol/L L-glutamine, and 0.1 mmol/L ß-mercaptoethanol (Sigma). In addition, the medium may be supplemented with 100 ng/mL, zebrafish basic fibroblast growth factor for iPS cells, and with 4 ng/mL human recombinant basic fibroblast growth factor (Invitrogen) for hES cells. iPS and ES cell lines may also be maintained on gelatinized 100-mm dishes in DMEM (Sigma-Aldrich) containing 15% fetal calf serum (FCS; Sigma-Aldrich), 0.1 µmol/L 2-mercaptoethanol (2 ME), and 1,000 units/ml LIF (Chemicon International). For differentiation, these cells may treated with 0.25% Trypsin/ethylenediaminetetraacetic acid (GIBCO), and transferred to gelatinized 6-well plates in α-minimum essential medium (GIBCO) supplemented with 10% FCS and 0.05 µmol/L 2 ME, at a concentration of $3 \times 10^4$ cells/well.

Colonies may be detached from culture plates by incubating with 1 mg/mL dispase (Gibco) solution at 37° C. for 8 to 15 minutes and placed in ultralow attachment plates in suspension culture, e.g., for 4 days. During suspension culture, the medium may be changed at day 1 followed by culture for another 3 days without medium change. EBs can then be plated on 0.1% gelatin-coated culture plates, e.g., at the density or 50 to 100 EBs per well, or in the perfusion decellularized ECM and cultured in differentiation medium (e.g., changed daily).

In some instances, an organ or tissue generated by the methods described herein can be transplanted into a patient. In those cases, the cells used to recellularize a decellularized organ or tissue can be obtained from the patient such that the cells are "autologous" to the patient. Cells from a patient can be obtained from, for example, blood, bone marrow, tissues, or organs at different stages of life (e.g., prenatally, neonatally or perinatally, during adolescence, or as an adult) using methods known in the art. Alternatively, cells used to recellularize a decellularized organ or tissue may be syngeneic (i.e., from an identical twin) to the patient, cells can be human lymphocyte antigen (HLA)-matched cells from, for example, a relative of the patient or an HLA-matched individual unrelated to the patient, or cells can be allogeneic to the patient from, for example, a non-HLA-matched donor.

Irrespective of the source of the cells (e.g., autologous or not), the decellularized solid organ can be autologous, allogeneic or xenogeneic to a patient.

The progress of cells can be monitored during recellularization. For example, the number of cells on or in an organ or tissue can be evaluated by taking a biopsy at one or more time points during recellularization. In addition, the amount of differentiation that cells have undergone can be monitored by determining whether or not various markers are present in a cell or a population of cells. Markers associated with different cells types and different stages of differentiation for those cell types are known in the art, and can be readily detected using antibodies and standard immunoassays. See, for example, Current Protocols in Immunology, 2005, Coligan et al., Eds., John Wiley & Sons, Chapters 3 and 11. Nucleic acid assays as well as morphological and/or histological evaluation can be used to monitor recellularization.

Exemplary Uses for the Molded, Irradiated ECM

The ECM may be molded to form a product useful to treat, for example, diseases of the eye, adnexa, ear, and mastoid process including but not limited to lacrimal fistula, mastoid fistula craniofistula, e.g., between the intracranial space and a paranasal sinus, labyrinthine fistula, perilymph fistula, or preauricular fistula; diseases of the circulatory system including but not limited to coronary arteriovenous fistula, arteriovenous fistula, e.g., of the pulmonary vessels cerebral arteriovenous fistula, acquired, or fistula of an artery; diseases of the respiratory system including but not limited to pyothorax with fistula or tracheoesophageal fistula; diseases of the digestive system including but not limited to duodeno biliary fistula, e.g., salivary gland fistula, fistula of stomach and duodenum, gastrocolic fistula, gastrojejunocolic fistula, enterocutaneous fistula, gastric fistula from the stomach to the skin surface, fistula of appendix, anal and rectal fissures and fistulas, e.g., anal fistula or anorectal fistula (fecal fistula, fistula-in-ano), fistula of intestine, e.g., enteroenteral fistula: between two parts of the intestine, fistula of gallbladder or fistula of bile duct, e.g., biliary fistula, or pancreatic fistula: between the pancreas and the exterior via the abdominal wall; diseases of the musculoskeletal system and connective tissue including fistula of joint; diseases of the urogenital system including but not limited to vesicointestinal fistula, urethral fistula, fistula of nipple, fistulae involving female genital tract/obstetric fistula including, e.g., vesicovaginal fistula, cervical fistula, enterovaginal fistula: between the intestine and the vagina, rectovaginal fistula, other female intestinal-genital tract fistulae, or female genital tract-skin fistulae; congenital malformations, deformations and chromosomal abnormalities including but not limited to sinus, fistula and cyst of branchial cleft, congenital preauricular fistula, portal vein-hepatic artery fistula, congenital fistula of lip, congenital fistula of salivary gland, congenital absence, atresia and stenosis of rectum with fistula, congenital absence, atresia and stenosis of anus with fistula, congenital fistula of rectum and anus, congenital fistulae between uterus and digestive and urinary tracts, or congenital rectovaginal fistula; or external causes including but not limited to traumatic arteriovenous fistula or persistent postoperative fistula.

For example, a hydrated plug (with or without a delivery device) can be inserted in an internal opening and then pulled through the tract until light resistance can be met and then sutured securely in the primary opening. Excess plug from the external opening may be trimmed at the skin level. The tract may be irrigated with hydrogen peroxide or other anti-microbial solution before insertion. The external opening may be partially open as this is the path that allows drainage and prevents a closed-space infection. The maturing of the tract, making the wall more fibrotic, which results in increased healing, may minimize sepsis and facilitate fistula closure when used in conjunction with other procedures, such as an advancement flap.

Nerve scarring can cause severe pain and dysfunction. Treatment of the scarred nerve frequently yields unpredictable results. A barrier wrap around the scarred nerve may be of benefit in preventing the recurrence of epineural scarring following neurolysis. Nerve wraps may inhibit recurrent nerve tissue adhesions and diminish inflammatory and immunologic reactions in peripheral nerve surgery. Nerve wraps may serve as a nerve guide, e.g., across nerve discontinuities, and a nerve protector, e.g., following decompression procedures or nerve isolation in traumatized nerve beds or closure around partially severed nerves. Exemplary lengths and diameters of nerve wraps include a length of about 2.5 cm or 5.0 cm and a diameter of about 4 mm, 6 mm, or 12 mm).

Tendon wraps can be an interface between the tendon and the tendon sheath or the surrounding tissue and may be used in the treatment of bowed tendons, occelets, splints, shins and suspensory injuries, tendon repair surgery, including reinforcement of the rotator cuff, patella, achilles, biceps, quadriceps, or other tendons.

While exemplary embodiments have been shown and described herein, it will be obvious to those skilled in the art that such embodiments are provided by way of example only. Numerous variations, changes, and substitutions will occur to those skilled in the art. It should be understood that various alternatives to the embodiments described herein may be employed. It is intended that the following claims define the scope of the disclosure and that methods and structures within the scope of these claims and their equivalents be covered thereby.

What is claimed is:

1. A system, comprising:
an isolated molded, at least partially irradiated portion of an at least partially decellularized extracellular matrix from a mammalian organ or tissue, the at least partially decellularized extracellular matrix from the mammalian organ or tissue having a scaffold comprising a plurality of collagen fibers surrounding a plurality of empty cellular compartments and having an architecture of the extracellular matrix or portion thereof prior to decellularization when placed inside of a mold or constraining device and exposed to radiation,
wherein the isolated molded, at least partially irradiated portion of the at least partially decellularized extracellular matrix has reduced malleability relative to a comparable, non-irradiated portion and is in the form of a cylinder, cube, rectangular prism, or irregular strip, depending on a configuration of the mold or constraining device, and
wherein the system does not include a surgical mesh.

2. The system of claim 1, wherein the isolated molded, at least partially irradiated portion of the at least partially decellularized extracellular matrix is in the form of the irregular strip, which is configured as a nerve or tendon wrap.

3. The system of claim 1, further comprising a surgical filler deployment device having a hollow portion, and wherein the isolated molded, at least partially irradiated portion of the at least partially decellularized extracellular matrix has been placed into the hollow portion.

4. The system of claim 3, wherein the isolated molded, at least partially irradiated portion of the at least partially decellularized extracellular matrix is deployable from the hollow portion of the surgical filler deployment device.

5. The system of claim 3, wherein the surgical filler deployment device includes a pusher or plunger configured to push the isolated molded, at least partially irradiated portion of the at least partially decellularized extracellular matrix into a tissue tract.

6. The system of claim 3, wherein the hollow portion of the surgical filler deployment device includes a non-rigid wall or a wall having an opening.

7. The system of claim 4, wherein the isolated molded, at least partially irradiated portion of the at least partially decellularized extracellular matrix is configured to be pulled or pushed from the hollow portion of the surgical filler deployment device.

8. The system of claim 1, wherein the isolated molded, at least partially irradiated portion of the at least partially decellularized extra cellular matrix has been secured to a string or suture.

9. The system of claim 1, wherein the isolated molded, at least partially irradiated portion of the at least partially decellularized extracellular matrix is configured to be sutured to an opening of a tissue tract.

10. The system of claim 1, wherein the isolated molded, at least partially irradiated portion of the at least partially decellularized extracellular matrix is in the form of the cylinder, which is configured for repairing a fistula.

11. The system of claim 1, wherein the isolated molded, at least partially irradiated portion of the at least partially decellularized extracellular matrix was radiated with E-beam radiation or gamma radiation.

12. The system of claim 1, wherein the isolated molded, at least partially irradiated portion of the at least partially decellularized extracellular matrix was radiated with thermal or UV radiation.

13. The system of claim 1, wherein the isolated molded, at least partially irradiated portion of the at least partially decellularized extracellular matrix is a perfusion decellularized extracellular matrix.

14. The system of claim 1, wherein the isolated molded, at least partially irradiated portion of the at least partially decellularized extracellular matrix has been inflated with a gas or vapor prior to radiation.

15. The system of claim 1, wherein the scaffold of the at least partially decellularized extracellular matrix encompasses components of the mammalian organ or tissue's vascular tree.

16. A method, comprising:
a) providing an at least partially hydrated at least partially decellularized extracellular matrix or portion thereof from a mammalian organ or tissue or a portion thereof, the at least partially decellularized extracellular matrix or portion thereof having a scaffold comprising a plurality of collagen fibers surrounding a plurality of empty cellular compartments and having an architecture of the extracellular matrix or portion thereof prior to decellularization,
b) placing the scaffold of the at least partially hydrated at least partially decellularized extracellular matrix or portion thereof from the mammalian organ or tissue or the portion thereof but not a surgical mesh into a mold having a selected shape; and
c) subjecting the at least partially hydrated at least partially decellularized extracellular matrix or portion thereof from the mammalian organ or tissue or the portion thereof in the mold to a selected dose of radiation to provide for at least partial maintenance or at least partial inhibition of an alteration in the volume or shape of the at least partially hydrated at least partially decellularized extracellular matrix or portion thereof that is in the mold, or dehydrating the at least partially hydrated at least partially decellularized extracellular matrix or portion thereof from the mammalian organ or tissue or the portion thereof in the mold prior to subjecting it to a selected dose of radiation.

17. The method of claim 16, wherein subjecting the at least partially hydrated at least partially decellularized extracellular matrix or portion thereof from the mammalian organ or tissue or the portion thereof in the mold to the selected dose of radiation includes at least partially reducing malleability of the at least partially hydrated at least partially decellularized extracellular matrix or portion thereof from the mammalian organ or tissue or the portion thereof in the mold.

18. The method of claim 16, wherein the mammalian organ is from a pig or human or the mammalian organ is a liver, muscle, lung, spleen or heart.

19. The method of claim 16, wherein the selected dose of radiation is from about 5 kGy to about 50 kGy or wherein the radiation is E-beam radiation, gamma, thermal or UV radiation.

20. The method of claim 16, wherein placing the scaffold of the at least partially hydrated at least partially decellularized extracellular matrix or portion thereof from the mammalian organ or tissue or the portion thereof into the mold includes pressing multiple layers of scaffolds of the at least partially hydrated at least partially decellularized extracellular matrix or portion thereof from the mammalian organ or tissue or portion thereof into the mold.

21. The method of claim 16, wherein the at least partially hydrated at least partially decellularized extracellular matrix or portion thereof from the mammalian organ or tissue or the portion thereof is from about 1 cm×1 cm to about 60 cm×60 cm or from about 0.5 cm×0.5 cm×0.5 cm to about 30 cm×30 cm×30 cm, or wherein the at least partially hydrated at least partially decellularized extracellular matrix or portion thereof from the mammalian organ or tissue or the portion thereof is from about 1 cm×1 cm to about 10 cm×10 cm, from about 1 cm×2 cm to about 10 cm×12 cm, or from about 1 cm×6 cm to about 3 cm×20 cm.

22. The method of claim 16, further comprising inflating the at least partially hydrated at least partially decellularized extracellular matrix or portion thereof from the mammalian organ or tissue or the portion thereof with a gas or vapor prior to radiation.

23. The method of claim 16, wherein the at least partially hydrated at least partially decellularized extracellular matrix or portion thereof from the mammalian organ or tissue or the portion thereof prior to radiation has the shape of a cube, a rectangular prism, or an irregular strip.

24. The method of claim 16, wherein placing the scaffold of the at least partially hydrated at least partially decellularized extracellular matrix or portion thereof from the mammalian organ or tissue or a portion thereof into the mold and subjecting it to the selected dose of radiation includes forming an isolated molded, at least partially irradiated portion of the at least partially hydrated at least partially decellularized extracellular matrix or portion thereof.

* * * * *